United States Patent
Smith et al.

(10) Patent No.: US 12,419,921 B2
(45) Date of Patent: Sep. 23, 2025

(54) METHODS OF PROMOTING SCFA PRODUCTION BY GUT MICROBIOTA

(71) Applicant: MULTIGERM UK ENTERPRISES LTD, Farnham (GB)

(72) Inventors: Barry Smith, Farnham (GB); Michael Butler, Farnham (GB)

(73) Assignee: MULTIGERM UK ENTERPRISES LTD, Surrey (GB)

( * ) Notice: Subject to any disclaimer, the term of this patent is extended or adjusted under 35 U.S.C. 154(b) by 725 days.

(21) Appl. No.: 17/769,125

(22) PCT Filed: Oct. 16, 2020

(86) PCT No.: PCT/GB2020/052621
§ 371 (c)(1),
(2) Date: Apr. 14, 2022

(87) PCT Pub. No.: WO2021/074649
PCT Pub. Date: Apr. 22, 2021

(65) Prior Publication Data
US 2023/0053778 A1 Feb. 23, 2023

(30) Foreign Application Priority Data
Oct. 18, 2019 (GB) ...................................... 1915144

(51) Int. Cl.
*A61K 35/747* (2015.01)
(52) U.S. Cl.
CPC .................................. *A61K 35/747* (2013.01)
(58) Field of Classification Search
CPC ................ A61K 35/747; A61K 35/744; A23V 2002/00; Y02A 50/30; A23L 33/40; A23L 33/135; A61P 1/16; A61P 25/16; A61P 1/00
See application file for complete search history.

(56) References Cited

U.S. PATENT DOCUMENTS

| | | |
|---|---|---|
| 2017/0106025 A1 | 4/2017 | Kovarik |
| 2018/0318323 A1 | 11/2018 | Roman et al. |
| 2018/0357375 A1 | 12/2018 | Cutcliffe et al. |
| 2019/0117709 A1 | 4/2019 | Kovarik |
| 2020/0121743 A1 | 4/2020 | Kovarik |

FOREIGN PATENT DOCUMENTS

| | | | |
|---|---|---|---|
| WO | 2006/035218 | 4/2006 | |
| WO | WO-2013072654 A1 * | 5/2013 | ........... A61K 35/744 |
| WO | 2014/068338 | 5/2014 | |
| WO | 2017/134240 | 8/2017 | |
| WO | 2019/032572 | 2/2019 | |
| WO | 2019/151843 | 8/2019 | |

OTHER PUBLICATIONS

Mayo Clinic Parkinson's disease diganosis and treatment, retrieved on Mar. 14, 2025, 21 pages of PDF. (Year: 2025).*
Mertsalmi TH, Aho VTE, Pereira PAB, Paulin L, Pekkonen E, Auvinen P, Scheperjans F. More than constipation—bowel symptoms in Parkinson's disease and their connection to gut microbiota. Eur J Neurol. Nov. 2017;24(11):1375-1383. doi: 10.1111/ene. 13398. Epub Sep. 11, 2017. PMID: 28891262. Abstract Only.*
International Preliminary Report on Patentability issued Apr. 19, 2022 in corresponding International (PCT) Patent Application No. PCT/GB2020/052621.
International Search Report issued Jun. 28, 2021 in corresponding International (PCT) Patent Application No. PCT/GB2020/052621.
"Efficacy of an oral probiotic (Symprove) on motor and non-motor symptoms in Parkinson's disease: a novel randomised, double-blind, placebo-controlled study (SVM-PD)", Patient Information Sheet, King's College Hospital, NHS Foundation Trust, 2019, SYM=PD 2, IRAS: 252293, pp. 2-5E.
Srivastav, S. et al., "Probiotics mixture increases butyrate, and subsequently rescues the nigral dopaminergic neurons from MPTP and rotenone-induced neurotoxicity", Journal of Nutritional Biochemistry, 2019, vol. 69, pp. 73-86.
Moens, F. et al., "A four-strain probiotic exerts positive immunomodulatory effects by enhancing colonic butyrate production in vitro", International Journal of Pharmaceutics, 2019, vol. 555, pp. 1-10.
Tamtaji, O.R. et al., "Clinical and metabolic response to probiotic administration in people with Parkinson's disease: A randomized, double-blind, placebo-controlled trial", Clinical Nutrition, 2018, pp. 1-5, doi.org/10.1016/j.clnu.2018.05.018.

* cited by examiner

Primary Examiner — Kade Ariani
(74) Attorney, Agent, or Firm — Wenderoth, Lind & Ponack, L.L.P.

(57) ABSTRACT

The invention relates to methods for promoting SCFA production by gut microbiota by administering a liquid, water-based probiotic composition. The methods are particularly effective at promoting gut health. The invention further relates to methods of promoting intestinal barrier integrity, methods of promoting a tolerogenic gut phenotype, and methods of treating Parkinson's Disease.

20 Claims, 33 Drawing Sheets

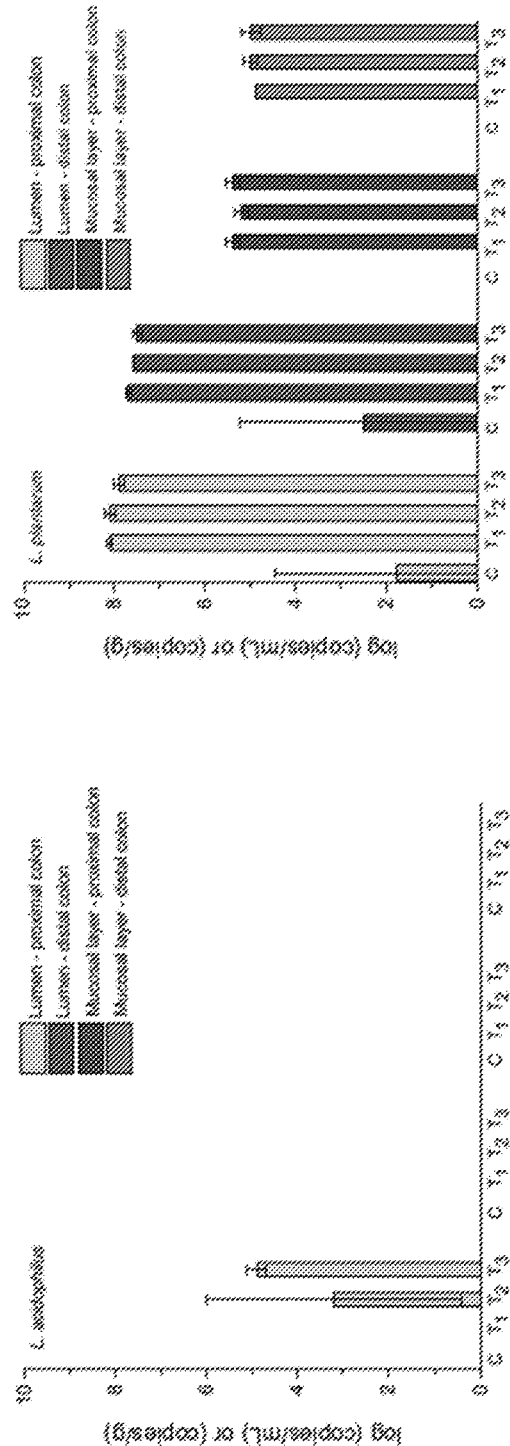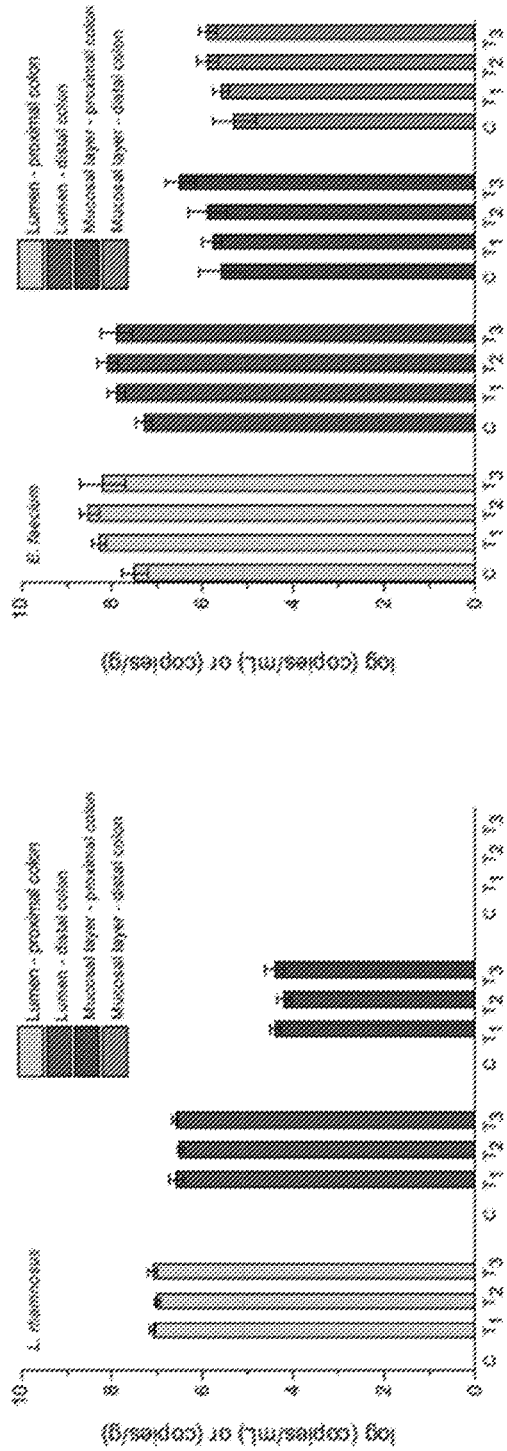
Figure 2

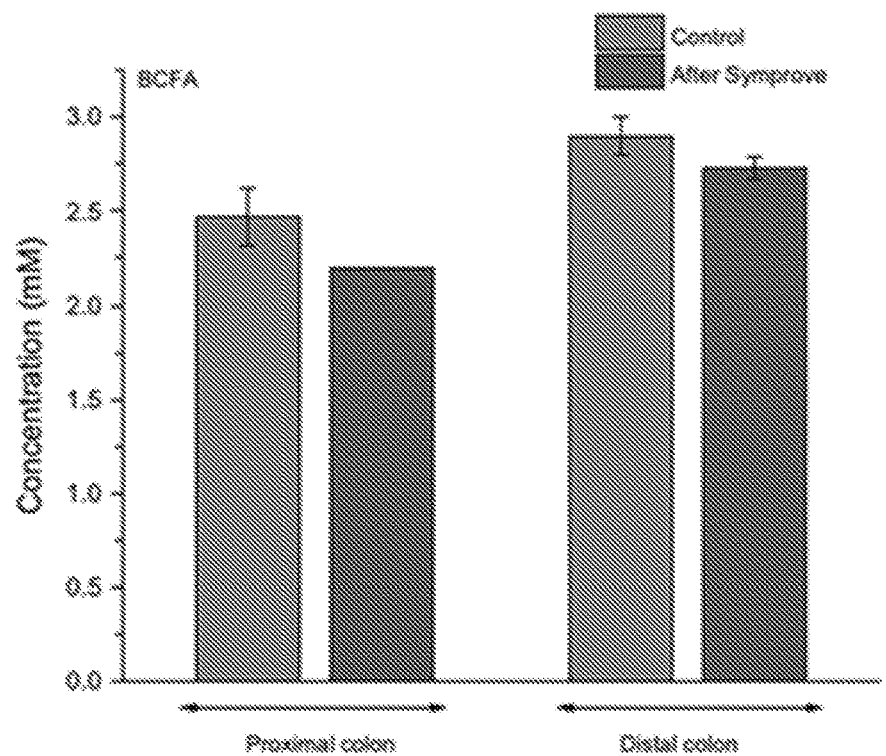
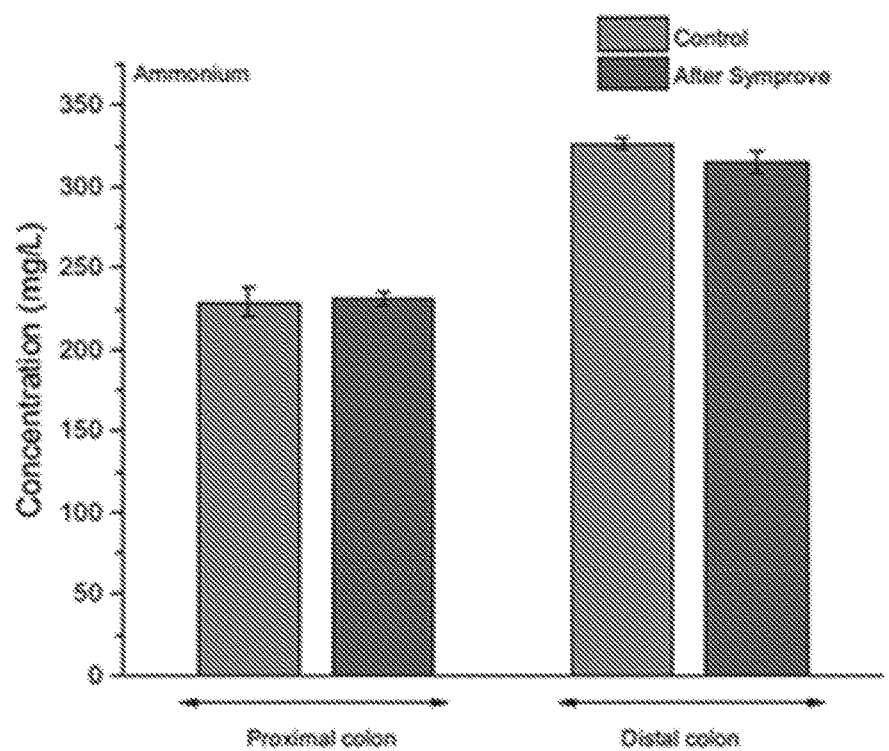
Figure 4

| Phylum | Family | Lumen Donor A Proximal colon | | Distal colon | | Donor B Proximal colon | | Distal colon | | Donor C Proximal colon | | Distal colon | |
|---|---|---|---|---|---|---|---|---|---|---|---|---|---|
| | | C | TR | C | TR | C | TR | C | TR | C | TR | C | TR |
| Actinobacteria | Bifidobacteriaceae | 3.0 | 10.3 | 0.6 | 2.7 | 8.9 | 19.0 | 5.6 | 9.2 | 14.3 | 12.2 | 11.6 | 12.3 |
| | Coriobacteriaceae | 0.0 | 0.1 | 0.0 | 0.1 | 0.1 | 0.1 | 0.2 | 0.1 | 0.1 | 0.1 | 0.2 | 0.1 |
| | Eggerthellaceae | 0.0 | 0.0 | 0.0 | 0.1 | 0.0 | 0.0 | 0.0 | 0.0 | 0.0 | 0.0 | 0.0 | 0.0 |
| | Microbacteriaceae | 0.8 | 1.5 | 0.2 | 0.9 | 0.8 | 0.2 | 0.5 | 0.4 | 0.6 | 0.4 | 0.5 | 0.5 |
| Bacteroidetes | Bacteroidaceae | 23.2 | 12.5 | 31.0 | 28.0 | 28.3 | 12.5 | 32.2 | 14.9 | 11.0 | 12.8 | 31.6 | 20.4 |
| | Barnesiellaceae | 0.0 | 0.0 | 0.0 | 0.0 | 0.0 | 0.0 | 0.0 | 0.0 | 0.0 | 0.0 | 0.0 | 0.0 |
| | Marinifilaceae | 0.0 | 0.0 | 0.0 | 0.0 | 0.0 | 0.0 | 0.0 | 0.0 | 0.0 | 0.0 | 0.0 | 0.5 |
| | Prevotellaceae | 0.0 | 0.0 | 0.1 | 0.1 | 0.0 | 0.5 | 0.3 | 0.2 | 0.0 | 0.0 | 0.2 | 0.4 |
| | Rikenellaceae | 0.0 | 0.5 | 0.9 | 0.9 | 0.0 | 0.0 | 2.2 | 1.5 | 0.0 | 0.6 | 5.7 | 1.9 |
| | Tannerellaceae | 0.6 | 3.4 | 8.6 | 6.2 | 2.3 | 3.7 | 3.7 | 5.0 | 2.6 | 4.9 | 3.5 | 3.1 |
| Firmicutes | Acidaminococcaceae | 3.4 | 0.0 | 0.0 | 0.0 | 0.0 | 0.0 | 0.0 | 0.0 | 0.0 | 0.0 | 0.0 | 0.0 |
| | Clostridiaceae | 0.0 | 9.5 | 0.4 | 2.7 | 3.3 | 2.6 | 0.6 | 1.8 | 0.6 | 1.3 | 0.2 | 0.8 |
| | Enterococcaceae | 2.0 | 0.0 | 0.0 | 0.0 | 0.0 | 0.0 | 0.0 | 0.4 | 0.0 | 0.0 | 0.0 | 0.0 |
| | Erysipelotrichaceae | 0.0 | 11.4 | 21.5 | 24.8 | 9.6 | 6.0 | 15.0 | 16.3 | 3.8 | 4.8 | 18.7 | 13.0 |
| | Lachnospiraceae | 8.2 | 0.9 | 0.0 | 0.5 | 0.0 | 0.7 | 0.0 | 0.5 | 0.0 | 0.7 | 0.0 | 0.5 |
| | Lactobacillaceae | 0.0 | 0.0 | 0.0 | 0.0 | 0.0 | 0.0 | 0.0 | 0.0 | 0.0 | 0.0 | 0.0 | 0.0 |
| | Paenibacillaceae | 0.0 | 0.1 | 1.0 | 2.0 | 0.0 | 0.3 | 0.4 | 1.2 | 0.0 | 0.1 | 0.3 | 2.7 |
| | Ruminococcaceae | 0.0 | 1.3 | 0.0 | 1.2 | 0.0 | 0.5 | 0.0 | 0.8 | 0.0 | 0.5 | 0.0 | 0.6 |
| | Streptococcaceae | 58.3 | 48.1 | 30.9 | 26.5 | 46.5 | 53.3 | 24.8 | 36.2 | 67.0 | 61.0 | 21.8 | 34.1 |
| | Veillonellaceae | 0.0 | 0.1 | 0.1 | 0.3 | 0.0 | 0.0 | 0.3 | 0.2 | 0.0 | 0.1 | 0.1 | 0.1 |
| Proteobacteria | Burkholderiaceae | 0.2 | 0.2 | 0.8 | 0.4 | 0.0 | 0.0 | 0.4 | 0.5 | 0.0 | 0.0 | 0.5 | 0.2 |
| | Desulfovibrionaceae | 0.0 | 0.0 | 0.0 | 0.0 | 0.0 | 0.0 | 0.0 | 0.0 | 0.0 | 0.0 | 0.0 | 0.0 |
| | Enterobacteriaceae | 0.0 | 0.0 | 0.3 | 0.4 | 0.0 | 0.3 | 0.4 | 0.5 | 0.0 | 0.1 | 0.3 | 0.3 |
| | Pseudomonadaceae | 0.0 | 1.3 | 0.3 | 0.4 | 0.0 | 0.5 | 0.8 | 0.3 | 0.0 | 0.5 | 0.2 | 0.1 |
| | Uncultured | 0.0 | 0.0 | 0.0 | 0.1 | 0.1 | 0.2 | 0.1 | 0.0 | 0.0 | 0.1 | 0.0 | 0.0 |
| | Xanthomonadaceae | 0.2 | 0.1 | 0.0 | 0.0 | 0.0 | 0.1 | 0.0 | 0.0 | 0.1 | 0.1 | 0.0 | 0.0 |
| Synergistetes | Synergistaceae | 0.0 | 0.0 | 0.0 | 0.0 | 0.0 | 0.0 | 3.6 | 5.3 | 0.0 | 0.3 | 3.8 | 6.8 |
| Verrucomicrobia | Akkermansiaceae | 0.0 | 0.0 | 3.0 | 1.6 | 0.0 | 0.0 | 8.9 | 4.5 | 0.0 | 0.0 | 0.8 | 1.3 |

Figure 6

| Phylum | Family | Mucosal layer | | | | | | | | | | | |
|---|---|---|---|---|---|---|---|---|---|---|---|---|---|
| | | Donor A | | | | Donor B | | | | Donor C | | | |
| | | Proximal colon | | Distal colon | | Proximal colon | | Distal colon | | Proximal colon | | Distal colon | |
| | | C | TR | C | TR | C | TR | C | TR | C | TR | C | TR |
| Actinobacteria | Bifidobacteriaceae | 31.0 | 31.1 | 17.2 | 21.8 | 36.1 | 23.3 | 12.4 | 30.1 | 33.8 | 35.6 | 22.1 | 26.4 |
| | Coriobacteriaceae | 0.3 | 0.2 | 0.3 | 1.9 | 1.2 | 1.1 | 1.3 | 1.1 | 0.3 | 1.0 | 1.1 | 1.7 |
| | Eggerthellaceae | 0.0 | 0.0 | 0.8 | 0.4 | 0.0 | 0.0 | 0.2 | 0.1 | 0.0 | 0.0 | 0.7 | 0.2 |
| | Microbacteriaceae | 0.6 | 1.3 | 0.4 | 1.2 | 3.1 | 1.4 | 0.2 | 0.5 | 0.4 | 1.1 | 0.2 | 0.4 |
| Bacteroidetes | Bacteroidaceae | 8.4 | 8.1 | 11.7 | 10.8 | 2.0 | 6.1 | 11.7 | 8.6 | 9.6 | 4.3 | 18.5 | 13.2 |
| | Barnesiellaceae | 0.0 | 0.0 | 0.0 | 0.1 | 0.0 | 0.0 | 0.0 | 0.0 | 0.0 | 0.0 | 0.0 | 0.2 |
| | Marinifilaceae | 0.0 | 0.1 | 0.4 | 0.3 | 0.0 | 0.0 | 0.3 | 0.3 | 0.0 | 0.1 | 0.3 | 0.4 |
| | Prevotellaceae | 0.0 | 0.0 | 0.0 | 0.0 | 0.0 | 0.0 | 0.1 | 0.0 | 0.0 | 0.0 | 0.2 | 0.0 |
| | Rikenellaceae | 0.0 | 0.0 | 1.1 | 1.7 | 0.0 | 0.1 | 2.1 | 1.2 | 0.0 | 0.0 | 1.0 | 2.0 |
| | Tannerellaceae | 1.9 | 1.9 | 1.5 | 2.2 | 0.0 | 1.2 | 3.5 | 2.3 | 0.0 | 0.6 | 2.1 | 2.6 |
| Firmicutes | Acidaminococcaceae | 8.6 | 6.4 | 10.4 | 11.8 | 6.6 | 7.4 | 8.8 | 5.0 | 6.0 | 3.9 | 9.6 | 5.5 |
| | Clostridiaceae | 0.1 | 0.0 | 0.7 | 0.6 | 0.0 | 0.0 | 0.5 | 1.3 | 0.0 | 0.0 | 0.7 | 1.2 |
| | Enterococcaceae | 2.3 | 9.9 | 4.9 | 4.5 | 6.2 | 4.3 | 2.6 | 2.0 | 2.6 | 12.5 | 1.7 | 2.1 |
| | Erysipelotrichaceae | 0.0 | 0.0 | 0.3 | 0.3 | 0.0 | 0.0 | 0.5 | 2.2 | 0.0 | 0.0 | 0.8 | 0.2 |
| | Lachnospiraceae | 14.7 | 11.1 | 28.0 | 21.1 | 11.0 | 7.5 | 22.1 | 18.0 | 19.3 | 5.1 | 20.2 | 14.2 |
| | Lactobacillaceae | 0.0 | 0.2 | 0.0 | 0.6 | 0.0 | 0.2 | 0.0 | 0.4 | 0.0 | 0.2 | 0.0 | 0.5 |
| | Paenibacillaceae | 0.0 | 0.1 | 0.0 | 2.3 | 0.0 | 0.3 | 0.0 | 0.0 | 0.0 | 0.0 | 0.0 | 0.0 |
| | Ruminococcaceae | 0.1 | 0.2 | 5.1 | 3.4 | 0.0 | 1.0 | 2.7 | 2.7 | 0.0 | 1.5 | 3.9 | 3.7 |
| | Streptococcaceae | 0.0 | 0.2 | 0.0 | 1.1 | 0.0 | 0.2 | 0.0 | 0.3 | 0.0 | 0.2 | 0.0 | 0.3 |
| | Veillonellaceae | 28.5 | 27.6 | 10.4 | 8.6 | 33.5 | 43.2 | 12.0 | 5.1 | 27.2 | 31.3 | 20.2 | 8.1 |
| | Burkholderiaceae | 0.4 | 0.4 | 1.6 | 3.1 | 0.1 | 0.4 | 2.4 | 1.1 | 0.4 | 0.4 | 4.1 | 1.3 |
| Proteobacteria | Desulfovibrionaceae | 3.0 | 1.1 | 1.8 | 0.6 | 0.1 | 1.0 | 1.1 | 1.0 | 0.2 | 0.0 | 1.9 | 1.0 |
| | Enterobacteriaceae | 0.0 | 0.0 | 0.1 | 0.1 | 0.0 | 0.2 | 0.0 | 0.1 | 0.1 | 0.1 | 0.9 | 0.2 |
| | Pseudomonadaceae | 0.0 | 0.0 | 0.0 | 0.0 | 0.0 | 0.1 | 0.0 | 0.0 | 0.0 | 0.0 | 0.2 | 0.0 |
| | Uncultured | 0.0 | 0.0 | 1.8 | 0.5 | 0.0 | 0.3 | 1.1 | 0.5 | 0.0 | 0.2 | 0.4 | 0.4 |
| | Xanthomonadaceae | 0.0 | 0.0 | 0.0 | 0.0 | 0.0 | 0.1 | 0.0 | 0.0 | 0.0 | 0.1 | 0.0 | 0.1 |
| Synergistetes | Synergistaceae | 0.0 | 0.0 | 0.0 | 0.4 | 0.0 | 0.3 | 9.4 | 15.2 | 0.0 | 2.0 | 8.1 | 13.3 |
| Verrucomicrobia | Akkermansiaceae | 0.0 | 0.0 | 0.7 | 0.4 | 0.2 | 0.2 | 4.3 | 0.5 | 0.0 | 0.0 | 0.7 | 0.1 |

Figure 7

| OTU | Closely related genus | Closely related species | Lumen Donor D | Lumen Donor E | Lumen Donor F | Liver cirrhosis T-test | Donor D | Donor E | Mucus Donor F | T-test |
|---|---|---|---|---|---|---|---|---|---|---|
| 1 | Escherichia-Shigella(100) | E. coli | -0.5% | -12.5% | -10.9% | 0.024 | 0.0% | 1.9% | -2.1% | 0.720 |
| 2 | Bacteroides(100) | B. fragilis | -0.1% | -9.9% | 1.7% | 0.155 | -2.2% | -21.2% | -9.0% | 0.006 |
| 3 | Bacteroides(100) | B. thetaiotaomicron | -0.9% | 0.0% | -6.3% | 0.041 | 0.3% | 0.0% | -1.6% | 0.252 |
| 4 | Bacteroides(100) | B. dorei | -2.5% | -2.5% | -3.3% | 0.000 | 0.1% | 0.4% | -0.7% | 0.728 |
| 5 | Bifidobacterium(100) | B. longum | 0.4% | 0.4% | 1.5% | 0.001 | -0.4% | 5.3% | 2.0% | 0.028 |
| 6 | Akkermansia(100) | A. muciniphila | -6.2% | -1.0% | 0.0% | 0.065 | -4.3% | 0.0% | 0.0% | 0.171 |
| 7 | Veillonella(100) | V. parvula/dispar | 18.0% | 1.9% | -1.3% | 0.082 | 12.9% | -0.4% | -4.7% | 0.357 |
| 8 | Clostridium_sensu_stricto(100) | C. tertium | 0.0% | -0.5% | -1.5% | 0.033 | 0.2% | -16.9% | -29.5% | 0.008 |
| 9 | Bifidobacterium(100) | B. bifidum | 0.0% | -0.2% | 0.0% | 0.134 | 0.0% | 10.6% | 0.0% | 0.125 |
| 10 | Bacteroides(100) | B. uniformis | 1.9% | 5.8% | -0.3% | 0.061 | -0.3% | 0.3% | 0.0% | 0.974 |
| 11 | Clostridium XIVa (99) | unclear | 0.0% | 0.0% | 2.0% | 0.088 | 3.1% | 0.0% | 0.9% | 0.033 |
| 12 | Clostridium XIVa(100) | unclear | -0.4% | -0.1% | -0.9% | 0.036 | 2.7% | 4.5% | 0.1% | 0.004 |
| 15 | Bifidobacterium(100) | B. pseudocatenulatum | 0.2% | 3.2% | 0.7% | 0.086 | 0.0% | 2.9% | 0.0% | 0.093 |
| 16 | Collinsella(100) | C. aerofaciens | 0.1% | 0.1% | 0.0% | 0.138 | 0.1% | 2.0% | 0.1% | 0.097 |
| 17 | Lactococcus(100) | L. garvieae | -5.8% | 0.0% | 0.0% | 0.117 | -3.4% | 0.0% | 0.0% | 0.107 |
| 18 | Clostridium XIVa(100) | C. symbiosum | -1.3% | -1.1% | -0.3% | 0.031 | -0.1% | 0.0% | 0.0% | 0.892 |
| 23 | Bacteroides(100) | B. thetaiotaomicron | -4.1% | -0.9% | -0.1% | 0.065 | -2.4% | 2.1% | 0.0% | 0.127 |
| 28 | Veillonella(100) | unclear | 0.0% | 17.7% | 2.6% | 0.029 | 0.0% | 0.4% | -0.1% | 0.229 |
| 30 | Bifidobacterium(100) | B. adolescentis | 1.9% | 0.0% | 4.8% | 0.034 | 0.2% | 0.0% | 0.1% | 0.030 |
| 31 | Streptococcus(100) | S. pasteurianus/macedonicus/gallolyticus | 0.5% | 0.0% | 13.2% | 0.087 | 0.1% | 0.0% | 4.7% | 0.207 |
| 33 | Parabacteroides(100) | P. merdae | 0.0% | 0.0% | -2.8% | 0.104 | -0.7% | 0.0% | -8.4% | 0.059 |
| 39 | Prevotella(100) | P. copri | 0.0% | 0.0% | 0.0% | 0.110 | 0.0% | 0.0% | 0.9% | 0.294 |
| 40 | Holdemanella(100) | H. biformis | 0.5% | 0.0% | 2.8% | 0.096 | 0.2% | 0.0% | 15.4% | 0.076 |
| 41 | Succinivibrio(100) | S. dextrinosolvens | 0.0% | 0.0% | 0.0% | 0.215 | 0.1% | 0.0% | 23.1% | 0.082 |
| 54 | Megasphaera(100) | M. elsdenii | 0.3% | 1.1% | 2.3% | 0.147 | 0.0% | 0.0% | 2.7% | 0.112 |

Figure 12

| Phylum | Family | Liver cirrhosis | | | | | | | |
|---|---|---|---|---|---|---|---|---|---|
| | | Lumen | | | | Mucus | | | |
| | | Donor D | Donor E | Donor F | T-test | Donor D | Donor E | Donor F | T-test |
| Actinobacteria | Atopobiaceae | 0,0% | 0,0% | 0,1% | 0,138 | 0,0% | 0,0% | 0,1% | 0,100 |
| | Bifidobacteriaceae | 2,8% | 4,6% | 5,4% | 0,000 | 0,5% | 23,2% | 1,2% | 0,052 |
| | Coriobacteriaceae | 0,0% | -0,1% | 0,6% | 0,129 | 0,1% | 2,6% | 0,1% | 0,095 |
| | Eggerthellaceae | 0,0% | -0,3% | -0,1% | 0,042 | 0,0% | 0,0% | 0,0% | 0,647 |
| | Propionibacteriaceae | 0,0% | 0,0% | 0,0% | 0,744 | 0,0% | 0,0% | 0,0% | 0,347 |
| Bacteroidetes | Bacteroidaceae | -6,9% | -7,3% | -10,6% | 0,000 | -8,7% | -20,6% | -13,0% | 0,000 |
| | Bacteroidales_unclassified | 0,0% | 0,0% | 0,0% | 0,532 | 0,0% | 0,0% | 0,0% | 0,030 |
| | Bacteroidia_unclassified | 0,0% | 0,0% | 0,0% | NA | 0,0% | 0,0% | 0,0% | NA |
| | Marinifilaceae | 0,1% | -0,2% | 0,0% | 0,448 | 0,0% | 0,0% | 0,0% | 0,727 |
| | Muribaculaceae | 0,0% | 0,0% | 0,0% | NA | 0,0% | 0,0% | 0,0% | NA |
| | Prevotellaceae | 0,0% | 0,0% | 0,0% | 0,106 | 0,0% | 0,0% | 1,0% | 0,293 |
| | Rikenellaceae | 0,1% | -0,4% | 0,0% | 0,221 | -0,1% | 0,1% | 0,0% | 0,874 |
| | Tannerellaceae | -0,2% | 1,1% | -3,2% | 0,311 | -0,8% | 0,4% | -8,5% | 0,072 |
| Firmicutes | Acidaminococcaceae | -1,5% | 0,0% | -4,4% | 0,086 | -3,9% | 0,0% | -0,8% | 0,050 |
| | Bacillaceae | 0,0% | 0,0% | 0,0% | 0,467 | 0,0% | 0,0% | 0,0% | NA |
| | Christensenellaceae | 0,0% | 0,0% | 0,0% | 0,100 | 0,0% | 0,0% | 0,0% | NA |
| | Clostridiaceae_1 | 0,0% | -0,6% | -1,7% | 0,023 | 0,2% | -14,8% | -26,7% | 0,000 |
| | Clostridiales_unclassified | 0,0% | 0,0% | 0,0% | 0,898 | 0,0% | 0,0% | 0,0% | NA |
| | Enterococcaceae | -0,8% | -1,5% | -0,3% | 0,001 | -6,2% | 0,1% | -0,3% | 0,071 |
| | Erysipelotrichaceae | 0,1% | 0,0% | 3,3% | 0,080 | 0,7% | 0,2% | 10,2% | 0,073 |
| | Eubacteriaceae | 0,0% | 0,0% | 0,0% | 0,470 | 0,0% | 0,0% | 0,0% | NA |
| | Family_XI | 0,0% | 0,0% | 0,0% | 0,064 | 0,0% | 0,0% | 0,0% | 0,069 |
| | Family_XIII | 0,0% | 0,0% | 0,0% | 0,064 | 0,0% | 0,0% | 0,0% | 0,347 |
| | Lachnospiraceae | -0,9% | 1,2% | -0,9% | 0,743 | 18,6% | 4,0% | 3,8% | 0,010 |
| | Lactobacillaceae | 9,7% | 6,2% | 3,5% | 0,000 | 1,5% | 1,2% | 1,1% | 0,000 |
| | Paenibacillaceae | 0,0% | 0,0% | 0,0% | NA | 0,0% | 0,0% | 0,0% | NA |
| | Peptostreptococcaceae | 0,0% | 0,0% | 0,0% | 0,086 | 0,0% | 0,0% | 0,0% | 0,678 |
| | Ruminococcaceae | 0,1% | -0,1% | 0,1% | 0,117 | 0,0% | 0,5% | 0,2% | 0,071 |
| | Streptococcaceae | -5,7% | 0,0% | 14,9% | 0,360 | -4,4% | 0,2% | 6,3% | 0,684 |
| | Veillonellaceae | 18,3% | 13,7% | 1,1% | 0,001 | 13,7% | 0,2% | -1,9% | 0,143 |
| Fusobacteria | Fusobacteriaceae | 0,0% | 0,0% | 0,0% | 0,137 | 0,0% | 0,0% | 0,0% | 0,065 |
| Proteobacteria | Aeromonadaceae | 0,0% | 0,0% | 0,0% | NA | 0,0% | 0,0% | -0,1% | 0,082 |
| | Burkholderiaceae | 0,1% | 0,0% | 0,1% | 0,074 | 0,0% | 0,1% | 0,0% | 0,259 |
| | Desulfovibrionaceae | -0,1% | 0,0% | 0,1% | 0,990 | 0,0% | 0,0% | 0,0% | 0,484 |
| | Enterobacteriaceae | -8,0% | -15,3% | -11,1% | 0,000 | -4,8% | 2,6% | -2,1% | 0,345 |
| | Succinivibrionaceae | 0,0% | 0,0% | 0,0% | 0,210 | 0,1% | 0,0% | 23,1% | 0,082 |
| Synergistetes | Synergistaceae | 0,0% | 0,0% | 0,0% | 0,347 | 0,0% | 0,0% | 0,0% | NA |
| Verrucomicrobia | Akkermansiaceae | -6,3% | -1,0% | 0,0% | 0,044 | -4,3% | 0,0% | 0,0% | 0,173 |

Figure 13

| OTU | Closely related genus | Closely related species | Lumen |  |  |  | Parkinson |  |  |  | Mucus |  |
|---|---|---|---|---|---|---|---|---|---|---|---|---|
|  |  |  | Donor G | Donor H | Donor I | T-test | Donor G | Donor H | Donor I | T-test |  |  |
| 1 | Escherichia-Shigella(100) | E. coli | -0.6% | 0.2% | -0.7% | 0.734 | 0.3% | -3.1% | 10.2% | 0.273 | | |
| 2 | Bacteroides(100) | B. fragilis | 0.0% | 0.1% | -3.0% | 0.094 | 0.0% | 1.6% | -17.3% | 0.125 | | |
| 3 | Bacteroides(100) | B. thetaiotaomicron | -1.5% | 8.5% | -9.6% | 0.760 | 0.1% | 12.7% | -0.7% | 0.108 | | |
| 4 | Bacteroides(100) | B. dorei | 0.0% | -7.6% | -1.9% | 0.036 | 0.3% | -13.0% | -0.3% | 0.096 | | |
| 5 | Bifidobacterium(100) | B. longum | 2.3% | 0.1% | 1.0% | 0.008 | 10.5% | 2.3% | 8.3% | 0.001 | | |
| 6 | Akkermansia(100) | A. muciniphila | -3.9% | -25.1% | -0.2% | 0.049 | -5.4% | -3.5% | 0.0% | 0.062 | | |
| 7 | Veillonella(100) | V. parvula/dispar | 10.1% | 9.2% | 2.7% | 0.003 | 0.7% | 5.7% | 0.3% | 0.046 | | |
| 8 | Clostridium_sensu_stricto(100) | C. tertium | -0.4% | 0.0% | -1.9% | 0.027 | -4.7% | -3.3% | -12.2% | 0.003 | | |
| 10 | Bacteroides(100) | B. uniformis | 3.5% | 0.0% | -0.3% | 0.142 | 0.1% | -0.1% | -0.1% | 0.537 | | |
| 11 | Clostridium XIVa (99) | unclear | 0.0% | 2.9% | 0.7% | 0.026 | 0.7% | 23.4% | 3.4% | 0.036 | | |
| 12 | Clostridium XIVa(100) | unclear | 0.1% | 0.5% | 1.4% | 0.015 | 0.1% | 0.8% | 2.2% | 0.017 | | |
| 13 | Roseburia(100) | unclear | 0.0% | 0.0% | 0.3% | 0.112 | 0.0% | 0.0% | 0.0% | 0.186 | | |
| 17 | Lactococcus(100) | L. garvieae | 3.8% | 0.0% | 0.0% | 0.098 | 0.3% | 1.1% | -0.7% | 0.116 | | |
| 19 | Bacteroides(100) | B. caccae | -2.6% | 0.3% | -1.0% | 0.034 | -13.4% | 0.7% | 0.3% | 0.103 | | |
| 20 | Lactobacillus(100) | L. plantarum | 6.8% | 3.4% | 3.1% | 0.000 | 0.4% | 0.3% | 0.3% | 0.000 | | |
| 21 | Lactobacillus(100) | L. rhamnosus | 1.4% | 6.3% | 7.8% | 0.001 | 0.1% | 0.3% | 0.3% | 0.000 | | |
| 22 | Enterococcus(99) | E. faecium | -0.4% | -1.1% | 3.0% | 0.429 | -0.1% | -3.5% | 1.2% | 0.341 | | |
| 25 | Clostridium_sensu_stricto_1(100) | C. butyricum | 0.3% | 0.0% | 0.0% | 0.091 | 1.0% | -22.2% | 0.0% | 0.169 | | |
| 26 | Phascolarctobacterium(100) | P. faecium | 0.0% | -1.2% | -3.0% | 0.013 | 0.0% | -0.7% | -2.0% | 0.034 | | |
| 29 | Faecalibacterium(100) | F. prausnitzii | 0.0% | 0.0% | 0.0% | 0.051 | 0.0% | 0.0% | 0.0% | 0.085 | | |
| 43 | Unclassified Porphyromonadaceae(91) | unclear | 0.0% | -2.0% | -0.1% | 0.125 | 0.0% | -5.8% | 0.0% | 0.251 | | |
| 46 | Citrobacter(77) | C. freundii | -0.1% | -0.1% | 0.0% | 0.057 | -0.1% | -0.2% | 0.0% | 0.077 | | |
| 48 | Romboutsia(100) | unclear | -0.1% | 0.4% | 0.0% | 0.008 | 0.3% | -0.2% | 0.0% | 0.171 | | |
| 49 | Parabacteroides(100) | P. goldsteinii | -0.6% | 0.4% | 0.0% | 0.809 | -2.0% | 0.0% | 0.0% | 0.072 | | |
| 53 | Lactococcus(100) | L. lactis | 0.0% | 1.9% | 0.0% | 0.148 | 0.0% | 0.0% | 0.0% | 0.757 | | |

Figure 14

| Phylum | Family | Parkinson | | | | | | | |
|---|---|---|---|---|---|---|---|---|---|
| | | Lumen | | | | Mucus | | | |
| | | Donor G | Donor H | Donor I | T-test | Donor G | Donor H | Donor I | T-test |
| Actinobacteria | Atopobiaceae | 0,0% | 0,0% | 0,0% | 0,667 | 0,0% | 0,0% | 0,0% | NA |
| | Bifidobacteriaceae | 4,7% | 0,2% | 3,4% | 0,004 | 12,6% | 2,9% | 10,2% | 0,022 |
| | Coriobacteriaceae | 0,1% | 0,0% | 0,0% | 0,074 | 0,3% | 0,0% | 0,0% | 0,073 |
| | Eggerthellaceae | 0,1% | 0,0% | -0,1% | 0,745 | 0,0% | 0,0% | 0,0% | 0,850 |
| | Propionibacteriaceae | 0,0% | 0,0% | 0,0% | 0,187 | 0,0% | 0,0% | 0,0% | 0,295 |
| Bacteroidetes | Bacteroidaceae | -1,3% | 1,5% | -17,2% | 0,115 | -13,8% | 1,2% | -15,2% | 0,057 |
| | Bacteroidales_unclassified | 0,0% | 0,0% | 0,0% | 0,852 | 0,1% | 0,0% | 0,0% | 0,201 |
| | Bacteroidia_unclassified | 0,0% | 0,0% | 0,0% | 0,456 | 0,0% | 0,0% | 0,0% | 0,920 |
| | Marinifilaceae | 0,0% | 0,0% | -0,2% | 0,083 | 0,0% | -0,2% | 0,0% | 0,061 |
| | Muribaculaceae | 0,0% | 0,0% | 0,0% | 0,121 | 0,0% | 0,0% | 0,0% | 0,251 |
| | Prevotellaceae | 0,0% | 0,0% | 0,0% | 0,099 | 0,0% | 0,0% | 0,0% | 0,099 |
| | Rikenellaceae | 0,4% | 0,0% | 0,0% | 0,084 | 0,1% | 0,0% | 0,0% | 0,321 |
| | Tannerellaceae | -1,4% | 1,1% | -0,4% | 0,650 | -4,2% | 0,6% | 0,1% | 0,227 |
| Firmicutes | Acidaminococcaceae | -0,1% | -1,2% | -3,0% | 0,012 | -0,1% | -0,7% | -2,1% | 0,023 |
| | Bacillaceae | 0,0% | 0,0% | 0,0% | NA | 0,0% | 0,0% | 0,0% | 0,347 |
| | Christensenellaceae | 0,0% | 0,0% | 0,0% | 0,307 | 0,0% | 0,0% | 0,0% | 0,078 |
| | Clostridiaceae_1 | -6,9% | -0,4% | -1,9% | 0,018 | 1,3% | -25,7% | -12,2% | 0,019 |
| | Clostridiales_unclassified | 0,0% | 0,0% | 0,2% | 0,303 | 0,0% | 0,0% | -0,3% | 0,188 |
| | Enterococcaceae | -22,7% | -2,1% | 3,0% | 0,105 | -3,6% | -4,0% | 1,2% | 0,091 |
| | Erysipelotrichaceae | 0,8% | 0,0% | 0,0% | 0,111 | 5,5% | 0,0% | 0,3% | 0,062 |
| | Eubacteriaceae | 0,0% | 1,7% | 2,5% | 0,019 | 0,0% | 0,2% | 0,1% | 0,016 |
| | Family_XI | 0,3% | -0,2% | -0,1% | 0,872 | 0,0% | -0,1% | 0,0% | 0,124 |
| | Family_XIII | 0,0% | 0,1% | 0,0% | 0,146 | 0,0% | 0,0% | 0,0% | 0,164 |
| | Lachnospiraceae | 0,7% | 4,3% | 2,4% | 0,007 | 5,5% | 27,3% | 10,0% | 0,003 |
| | Lactobacillaceae | 7,5% | 7,2% | 10,3% | 0,000 | 0,6% | 0,9% | 0,7% | 0,000 |
| | Paenibacillaceae | 0,0% | 0,0% | 0,0% | NA | 0,0% | 0,0% | 0,0% | NA |
| | Peptostreptococcaceae | -0,6% | -0,1% | -1,1% | 0,010 | -0,6% | -0,1% | -0,3% | 0,014 |
| | Ruminococcaceae | 0,1% | 0,0% | 0,1% | 0,079 | 0,2% | 0,1% | 0,0% | 0,002 |
| | Streptococcaceae | 3,9% | 4,2% | 0,0% | 0,008 | 0,9% | 2,6% | 0,1% | 0,016 |
| | Veillonellaceae | 20,1% | 12,5% | 3,4% | 0,001 | 0,8% | 7,1% | 0,4% | 0,050 |
| Fusobacteria | Fusobacteriaceae | -1,1% | 0,0% | 0,0% | 0,087 | -0,2% | 0,0% | 0,0% | 0,093 |
| Proteobacteria | Aeromonadaceae | 0,0% | 0,0% | 0,0% | NA | 0,0% | 0,0% | 0,0% | NA |
| | Burkholderiaceae | 0,0% | 0,0% | -0,2% | 0,098 | 0,0% | 0,0% | -0,1% | 0,135 |
| | Desulfovibrionaceae | -0,1% | 0,0% | 0,0% | 0,359 | 0,0% | 0,0% | 0,0% | 0,444 |
| | Enterobacteriaceae | -0,6% | -3,5% | -1,0% | 0,155 | 0,2% | -9,3% | 10,3% | 0,850 |
| | Succinivibrionaceae | 0,0% | 0,0% | 0,0% | NA | 0,0% | 0,0% | 0,0% | 0,347 |
| Synergistetes | Synergistaceae | -0,6% | -0,8% | -0,8% | 0,000 | 0,0% | -0,2% | 0,0% | 0,053 |
| Verrucomicrobia | Akkermansiaceae | -3,9% | -25,2% | -0,2% | 0,049 | -5,4% | -3,6% | 0,0% | 0,062 |

Figure 15

| OTU | Closely related genus | Closely related species | Lumen Donor A | Lumen Donor B | Lumen Donor C | T-test | IBD Donor A | IBD Donor B | IBD Donor C | T-test |
|---|---|---|---|---|---|---|---|---|---|---|
| 1 | Escherichia-Shigella(100) | E. coli | -7.4% | -2.5% | -1.9% | 0.003 | 3.4% | 4.5% | -0.1% | 0.039 |
| 2 | Bacteroides(100) | B. fragilis | 5.0% | 7.8% | -0.5% | 0.014 | -10.1% | -1.1% | -2.1% | 0.064 |
| 3 | Bacteroides(100) | B. thetaiotaomicron | -6.6% | 3.3% | 0.0% | 0.513 | -1.1% | -2.1% | 0.0% | 0.062 |
| 4 | Bacteroides(100) | B. dorei | -1.6% | 0.0% | -3.1% | 0.161 | 0.1% | 0.0% | -2.6% | 0.098 |
| 5 | Bifidobacterium(100) | B. longum | 0.0% | 0.0% | 14.1% | 0.086 | 0.0% | 0.0% | -3.7% | 0.730 |
| 6 | Akkermansia(100) | A. muciniphila | 0.0% | -11.6% | 0.0% | 0.102 | 0.0% | -1.6% | 0.0% | 0.104 |
| 9 | Bifidobacterium(100) | B. bifidum | 0.0% | 0.0% | -1.6% | 0.081 | 0.0% | 0.0% | 0.3% | 0.972 |
| 10 | Bacteroides(100) | B. uniformis | -0.2% | -0.2% | 2.0% | 0.453 | 0.0% | 0.0% | -0.3% | 0.456 |
| 11 | Clostridium XIVa (99) | unclear | -1.7% | -0.1% | -2.7% | 0.013 | 0.2% | -3.7% | -1.0% | 0.116 |
| 12 | Clostridium XIVa(100) | unclear | -2.5% | -0.4% | -2.6% | 0.004 | -4.9% | -4.3% | -0.1% | 0.004 |
| 13 | Roseburia(100) | unclear | 0.1% | 0.3% | -0.2% | 0.587 | 6.9% | 18.5% | 0.0% | 0.020 |
| 16 | Collinsella(100) | C. aerofaciens | 0.0% | -0.1% | 0.0% | 0.094 | 0.0% | -9.9% | 0.0% | 0.087 |
| 18 | Clostridium XIVa(100) | C. symbiosum | -5.1% | -0.8% | -7.9% | 0.005 | -0.5% | -0.7% | -0.2% | 0.032 |
| 20 | Lactobacillus(100) | L. plantarum | 3.0% | 7.4% | 13.6% | 0.001 | 0.4% | 2.1% | 6.1% | 0.035 |
| 21 | Lactobacillus(100) | L. rhamnosus | 1.7% | 5.5% | 13.2% | 0.003 | 0.1% | 0.5% | 0.8% | 0.013 |
| 24 | Ruminococcus(100) | unclear | -1.8% | 0.0% | 0.0% | 0.084 | -13.2% | -1.0% | 0.0% | 0.063 |
| 27 | Parabacteroides(100) | P. distasonis | -1.0% | 0.1% | 0.0% | 0.387 | 0.1% | 0.0% | 0.0% | 0.306 |
| 28 | Veillonella(100) | unclear | 15.3% | 0.0% | 8.4% | 0.082 | 1.2% | 0.0% | 0.0% | 0.075 |
| 32 | Blautia(100) | unclear | 4.1% | 0.0% | 4.0% | 0.062 | 10.8% | 0.0% | 0.5% | 0.070 |
| 42 | Lachnospiraceae incerae sedis(100) | unclear | 8.4% | 0.0% | 0.0% | 0.058 | 0.7% | 0.0% | 1.9% | 0.051 |
| 44 | Roseburia(100) | R. inulinivorans | 0.0% | 0.0% | 0.0% | 0.109 | 0.0% | 0.0% | 0.1% | 0.217 |
| 50 | Streptococcus(100) | S. salivarius | -0.2% | 0.1% | 0.0% | 0.239 | 0.1% | 0.0% | 0.0% | 0.169 |
| 51 | Clostridium XVIII(100) | C. ramosum | 0.0% | 5.5% | -7.8% | 0.108 | 0.0% | -0.5% | -0.7% | 0.013 |
| 56 | Bifidobacterium(100) | B. pseudolongum | 0.0% | 0.0% | 0.0% | 0.085 | 1.0% | 1.0% | 0.0% | 0.178 |
| 69 | Feniceella(100) | unclear | 0.0% | 0.0% | 0.0% | 0.347 | -0.1% | -7.1% | -3.7% | 0.076 |

Figure 16

| Phylum | Family | IBD Lumen | | | | Mucus | | | |
|---|---|---|---|---|---|---|---|---|---|
| | | Donor A | Donor B | Donor C | T-test | Donor A | Donor B | Donor C | T-test |
| Actinobacteria | Atopobiaceae | 0,0% | 0,0% | 0,0% | 0,347 | 0,0% | 0,0% | 0,0% | 0,157 |
| | Bifidobacteriaceae | 1,6% | 5,6% | 12,8% | 0,005 | 0,2% | 1,2% | -3,6% | 0,509 |
| | Coriobacteriaceae | -0,5% | -0,1% | 0,0% | 0,026 | -0,4% | -9,9% | 0,0% | 0,076 |
| | Eggerthellaceae | -0,3% | -0,5% | -1,0% | 0,001 | 0,0% | 0,8% | 0,0% | 0,053 |
| | Propionibacteriaceae | 0,0% | 0,0% | 0,0% | 0,347 | 0,0% | 0,0% | 0,0% | NA |
| Bacteroidetes | Bacteroidaceae | -7,0% | 12,0% | -4,5% | 0,968 | -11,7% | -3,7% | -9,9% | 0,004 |
| | Bacteroidales_unclassified | 0,0% | 0,0% | 0,0% | 0,370 | 0,0% | 0,0% | 0,0% | 0,506 |
| | Bacteroidia_unclassified | 0,0% | 0,0% | 0,0% | NA | 0,0% | 0,0% | 0,0% | NA |
| | Marinifilaceae | 0,0% | 0,0% | 0,0% | 0,003 | 0,0% | 0,0% | 0,0% | 0,053 |
| | Muribaculaceae | 0,0% | 0,0% | 0,0% | NA | 0,0% | 0,0% | 0,0% | NA |
| | Prevotellaceae | 0,0% | 0,0% | 0,0% | 0,106 | 0,0% | 0,0% | 0,0% | 0,380 |
| | Rikenellaceae | -0,2% | 0,0% | -0,1% | 0,016 | 0,0% | 0,0% | 0,0% | 0,931 |
| | Tannerellaceae | -1,2% | 0,0% | 0,0% | 0,391 | 0,1% | 0,0% | 0,0% | 0,365 |
| Firmicutes | Acidaminococcaceae | 0,0% | 0,0% | 0,0% | 0,188 | 0,0% | 0,0% | 0,0% | NA |
| | Bacillaceae | 0,0% | 0,0% | -0,1% | 0,109 | 0,0% | 0,0% | -1,4% | 0,085 |
| | Christensenellaceae | 0,0% | 0,0% | 0,0% | 0,169 | 0,0% | 0,0% | 0,0% | NA |
| | Clostridiaceae_1 | 0,0% | 0,0% | 0,0% | 0,650 | -1,1% | -6,9% | -3,7% | 0,050 |
| | Clostridiales_unclassified | 0,0% | 0,0% | 0,0% | 0,114 | 0,0% | 0,0% | 0,0% | 0,153 |
| | Enterococcaceae | -0,1% | -21,0% | 0,1% | 0,081 | 0,0% | -0,1% | 0,0% | 0,870 |
| | Erysipelotrichaceae | -0,4% | 0,1% | -7,8% | 0,091 | -0,1% | -0,5% | -0,8% | 0,004 |
| | Eubacteriaceae | 0,0% | 0,0% | 0,0% | 0,347 | 0,0% | 0,0% | 0,0% | NA |
| | Family XI | 0,0% | -0,3% | 0,0% | 0,119 | 0,0% | 0,0% | 0,0% | 0,119 |
| | Family XIII | 0,0% | 0,0% | 0,0% | 0,010 | 0,0% | 0,0% | 0,0% | 0,341 |
| | Lachnospiraceae | -5,9% | 1,7% | -13,8% | 0,055 | 7,6% | 11,8% | 11,4% | 0,004 |
| | Lactobacillaceae | 5,7% | 16,8% | 22,9% | 0,000 | 1,4% | 4,7% | 7,1% | 0,012 |
| | Paenibacillaceae | 0,0% | 0,0% | 0,0% | NA | 0,0% | -0,2% | -0,1% | 0,086 |
| | Peptostreptococcaceae | -5,7% | 0,0% | 0,0% | 0,084 | -0,2% | 0,1% | 0,1% | 0,837 |
| | Ruminococcaceae | -1,6% | -0,2% | -0,6% | 0,008 | -0,2% | 0,0% | 0,0% | 0,564 |
| | Streptococcaceae | 0,1% | 0,0% | -0,3% | 0,100 | 1,0% | 0,3% | 0,4% | 0,033 |
| | Veillonellaceae | 17,5% | 0,4% | 0,1% | 0,082 | 3,1% | 1,1% | 0,1% | 0,007 |
| Fusobacteria | Fusobacteriaceae | 0,0% | 0,0% | 0,0% | NA | 0,0% | 0,0% | 0,0% | NA |
| Proteobacteria | Aeromonadaceae | 0,0% | 0,0% | 0,0% | NA | 0,0% | 0,0% | 0,0% | NA |
| | Burkholderiaceae | 0,0% | -0,2% | -5,4% | 0,073 | 0,0% | 0,2% | 0,3% | 0,035 |
| | Desulfovibrionaceae | -0,1% | 0,0% | 0,0% | 0,101 | 0,0% | 0,0% | 0,0% | 0,347 |
| | Enterobacteriaceae | -7,8% | -2,6% | -1,9% | 0,003 | 1,3% | 4,3% | -0,1% | 0,031 |
| | Succinivibrionaceae | 0,0% | 0,0% | 0,0% | NA | 0,0% | 0,0% | 0,0% | NA |
| Synergistetes | Synergistaceae | 0,0% | 0,0% | 0,0% | NA | 0,0% | 0,0% | 0,0% | NA |
| Verrucomicrobia | Akkermansiaceae | 0,0% | -11,7% | 0,0% | 0,102 | 0,0% | -1,7% | 0,0% | 0,107 |

Figure 17

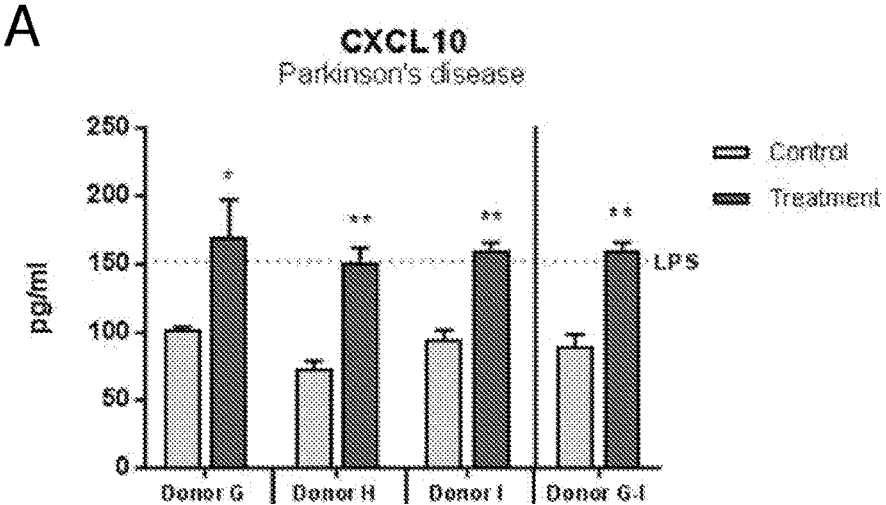
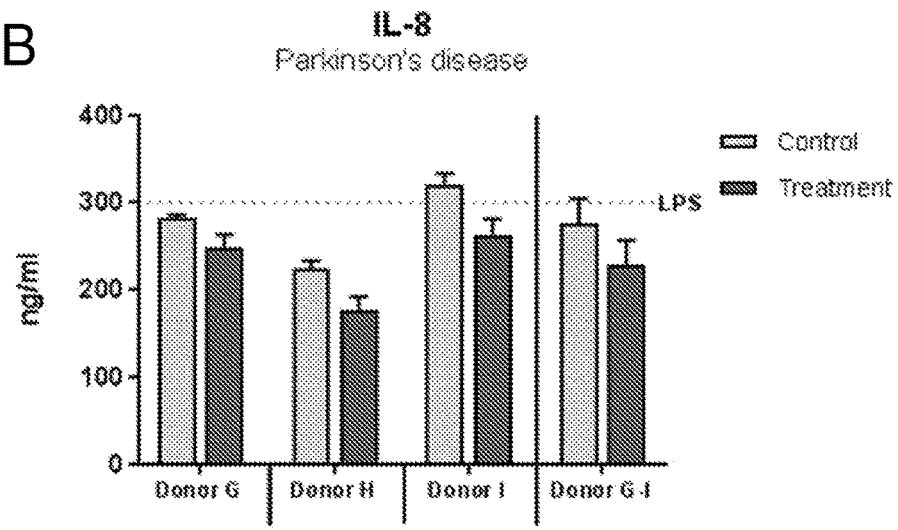
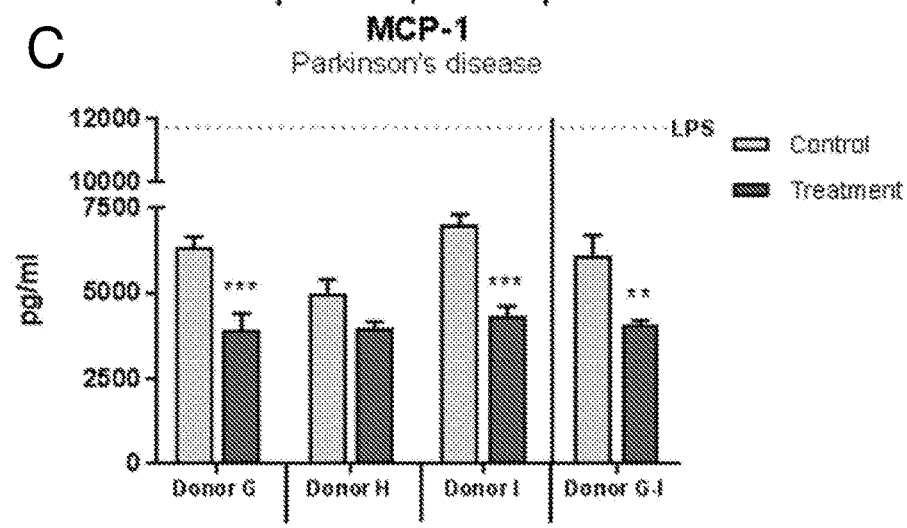
Figure 25

METHODS OF PROMOTING SCFA PRODUCTION BY GUT MICROBIOTA

FIELD OF INVENTION

The invention relates to methods for promoting SCFA production by gut microbiota by administering a liquid, water-based probiotic composition. The methods are particularly effective at promoting gut health. The invention further relates to methods of promoting intestinal barrier integrity, methods of promoting a tolerogenic gut phenotype, and methods of treating Parkinson's Disease.

BACKGROUND

Short chain fatty acids (SCFAs) play a variety of important roles in the human gut microenvironment, including acting as a food source for host epithelial and mucosal cells and regulating the local pH conditions. In addition, SCFAs act as food sources for bacteria of the microbiota, with complex interrelationships of SCFA production, metabolism and cross-feeding contributing to the overall composition and health of the gut microbiota and thus the gut itself.

SCFA production typically results from carbohydrate metabolism in the colon. The most abundantly produced SCFAs are acetate, propionate and butyrate. Acetate can be used as an energy source for the host and as a potential substrate for lipid synthesis in the body. Propionate reduces cholesterol and fatty acid synthesis in the liver, which is thought to have a beneficial effect on metabolic homeostasis. Acetate and propionate can also be used as an energy source by other gut bacteria, often being metabolised to produce butyrate.

Acetate, propionate and butyrate have also been reported to have a protective effect on diet-induced obesity. This is reported to be due to a loss of appetite following the production of gut hormones (in response to butyrate or propionate) or due to action on the central nervous system (in the case of acetate).

The possibility of health benefits such as these have led to an increase in consumer interest in products containing probiotic bacterial species and their potential to improve wellbeing. However, the challenging environment of the human digestive tract has meant probiotic supplements intended for oral administration often fail to deliver bacteria to the small intestine in a viable state. Accordingly, any feeling of improved health often reduces to a placebo effect. Further, the ability of probiotic species to influence established gut microbiota has not been proven. Instead, any probiotic bacteria that do survive transit through the digestive tract are present only in the luminal compartment of the gut for a short period of time, rather than colonising the gut mucosal compartment and affecting the established gut microbiota. This hypothesis may explain why many probiotics fail to demonstrate long term effects on gut health.

Parkinson's Disease is a degenerative neurological disorder characterised by motor system syndromes as well as a range of non-motor symptoms. The mean age of the population is increasing in a wide range of countries around the world, making degenerative disorders such as Parkinson's Disease ever more relevant. Current management of the condition is of limited efficacy and pharmacological therapies are associated with significant side effects. There is therefore a need for alternative means for treating Parkinson's Disease.

The present invention addresses these and other problems by providing a method of promoting SCFA production by gut microbiota, thereby promoting gut health, and providing a method of treating or preventing Parkinson's Disease.

SUMMARY OF INVENTION

The importance of the gut microbiota in influencing a person's general wellbeing is becoming ever more apparent. In healthy individuals, changes in gut microbiota have been linked with periods of stress, anxiety and depression, and may cause weight gain and variable responses to diet and pharmaceuticals. These changes may be in the composition of the gut microbiota, changes in its metabolic activity, or both.

For example, a person's gut microbiota may exhibit types and/or relative numbers of gut bacteria which are abnormal compared to a healthy gut, a state also known as "dysbiosis". An unhealthy gut may also be indicated by abnormal changes in SCFA production, which itself may be due to changes in composition of the gut microbiota.

SCFAs are thought to contribute to human health, for example by inhibiting pathogenic growth by lowering pH in the intestinal lumen and improving the ability of epithelial cells to defend against pathogenic *E. coli* infection. In addition, butyrate is a major energy source for host colonocytes and induces differentiation in these cells, which is thought to be related to a reduced risk of colon cancer. Butyrate and propionate have been reported to induce the differentiation of T-regulatory cells via inhibition of histone deacetylation.

In a subject exhibiting dysbiosis, the gut microbiota may be sufficiently imbalanced that the person's wellbeing suffers, even though they may not have any particular disease condition. Dysbiosis can lead to discomfort and an increased risk of infection. Dysbiosis has also been linked with risk of anxiety, stress, or depression in otherwise healthy individuals, as well as being associated with an increased risk of GI cancers such as colon carcinoma.

As well as impacting on the wellbeing of otherwise healthy individuals, impaired gut health is also often associated with certain disease conditions, even if it is not part of the disease symptoms per se. For example, abnormal gut microbiota has been reported for subjects having obesity, diabetes, and chronic fatigue syndrome.

Promoting a healthy gut microbiota can thus make an important contribution to a person's overall wellbeing and health, both when that person is otherwise healthy and also when that person is suffering from a disease or pathological condition.

As demonstrated herein, administration of a liquid, water-based probiotic composition comprising a population of probiotic bacteria is capable of influencing an established gut microbiota population so as to increase the levels of SCFA production, and is also shown to change the proportions of the bacterial taxa making up the gut microbiota.

Probiotic bacteria of the preparation administered according to the invention are shown to colonise and proliferate in the gut mucosal and luminal environment, where their interactions with the established bacterial populations cause the microbiota as a whole to rebalance. This rebalancing is indicated by increased SCFA production by the gut microbiota. It is further evidenced by the changes in the composition of the gut microbiota at the phylum and family taxonomic levels. This modification of the balance of the gut microbiota as a whole is indicative of improvement in the gut health following administration of the probiotic.

Because administration of the probiotic results in a rebalancing of the established microbiota, both in the lumen and especially in the mucosa, the benefits of the methods of the invention will be persistent and maintained. This is in contrast with the effect seen with many probiotics, where the inability to influence the gut microbiota as a whole means any effect is restricted to a transient effect on the luminal compartment, since the effect will only occur during the transit of the probiotic bacteria through the digestive tract.

Accordingly, in a first aspect is provided a method of promoting gastrointestinal health in a subject comprising administering a liquid, non-dairy-based probiotic composition comprising a population of lactic acid bacteria, wherein administration of the probiotic composition promotes production of one or more SCFAs by the subject's gut microbiota, thereby promoting intestinal health.

In a second aspect is provided a method of promoting production of one or more short chain fatty acids (SCFAs) by a subject's gut microbiota comprising administering to the subject a liquid, non-dairy-based probiotic composition comprising a population of lactic acid bacteria.

In a further aspect is provided a method of promoting growth of one or more bacterial phyla selected from Actinobacteria (e.g. Bifidobacteriaceae), Firmicutes (e.g. Veillonellaceae, Lachnospiraceae, Streptococcaceae, Eubacteriaceae, Ruminococcaceae, Erysipelotrichaceae), Proteobacteria (e.g. Enterobacteriaceae) in the gut microbiota of a subject, the method comprising administering to the subject a liquid, non-dairy probiotic preparation comprising a population of lactic acid bacteria.

In certain preferred embodiments, the growth is in the gut mucosal compartment. In certain preferred embodiments, the growth is in the gut luminal compartment. In certain preferred embodiments, the growth is in both the luminal and mucosal compartments.

In a preferred embodiment, the method promotes production of one or more SCFAs.

In a further aspect is provided a method of inhibiting growth of one or more bacterial phyla selected from Actinobacteria (e.g. Coriobacteriaceae, Eggerthellaceae), Bacteroidetes (e.g. Bacteroidaceae, Rikenellaceae, Lachnospiraceae, Ruminococcaceae), Firmicutes (e.g., Acidaminococcaceae, Enterococcaceae, Clostridiaceae, Peptostreptococcaceae), Proteobacteria (e.g. Enterobacteriaceae), Synergistetes (e.g. Synergistaceae) and Verrucomicrobio (e.g. Akkermansiaceae) in the gut microbiota of a subject, the method comprising administering to the subject a liquid, non-dairy probiotic preparation comprising a population of lactic acid bacteria.

In certain preferred embodiments, the growth is inhibited in the gut mucosal compartment. In certain preferred embodiments, the growth is inhibited in the gut luminal compartment. In certain preferred embodiments, the growth is inhibited in both the luminal and mucosal compartments.

In a preferred embodiment, the method promotes production of one or more SCFAs.

In certain preferred embodiments of all aspects of the invention, the methods promote production of one or more SCFAs selected from butyrate, propionate and acetate. In certain preferred embodiments, the method promotes production of butyrate.

SCFAs produced following administration of the probiotic preparation according to the invention can be considered to be "postbiotic" compounds, or simply "postbiotics". Postbiotics are health-associated compounds produced by the microbiota following administration of a probiotic. By promoting the production of health-linked SCFAs by the gut microbiota, administration of the probiotic preparation in accordance with the invention can be considered to have a "postbiotic" effect.

Accordingly, in certain embodiments, methods of the invention promote production of postbiotic compounds, such as SCFAs.

In a further aspect is provided a method of promoting intestinal barrier integrity in a subject, the method comprising administering to the subject a liquid, non-dairy probiotic preparation comprising a population of lactic acid bacteria, wherein administration of the probiotic preparation promotes said intestinal barrier integrity. In certain such embodiments, the method prevents or reduces loss of intestinal barrier integrity. In certain embodiments, the method promotes intestinal barrier repair.

In a further aspect is provided a method for promoting a tolerogenic gut phenotype in a subject, the method comprising administering to the subject a liquid, non-dairy probiotic preparation comprising a population of lactic acid bacteria, wherein administration of the probiotic preparation promotes said tolerogenic gut phenotype. In certain embodiments the method promotes production of anti-inflammatory molecules by intestinal epithelial cells. In certain embodiments the method reduces production of pro-inflammatory molecules by intestinal epithelial cells.

In certain preferred embodiments of methods of the invention, the method is a non-therapeutic method.

In certain preferred embodiments of methods of the invention the subject is a healthy individual.

In certain preferred embodiments of methods of the invention the subject is in a state of gastrointestinal dysbiosis.

In certain preferred embodiments, the subject is suffering from a disease or disorder. In certain preferred embodiments, the subject has a disease or disorder selected from Parkinson's Disease, liver cirrhosis, inflammatory bowel syndrome (IBD), *Clostridium difficile* infection, MRSA infection, *E. coli* infection, obesity, diabetes, and chronic fatigue syndrome. In certain preferred embodiments, the subject has Parkinson's Disease. In certain embodiments the subject has liver cirrhosis.

Parkinson's Disease is a degenerative neurological disorder characterised by motor system syndromes as well as a range of non-motor symptoms. As populations of some countries age, degenerative disorders such as Parkinson's Disease become ever more relevant. Current management is of limited efficacy and pharmacological therapies are associated with significant side effects. There is therefore a need for alternative means for treating Parkinson's Disease.

As reported herein, patients with Parkinson's Disease receiving a probiotic preparation according to the invention show an improvement in motor and non-motor symptoms. The data presented in the Examples further demonstrates that the probiotic preparation is able to promote a healthy gut phenotype in Parkinson's Disease, by reducing the loss of intestinal barrier integrity and the inflammatory gut phenotype exhibited by PD patients. Taken together, these data indicate that administration of the probiotic preparation will provide effective treatment of Parkinson's Disease patients.

Accordingly, in a further aspect is provided a method of treating or preventing Parkinson's Disease in a subject, the method comprising administering to the subject a liquid, non-dairy probiotic preparation comprising a population of lactic acid bacteria. In certain embodiments, administration of the probiotic preparation improves in the subject one or more of: motor symptoms, non-motor symptoms, systemic inflammatory markers. In certain embodiments, administration of the probiotic preparation improves non-motor symptoms in the subject, for example improves gastrointestinal non-motor symptoms in the subject. In certain embodiments, administration of the probiotic preparation slows or prevents the onset of Parkinson's Disease symptoms such as motor symptoms.

In certain preferred embodiments the subject is in a state of gastrointestinal dysbiosis. In certain preferred embodiments the subject is exhibiting an elevated level of Firmicutes in their gut microbiota compared to healthy controls. In certain preferred embodiments the subject is exhibiting a reduced level of Bacteroidetes in their gut microbiota compared to healthy controls.

In certain preferred embodiments of all aspects, the population of lactic acid bacteria comprises at least one of *Lactobacillus rhamnosus, Lactobacillus acidophilus, Lactobacillus plantarum* and *Enterococcus faecium* bacteria. In certain embodiments, the population of lactic acid bacteria comprises at least two or at least three of *Lactobacillus rhamnosus, Lactobacillus acidophilus, Lactobacillus plantarum* and *Enterococcus faecium* bacteria.

In certain embodiments, the population of lactic acid bacteria comprises *Lactobacillus rhamnosus, Lactobacillus acidophilus*, and *Lactobacillus plantarum* bacteria.

In certain preferred embodiments, the population of lactic acid bacteria comprises each of *Lactobacillus rhamnosus, Lactobacillus acidophilus, Lactobacillus plantarum* and *Enterococcus faecium* bacteria.

BRIEF DESCRIPTION OF FIGURES

FIG. 2: Average log(copies/mL)±sd (lumen; n=3) or average log(copies/g)±sd (mucus; n=3) for the SYMPROVE™ bacteria in the luminal and mucosal compartments of the proximal and distal colon of the three donors for the donor control samples (C) and following 1 week (T1), 2 weeks (T2) and 3 weeks (T3) daily dosing with SYMPROVE™. *L. acidophilus* (top left), *L. plantarum* (top right), *L. rhamnosus* (bottom left) and *E. faecium* (bottom right).

FIG. 4: Average total BCFA (top) and ammonium (bottom) concentrations±sd (n=3) in the proximal and distal colon of the three donors for the donor control samples and following 3 weeks daily dosing with SYMPROVE™.

FIG. 6: Abundance (%) of the different families belonging to the phyla in the lumen of the proximal and distal colon of the M-SHIME media at the end of the control (C) and treatment with SYMPROVE™ (TR) periods for three human donors (n=1 for each donor)

FIG. 7: Abundance (%) of the different families belonging to the phyla in the mucosal layer of the proximal and distal colon of the M-SHIME media at the end of the control (C) and treatment with SYMPROVE™ (TR) periods for three human donors (n=1 for each donor)

FIG. 12: Treatment effects at OTU level in liver cirrhosis patients (25 most abundant OTUs are shown). Values represent the difference between the relative abundance of an OTU in the treatment and in the corresponding blank, averaged over three replicates per donor. Positive values thus indicate stronger enrichment in the treatment incubation, and have been indicated in green. Statistically significant differences between treatment and blank for a given donor and family have been indicated in bold. The T-test column shows statistically significant differences in relative abundance in the treatment and in the blank over the three donors, with p-values<0.05 indicated.

FIG. 13: Treatment effects at family level in liver cirrhosis patients. Values represent the difference in relative abundance of a bacterial family between the treatment and the corresponding blank, averaged over three replicates per donor. Positive values thus indicate stronger enrichment in the treatment incubation, and have been indicated in green. Statistically significant differences in relative abundance between treatment and blank for a given donor and family have been indicated in bold. The final column shows statistically significant differences in relative abundance of a given family between the treatment and the blank over the three donors, with p-values<0.05 indicated.

FIG. 14: Treatment effects at OTU level in patients with Parkinson disease (25 most abundant OTUs are shown). Values represent the difference between the relative abundance of an OTU in the treatment and in the corresponding blank, averaged over three replicates per donor. Positive values thus indicate stronger enrichment in the treatment incubation, and have been indicated in green. Statistically significant differences between treatment and blank for a given donor and family have been indicated in bold. The T-test column shows statistically significant differences in relative abundance in the treatment and in the blank over the three donors, with p-values<0.05 indicated.

FIG. 15: Treatment effects at family level in Parkinson patients. Values represent the difference in relative abundance of a bacterial family between the treatment and the corresponding blank, averaged over three replicates per donor. Positive values thus indicate stronger enrichment in the treatment incubation, and have been indicated in green. Statistically significant differences in relative abundance between treatment and blank for a given donor and family have been indicated in bold. The final column shows statistically significant differences in relative abundance of a given family between the treatment and the blank over the three donors, with p-values<0.05 indicated.

FIG. 16: Treatment effects at OTU level in IBD patients (25 most abundant OTUs are shown). Values represent the difference between the relative abundance of an OTU in the treatment and in the corresponding blank, averaged over three replicates per donor. Positive values thus indicate stronger enrichment in the treatment incubation, and have been indicated in green. Statistically significant differences between treatment and blank for a given donor and family have been indicated in bold. The T-test column shows statistically significant differences in relative abundance in the treatment and in the blank over the three donors, with p-values<0.05 indicated.

FIG. 17: Treatment effects at family level in IBD patients. Values represent the difference in relative abundance of a bacterial family between the treatment and the corresponding blank, averaged over three replicates per donor. Positive values thus indicate stronger enrichment in the treatment incubation, and have been indicated in green. Statistically significant differences in relative abundance between treatment and blank for a given donor and family have been indicated in bold. The final column shows statistically significant differences in relative abundance of a given family between the treatment and the blank over the three donors, with p-values<0.05 indicated.

FIG. 25: Effect of colonic batch samples on secretion of CXCL10 (A), IL-8 (B) and MCP-1 (C). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. (*)=p<0.05; ()=p<0.01; (*)=p<0.001. Data are represented for each donor separately and as the mean of all donors (Donor G-I).

DETAILED DESCRIPTION

Figure 1:
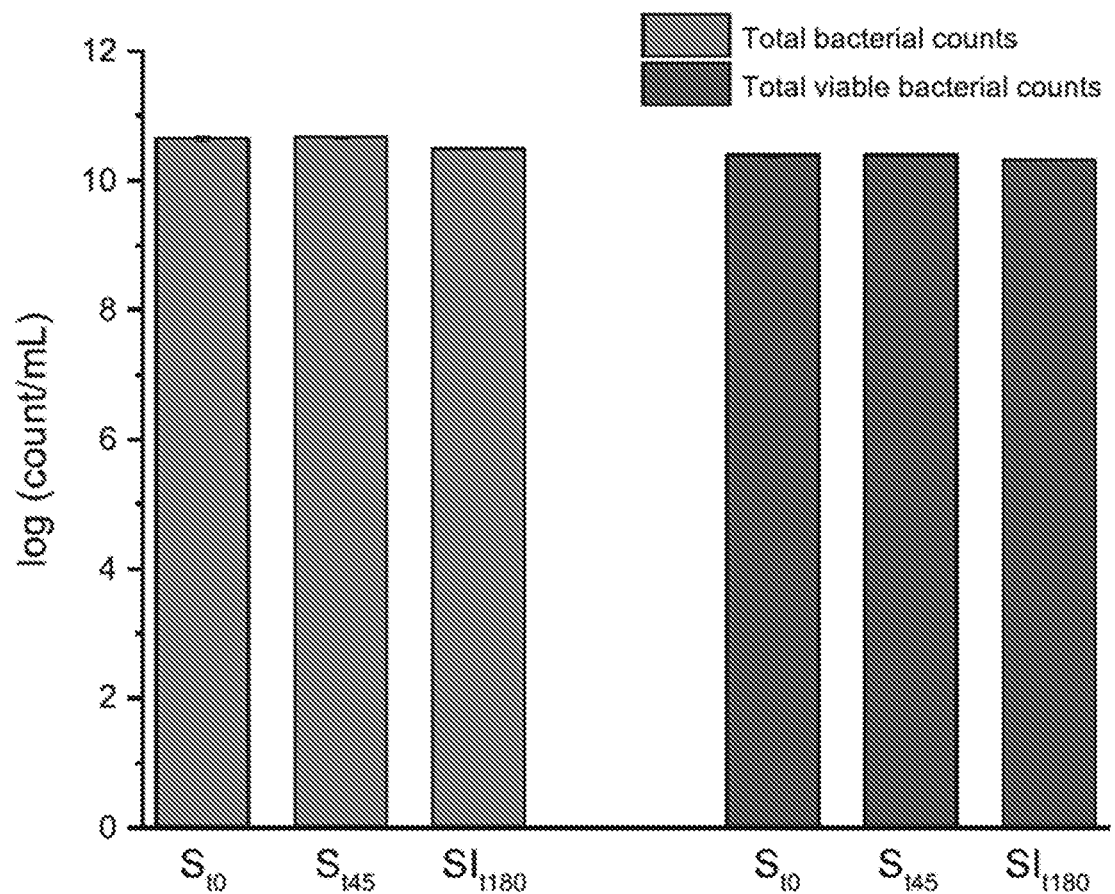
FIG. 1: Total bacterial counts (left) and total viable cell counts (right), determined with flow cytometry, for SYMPROVE™ bacteria upon addition to stomach juice (St0), after 45 min in stomach juice (St45) and after 180 min in small intestinal fluid (SIt180).

"Probiotic"—as used herein the term "probiotic" is to be interpreted according to the FAO/WHO joint report and guidelines for use of probiotics, in which probiotics are defined as "live microorganisms which when administered in adequate amounts confer a health benefit to the host". The term "probiotic bacteria" refers to any bacterial strain which fulfils this definition of a "probiotic".

"Lactic acid bacteria (LAB)"—as used herein the term "lactic acid bacteria (LAB)" refers to a group of Gram positive, catalase negative, non-motile anaerobic bacteria that ferment carbohydrates to lactic acid. This group includes the genera *Lactobacillus, Lactococcus, Pediococcus, Bifidobacterium,* and *Enterococcus.* Exemplary probiotic lactic acid bacteria include, but are not limited to, those in the genera *Lactobacillus* and *Enterococcus.*

"Dysbiosis"—as used herein, "dysbiosis" refers to the state when an individual exhibits abnormal types and/or relative numbers of bacteria in the gut compared to the values for a healthy gut. An individual with dysbiosis can be healthy—that is, the individual does not have a disease, condition or pathology associated with the dysbiosis. Alternatively, an individual with dysbiosis may be suffering from a disease, condition or pathology, for example a disease condition or pathology that is thought to cause or be caused by dysbiosis.

"Promoting gastrointestinal health"—as used herein "promoting gastrointestinal health" refers to improving gastrointestinal microbial health, indicated by an increase in SCFA production. Gastrointestinal health can be promoted in healthy individuals, resulting for example in reduced risk of colon cancer, and also in individuals suffering from a disease, condition or pathology. Promoting gastrointestinal health is especially important for individuals exhibiting dysbiosis.

"Complex carbohydrates"—as used herein the term "complex carbohydrates" includes both oligosaccharides and polysaccharides. "Oligosaccharides" are saccharide polymers containing 3 to 10 saccharide units; whereas the term "polysaccharides" includes longer polymeric structures, such as those formed from repeating saccharide (or disaccharide) units.

"Simple sugars"—as used herein the term "simple sugars" refers to both monosaccharides and disaccharides, unless otherwise stated.

"Reducing sugars"—as used herein the term "reducing sugars" refers to sugars which either have an aldehyde group or are capable of forming an aldehyde group in solution through isomerisation. The presence of reducing sugars may be determined by means of the Nelson-Somogyi method using glucose as the reference standard (Somogyi, M. (1052) Journal of Biological Chemistry., Vol. 195., p.19; reproduced in many standard textbooks of carbohydrate chemistry). Although certain complex carbohydrates (e.g. starches) may contain reducing ends, and therefore fulfil the definition of "reducing sugars", a determination of the content of "reducing sugars" in a given sample (e.g. a sample of probiotic preparation as described herein) using the Nelson-Somogyi method may be taken as an approximation of the amount of simple sugars in the sample, since the simple sugars contain a greater proportion of reducing ends per unit mass than complex carbohydrates.

"Total carbohydrate content"—as used herein the terms "total carbohydrate" or "total carbohydrate content" refer to the total amount of complex carbohydrate and simple sugars present in a given product (e.g. a probiotic preparation as described herein). Total carbohydrate content may be measured using the phenol-sulphuric acid assay, using glucose as a reference standard (Dubois, M., Gilles, K. A., Hamilton, J. K., Rebers, P. A. and Smith, F. (1956) *Analytical Chemistry*, vol. 28., p. 350).

Where reference is made herein to the ratio of total carbohydrate content to reducing sugar content of a liquid-based product (e.g. in a probiotic preparation) then this is to be determined by calculating the ratio of total carbohydrate content of the product, as measured by the phenol-sulphuric acid method described herein (result expressed in mg/ml), to reducing sugar content of the product, as measured by the Nelson-Somogyi method described herein (result expressed in mg/ml).

"Non-dairy"—as used herein the term "non-dairy" refers to products which do not contain and are not based upon milk from a mammal, in accordance with the definition accepted in the art. Accordingly, non-dairy products do not contain and are not based upon milk, butter, cheese (including vegetarian cheese), yoghurt, cream, milk powder, whey, lactose, lactoproteins (including caseins and caseinates), anhydrous milk fat or kefir.

"Subject"—as used herein, "subject" refers to a mammalian, preferably human, subject to whom the probiotic preparation is administered.

The following embodiments are embodiments according to each aspect of the present invention, and any embodiment may be combined with any other embodiment unless explicitly stated otherwise.

In order for probiotics to work effectively and to their optimum, they need to survive the conditions of the upper gastrointestinal (GI) tract without triggering digestion. If digestion is triggered, the stomach acids can weaken or destroy probiotic bacteria. This is a particular problem for probiotics formulated as yoghurt-type drinks, which are known to trigger production of stomach acid, pepsin and other digestive compounds.

In contrast, and as demonstrated herein, administration of a liquid, non-dairy probiotic preparation in accordance with the methods of the invention results in the bacteria in the preparation surviving the conditions of the GI tract and establishing in both the mucosal and luminal compartments of the gut (including the small intestine and colon).

Once established in the mucosal and luminal compartments of the gut, the probiotic bacteria are able to modify the established gut microbiota in terms of both composition and fatty acid production, promoting the production of beneficial SCFAs characteristic of improved gut health.

Without wishing to be bound by theory, it is hypothesised that because the probiotic bacteria are able to establish in the luminal compartment and especially in the mucosa, the probiotic effect is able to be persistent and maintained. This is in contrast with the effect seen with many probiotics, where the inability to influence the gut microbiota as a whole, and the mucosal microbiota in particular, means any effect is restricted to a transient effect on the luminal compartment. This is because any effect of such alternative probiotics will only occur during the transit of the probiotic bacteria through the digestive tract.

Promoting a healthy gut microbiota by administering a probiotic preparation in accordance with the invention can thus make an important contribution to a person's overall wellbeing and health, both when that person is otherwise healthy and also when that person is suffering from a disease, disorder or pathological condition.

Thus, in a first aspect is provided a method of promoting gastrointestinal health in a subject comprising administering a liquid, non-dairy probiotic preparation comprising a population of lactic acid bacteria, wherein administration of the probiotic preparation promotes production of one or more SCFAs by the subject's gut microbiota, thereby promoting gastrointestinal health.

SCFAs are thought to contribute to human intestinal health via a variety of mechanisms, for example by inhibiting pathogenic growth by lowering pH in the intestinal lumen and improving the ability of epithelial cells to defend against pathogenic *E. coli* infection. In addition, butyrate is a major energy source for host colonocytes and induces differentiation in these cells, which is thought to be related to a reduced risk of colon cancer. Butyrate and propionate have been reported to induce the differentiation of T-regulatory cells via inhibition of histone deacetylation, resulting in improved gut barrier maintenance.

Acetate, propionate and butyrate have also been reported to have a protective effect on diet-induced obesity. This is reported to be due to a loss of appetite following the production of gut hormones (in response to butyrate or propionate) or due to action on the central nervous system (in the case of acetate).

Thus, in a second aspect is provided a method of stimulating production of one or more short chain fatty acids (SCFAs) by a subject's gut microbiota comprising administering to the subject a liquid, non-dairy probiotic preparation comprising a population of lactic acid bacteria.

In certain preferred embodiments, stimulating production of one or more SCFAs can be used to treat conditions such as *Clostridium difficile* infection, MRSA infection, *E. coli* infection, obesity, diabetes, and chronic fatigue syndrome or to reduce the likelihood of developing colon cancer.

The interplay of the different bacteria making up any one individual's gut microbiota is complex and likely to be highly dependent on the other bacteria present in the microbiota, and their proportions, amongst other factors. Nevertheless, broad changes in bacterial phyla have been associated with poor gut health or poor gut integrity, for example reduced levels of Firmicutes in inflammatory conditions.

Modulating the growth and proportions of the bacterial taxa that go to form the gut microbiota of a subject may therefore represent a further process by which to promote gut health. As demonstrated herein, administration of a probiotic preparation in accordance with the invention results in modulation of the bacterial taxa in the gut microbiota, promoting the relative growth of some bacterial taxa and inhibiting others. Notably, the changes in the composition of the gut microbiota are not simply due to increased numbers of the probiotic bacteria in the preparation. Instead, probiotic bacteria colonise the gut and thereafter effect changes in the relative numbers and balance of other microbiota bacteria.

Thus, in a further aspect is provided a method of promoting growth of one or more bacterial phyla selected from Actinobacteria (e.g. Bifidobacteriaceae), Firmicutes (e.g. Veillonellaceae, Lachnospiraceae, Streptococcaceae, Eubacteriaceae, Ruminococcaceae, Erysipelotrichaceae, Clostridiaceae), Proteobacteria (e.g. Enterobacteriaceae) in the gut microbiota of a subject, the method comprising administering to the subject a liquid, non-dairy probiotic preparation comprising a population of lactic acid bacteria. Preferably the method promotes growth of two or more, preferably 3 or more, of said bacterial phyla.

In a further aspect is provided a method of inhibiting growth of one or more bacterial phyla selected from Actinobacteria (e.g. Coriobacteriaceae, Eggerthellaceae), Bacteroidetes (e.g. Bacteroidaceae, Rikenellaceae, Lachnospiraceae, Ruminococcaceae), Firmicutes (e.g., Acidaminococcaceae, Enterococcaceae, Clostridiaceae, Peptostreptococcaceae), Proteobacteria (e.g. Enterobacteriaceae), Synergistetes (e.g. Synergistaceae) and Verrucomicrobio (e.g. Akkermansiaceae) in the gut microbiota of a subject, the method comprising administering to the subject a liquid, non-dairy probiotic preparation comprising a population of lactic acid bacteria. Preferably the method inhibits growth of two or more, preferably 3 or more, of said bacterial phyla.

In certain preferred embodiments of all aspects of the invention, the method is a non-therapeutic method.

In certain preferred embodiments the subject is a healthy individual.

In certain preferred embodiments the subject is in a state of gastrointestinal dysbiosis.

In certain preferred embodiments, the subject is suffering from a disease or disorder. In certain such embodiments, the subject suffering from a disease or disorder is in a state of gastrointestinal dysbiosis associated with said disease or disorder.

In certain preferred embodiments, the subject has a disease or disorder selected from Parkinson's Disease, liver cirrhosis, inflammatory bowel syndrome (IBD), *Clostridium difficile* infection, MRSA infection, *E. coli* infection, *salmonella* infection, norovirus infection, giardiasis, coeliac disease, chronic kidney disease, HIV/AIDS, cystic fibrosis, type I diabetes, obesity, irritable bowel syndrome (IBS), and chronic fatigue syndrome. In certain preferred embodiments, the subject has Parkinson's Disease. In certain preferred embodiments, the subject has liver cirrhosis. In certain embodiments the patient has IBD.

In certain preferred embodiments of all aspects of the invention, the method promotes growth of one or more bacteria selected from Bifidobacteriaceae, Microbacteriaceae, Veillonellaceae, Lachnospiraceae, Streptococcaceae, Eubacteriaceae, Ruminococcaceae, Erysipelotrichaceae, Clostridiaceae, Enterobacteriaceae.

In certain preferred embodiments of all aspects of the invention, the method inhibits growth of one or more bacteria selected from Coriobacteriaceae, Eggerthellaceae, Bacteroidaceae, Rikenellaceae, Lachnospiraceae, Ruminococcaceae, Acidaminococcaceae, Enterococcaceae, Clostridiaceae, Peptostreptococcaceae, Enterobacteriaceae, Synergistaceae and Akkermansiaceae. In a particularly preferred embodiment, the method inhibits growth of Bacteroidaceae bacteria.

Preferably the effect on bacterial growth is in the gut mucosal compartment.

Preferably the effect on bacterial growth is in the gut luminal compartment.

Preferably the effect on bacterial growth is in the proximal colon.

Preferably the effect on bacterial growth is in the distal colon.

In a preferred embodiment, the method promotes production of one or more SCFAs.

Short Chain Fatty Acid Production

In preferred embodiments of all aspects of the methods of the invention, the methods promote production of one or more SCFAs, where the SCFAs are selected from acetate, propionate, and butyrate (used interchangeably herein with acetic acid, propionic acid and butyric acid, respectively).

As described elsewhere herein, production of these SCFAs is associated with a healthy gastrointestinal tract and is linked to a range of health and wellbeing benefits. An increase in SCFA production can therefore be indicative of an improvement in gastrointestinal (GI) health.

An increase in SCFA production may also be indicative of changes in the composition of the gut microbiota. For instance, acetate can be produced by many different gut microbes, including Actinobacteria such as *Bifidobacterium* sp. Similarly, propionate can be produced by a wide range of gut microbes, including Firmicutes such as Veillonellaceae. Butyrate is primarily produced by Firmicutes bacteria such as the Clostridiaceae.

Production of SCFAs can result in cross-feeding, whereby SCFAs such as acetate and propionate produced by some microbiota bacteria acts as food source for other bacteria which convert them to butyrate. Butyrate itself can then be used as a food source by gut epithelial cells.

Butyrate in particular is thought to confer health benefits when produced by the gut microbiota. Accordingly, in certain preferred embodiments, the method promotes butyrate production by the gut microbiota.

Conversely, branched chain fatty acids (BCFAs) such as isobutyrate, isovalerate and isocaproate, as well as ammonium species, are produced by proteolytic bacterial activity and are thought to be detrimental to health. Advantageously, the methods according to the invention can reduce levels of BCFA and ammonium species produced by a subject's gut microbiota.

Thus, in certain preferred embodiments, methods of the invention reduce production of one or more BCFAs by a subject's gut microbiota. In certain embodiments the one or more BCFAs are selected from isobutyrate, isovalerate and isocaproate. In certain embodiments methods of the invention reduce production of isobutyrate. In certain embodiments methods of the invention reduce production of isovalerate. In certain embodiments methods of the invention reduce production of isocaproate. In certain embodiments methods of the invention reduce production of 2-methyl butyrate.

In certain preferred embodiments, methods of the invention reduce production of one or more ammonium species by a subject's gut microbiota.

Promotion of Intestinal Barrier Integrity

The intestinal epithelial barrier is formed by intercellular tight junctions, a complex protein-protein network that mechanically links adjacent cells and seals the intercellular space. A healthy intestinal epithelial barrier regulates the permeability of the gut, controlling movement of molecules from the luminal space into the deeper mucosal layers such as the lamina propria and the gut capillaries. Intestinal barrier integrity is thus important for gastrointestinal health and overall wellbeing.

Disruption of intestinal barrier integrity can result in increased gut permeability and disregulated movement of gut luminal contents into the gut lamina propria, which can lead to adverse immune reactions, both locally in the gastrointestinal tract and systemically. It is therefore important to maintain intestinal barrier integrity or repair any loss of barrier integrity to maintain general and gastrointestinal health.

As demonstrated in the Examples below, administration of a probiotic preparation as provided herein promotes intestinal barrier function and integrity. This is demonstrated both by the ability to maintain healthy intestinal barrier function and also by the ability to repair the intestinal barrier following damage or wounding.

Accordingly, in a further aspect is provided a method of promoting intestinal barrier integrity in a subject, the method comprising administering to the subject a liquid, non-dairy probiotic preparation comprising a population of lactic acid bacteria, wherein administration of the probiotic preparation promotes said intestinal barrier integrity.

In certain embodiments, the method maintains healthy intestinal barrier integrity. That is, the method prevents or reduces loss of intestinal barrier function in a subject.

In certain such embodiments, the subject may be a healthy subject.

Alternatively, in certain such embodiments, the subject may be at increased risk of loss of intestinal barrier integrity, for example due to undergoing antibiotic therapy, chemotherapy or radiotherapy. In certain embodiments the subject may be at risk of loss of intestinal barrier integrity, for example because the subject has a condition associated with loss of intestinal barrier function.

In certain embodiments the subject may be at risk of loss of intestinal barrier function because the subject has been diagnosed with a disease selected from: *salmonella* infection, norovirus infection, giardiasis, coeliac disease, chronic kidney disease, HIV/AIDS, cystic fibrosis, liver cirrhosis, Parkinson's Disease, and type I diabetes.

As demonstrated herein, the provided methods are particularly effective in intestinal barrier models from patients with Parkinson's Disease or with liver cirrhosis. Therefore, in certain embodiments the subject may be at risk of loss of intestinal barrier function because the subject has been diagnosed with Parkinson's Disease. In certain embodiments the subject may be at risk of loss of intestinal barrier function because the subject has been diagnosed with liver cirrhosis.

In certain embodiments, the method promotes intestinal barrier repair. Promoting intestinal barrier repair is important where a subject is already experiencing symptoms indicative of a barrier dysfunction, for example local gut inflammation and/or a systemic inflammatory response. A number of conditions are known to damage intestinal barrier function, including: *salmonella* infection, norovirus infection, giardiasis, coeliac disease, chronic kidney disease, HIV/AIDS, cystic fibrosis and type I diabetes.

Therefore in certain embodiments, the method promotes intestinal barrier repair in a subject suffering from one or more diseases selected from: *salmonella* infection, norovirus infection, giardiasis, coeliac disease, chronic kidney disease, HIV/AIDS, cystic fibrosis, liver cirrhosis, irritable bowel disease (IBS), Parkinson's Disease, and type I diabetes.

In certain embodiments the subject the method promotes intestinal barrier repair in a subject that has been diagnosed with Parkinson's Disease. In certain embodiments the method promotes intestinal barrier repair in a subject that has been diagnosed with liver cirrhosis.

In certain embodiments the method promotes intestinal barrier repair in a subject that has been diagnosed with inflammatory bowel disease (ulcerative colitis or Crohn's Disease).

In certain embodiments, the method is a method of treating a subject suffering from leaky gut syndrome.

It will be appreciated that the above-described embodiments in relation to a method of promoting intestinal barrier integrity apply equally and independently to the other method aspects provided herein. For example, a method of promoting gastrointestinal health as provided herein may promote SCFA production in the gut and also promote intestinal barrier function. Similarly, a method of promoting intestinal barrier integrity may promote SCFA (e.g. butyrate) production and also (or thereby) reduce loss of intestinal barrier function. Similarly, a method of treating Parkinson's disease as provided herein may promote intestinal barrier function and/or intestinal barrier repair.

Promotion of Tolerogenic Gut Phenotype

The data presented in the accompanying Examples demonstrates that the probiotic preparation provided herein is able to influence the expression of various immune molecules (e.g. cytokines, chemokines, and ligands). The data shows that administration of the probiotic preparation is able to promote a "tolerogenic" or anti-inflammatory phenotype in intestinal epithelial cells (referred to hereafter as "tolerogenic gut phenotype" for brevity). This tolerogenic gut phenotype is characterised by increased production of one or more tolerogenic or anti-inflammatory molecules (e.g. IL-6 and IL-10), and/or by decreased production of one or more pro-inflammatory molecules (e.g. TNFa, IL-8 and MCP-1) in response to immunological challenge (for example LPS challenge).

Therefore, in a further aspect is provided a method for promoting a tolerogenic gut phenotype in a subject, the method comprising administering to the subject a liquid, non-dairy probiotic preparation comprising a population of lactic acid bacteria, wherein administration of the probiotic preparation promotes said tolerogenic gut phenotype.

In certain preferred embodiments, the method promotes production of one or more anti-inflammatory molecules, such as anti-inflammatory cytokines and anti-inflammatory chemokines, by intestinal epithelial cells. In certain embodiments, the method promotes production of IL-6. In certain embodiments, the method promotes production of IL-10.

In certain preferred embodiments, the method reduces production of one or more pro-inflammatory molecules, such as pro-inflammatory cytokines and pro-inflammatory chemokines, by intestinal epithelial cells. In certain embodiments, the method reduces production of MCP-1. In certain embodiments, the method reduces production of CXCL10. In certain embodiments, the method reduces production of IL-8. In certain embodiments, the method reduces production of TNFa.

In these embodiments, the method changes secretion of the pro-inflammatory or anti-inflammatory molecules by intestinal epithelial cells. In certain embodiments the change in secretion of the pro-inflammatory or anti-inflammatory molecules by intestinal epithelial cells is detectable in the gut lumen, for example by lavage. In certain embodiments the change in secretion of the pro-inflammatory or anti-inflammatory molecules by intestinal epithelial cells is detectable in a blood sample.

In certain embodiments, the relative immune molecule production of a subject having a tolerogenic gut phenotype may, for example, be in comparison to the immune molecule production exhibited by the subject's gut epithelial cells prior to the probiotic preparation being administered according to the methods provided herein. Alternatively, the relative production may be in comparison to a control subject who has not been administered the probiotic preparation according to the methods provided herein. Alternatively, the relative immune molecule production may be in comparison to a predetermined control value, for example the median level of production of a control population.

It will again be appreciated that the above-described embodiments in relation to a method of promoting a tolerogenic gut phenotype apply equally and independently to the other method aspects provided herein. For example, a method of promoting gastrointestinal health as provided herein may also promote the production of one or more anti-inflammatory molecules by gut epithelial cells.

Without wishing to be bound by theory, it is hypothesised that the tolerogenic gut phenotype induced by the provided methods is encouraged by the increased intestinal barrier integrity also induced by administration of the probiotic preparations. In particular, by reducing gut permeability, fewer macromolecules and microorganisms can reach the mucosal immune cells such as in the lamina propria. Macromolecule and microorganism transit to the lamina propria is thought to trigger pro-inflammatory responses. Therefore by promoting intestinal barrier integrity it is hypothesised that the methods provided herein reduce the pro-inflammatory triggers reaching the mucosal immune cells, thereby promoting a more tolerogenic or anti-inflammatory gut phenotype.

In certain embodiments the subject the method promotes a tolerogenic gut phenotype in a subject that has been diagnosed with Parkinson's Disease. In certain embodiments the method promotes a tolerogenic gut phenotype in a subject that has been diagnosed with liver cirrhosis. In certain embodiments the method promotes a tolerogenic gut phenotype in a subject that has been diagnosed with inflammatory bowel disease (ulcerative colitis or Crohn's Disease).

In certain such embodiments, the method is a method of treating a subject suffering from leaky gut syndrome.

In certain alternative embodiments, the subject is a healthy subject.

It will be appreciated that, unless inherently incompatible, the above-described embodiments in relation to a method of promoting a tolerogenic gut phenotype apply equally and independently to the other method aspects provided herein. For example, a method of promoting gastrointestinal health as provided herein may promote SCFA production in the gut and also promote a tolerogenic gut phenotype. Similarly, a method of promoting a tolerogenic gut phenotype may promote SCFA (e.g. butyrate) production and also (or thereby) promote a tolerogenic gut phenotype. Similarly, a method of treating Parkinson's disease as provided herein may promote a tolerogenic gut phenotype.

Parkinson's Disease

As reported in the accompanying Examples, Parkinson's Disease patients receiving a probiotic preparation as described herein report improvement in their disease symptoms. Furthermore, when assessed in detailed in vitro models of the gut of Parkinson's Disease patients, administration of a probiotic preparation as described herein results in increased SCFA production, increased intestinal barrier integrity, improved intestinal barrier repair and a shift towards an anti-inflammatory/tolerogenic gut phenotype.

Without wishing to be bound by theory, the data provided herein provides a hypothesis for the mechanism by which administration of the probiotic preparation treats Parkinson's Disease. Parkinson's Disease has been associated with impaired gut barrier function, as well as increased inflammation in the gut. This abnormal gut environment can lead to misfolding of alpha-synuclein, the protein abnormally deposited in Parkinson's Disease. It is hypothesised that the misfolded alpha-synuclein could be transported via the vagus nerve to the brain (a known gut-brain axis), thereby causing or exacerbating Parkinson's Disease symptoms.

As demonstrated in the Examples, administration of the probiotic preparation results in improved intestinal barrier integrity, an anti-inflammatory/tolerogenic environment and increased SCFA production. These effects will normalise the gut environment thereby mitigating the conditions promoting misfolding of alpha-synuclein, as well as reduce the permeability of the gut and thus the risk that the misfolded protein is transported to the brain. Administration of the probiotic preparation according to the invention therefore offers the reduction of central neurological symptoms of Parkinson's Disease, as well as treating the gastrointestinal non-motor symptoms.

Accordingly, in a further aspect is provided a method of treating or preventing Parkinson's Disease in a subject, the method comprising administering to the subject a liquid, non-dairy probiotic preparation comprising a population of lactic acid bacteria.

In certain preferred embodiments, administration of the probiotic preparation treats Parkinson's Disease in the subject by improving one or more of, preferably two or more of, preferably all of: motor symptoms, non-motor symptoms, peripheral blood inflammatory markers and gut inflammatory markers. In certain preferred embodiments, administration of the probiotic preparation treats Parkinson's Disease in the subject by improving motor symptoms. In certain preferred embodiments, administration of the probiotic preparation treats Parkinson's Disease in the subject by improving non-motor symptoms.

In certain preferred embodiments, administration of the probiotic preparation treats Parkinson's Disease in the subject by improving peripheral blood inflammatory markers and/or gut inflammatory markers. In certain embodiments, the method reduces production of MCP-1. In certain embodiments, the method reduces production of CXCL10. In certain embodiments, the method reduces production of IL-8. In certain embodiments, the method reduces production of TNFa.

In certain embodiments, administration of the probiotic preparation slows or prevents the onset of Parkinson's Disease symptoms such as motor symptoms.

Techniques for assessing the severity of Parkinson's Disease symptoms, for example motor, non-motor and cognitive symptoms, are familiar to the skilled person and are provided in Example 3. For instance, motor symptoms can be assessed using the Movement Disorder Society Unified Parkinson's Disease Rating Scale (MDS-UPDRS) parts III and IV, and cognitive symptoms can be assessed by the Montreal Cognitive Assessment (MoCA) criteria. Further techniques for assessing symptom severity are detailed in Example 3.

In preferred embodiments, administration of the probiotic preparation treats Parkinson's Disease in the subject by improving one or more non-motor symptoms. Non-motor symptoms that may be exhibited by a subject with Parkinson's Disease and which may be improved according to the method of the invention include: cardiovascular abnormalities (e.g. hypotension), depression, anxiety, sexual function abnormalities, sensory disturbances, gastrointestinal symptoms (e.g. constipation), and sleep disorders.

An overall assessment of non-motor symptoms (NMS) in a Parkinson's patient can be assessed using the non-motor symptoms scale (NMSS), as described in the accompanying Examples. In preferred embodiments, administration of the probiotic preparation treats Parkinson's Disease in the subject by improving the NMSS of the subject.

In preferred embodiments, administration of the probiotic preparation treats Parkinson's Disease in the subject by improving gastrointestinal non-motor symptoms in the subject. In preferred embodiments, administration of the probiotic preparation treats Parkinson's Disease in the subject by improving constipation symptoms, for example by increasing the number of bowel movements per day and/or by reducing the number of laxatives the subject needs to take.

In preferred embodiments, administration of the probiotic preparation treats or prevents Parkinson's Disease in the subject by reducing the severity or slowing the progression of motor symptoms (that is slowing the rate at which severity increases). In preferred embodiments, administration of the probiotic preparation treats or prevents Parkinson's Disease in the subject by slowing or preventing the onset of motor symptoms.

In certain preferred embodiments of the methods, the subject is in a state of gastrointestinal dysbiosis. In certain preferred embodiments the subject is exhibiting an elevated level of Firmicutes in their gut microbiota compared to healthy controls. In certain preferred embodiments the subject is exhibiting a reduced level of Bacteroidetes in their gut microbiota compared to healthy controls.

In certain embodiments the method further comprises the step of measuring the level of Firmicutes and/or Bacteroidetes in a sample of the gut microbiota obtained from the subject, where the subject is administered the probiotic preparation if the subject is exhibiting an elevated level of Firmicutes compared to healthy controls and/or if the subject is exhibiting a reduced level of Bacteroidetes in their gut microbiota compared to healthy controls.

In preferred embodiments the method comprises administering the probiotic to the subject at least once a day.

In preferred embodiments the method comprises administering the probiotic to the subject for at least 1 week, preferably at least 2 weeks, preferably at least 3 weeks, preferably at least 4 weeks. In preferred embodiments, the method comprises administering the probiotic to the subject for at least 1 month, preferably at least 2 months. In preferred embodiments the method comprises administering the probiotic to the subject for at least at least 3 months.

It will be appreciated that, except where inherently incompatible, the aspects and embodiments of other methods of the invention provided herein apply equally and independently to the method of treating Parkinson's Disease according to the invention.

For example, a method of treating Parkinson's Disease may promote SCFA production in the gut and also promote intestinal barrier function and/or a tolerogenic gut phenotype.

Accordingly, in certain embodiments of the method of treating Parkinson's Disease, administration of the probiotic preparation improves intestinal barrier integrity.

In certain embodiments of the method of treating Parkinson's Disease, administration of the probiotic preparation improves intestinal barrier repair.

In certain embodiments of the method of treating Parkinson's Disease, administration of the probiotic preparation promotes a tolerogenic gut phenotype in the subject.

Composition of the Probiotic Preparation

The probiotic preparation used in accordance with the invention is a liquid product (not freeze-dried) which is non-dairy. Preferably the probiotic preparation is water-based.

The probiotic preparation contains a population of lactic acid bacteria. The lactic acid bacteria are viable and metabolically active probiotic bacteria and are therefore "alive" and ready to function immediately after the preparation is swallowed.

In certain embodiments, the probiotic bacteria are of the genus *Lactobacillus* or *Enterococcus*. In certain preferred embodiments, the population of lactic acid bacteria comprises one or more of *Enterococcus faecium, Lactobacillus plantarum, Lactobacillus acidophilus* and *Lactobacillus rhamnosus*.

Reference to *Lactobacillus rhamnosus* is intended to include any bacterial strain originally classified as *Lactobacillus casei* but now re-classified as *Lactobacillus rhamnosus*.

In certain preferred embodiments, the population of lactic acid bacteria comprises at least two or at least three of *Enterococcus faecium, Lactobacillus plantarum, Lactobacillus rhamnosus* and *Lactobacillus acidophilus*. In certain preferred embodiments, the population of lactic acid bacteria comprises *Lactobacillus plantarum, Lactobacillus rhamnosus* and *Lactobacillus acidophilus*.

In certain preferred embodiments, the population of lactic acid bacteria comprises each of *Enterococcus faecium, Lactobacillus plantarum, Lactobacillus rhamnosus* and *Lactobacillus acidophilus*.

The product SYMPROVE™ (containing *Enterococcus faecium, Lactobacillus plantarum, Lactobacillus rhamnosus* and *Lactobacillus acidophilus*) was shown to be particularly effective in promoting SCFA production and gut health in the study described herein. The strain of *Lactobacillus rhamnosus* in SYMPROVE™ was originally characterised as *Lactobacillus casei* but has now been re-classified as the closely related *Lactobacillus rhamnosus*.

In certain embodiments, the total population of metabolically active bacteria in the probiotic preparation may be in the range of from $1.0 \times 10^6$ to $1.0 \times 10^{10}$ viable cells per millilitre, preferably from $1.0 \times 10^6$ to $1.0 \times 10^9$ viable cells per millilitre, preferably in the range of from $1.0 \times 10^7$ to $1.0 \times 10^9$ viable cells per millilitre. Each individual strain of metabolically active bacteria present in the probiotic preparation independently may be present in the range of from $1.0 \times 10^5$ to $1.0 \times 10^9$ viable cells per millilitre, more preferably in the range of from $1.0 \times 10^7$ to $1.0 \times 10^9$ viable cells per millilitre.

In the case of probiotic preparations comprising a combination of *Lactobacillus plantarum* and *Lactobacillus rhamnosus* or a combination of *Enterococcus faecium, Lactobacillus plantarum*, and *Lactobacillus rhamnosus*, it is preferred that at least one and preferably each of these strains is present in the range of from $1.0 \times 10^6$ to $1.0 \times 10^{10}$ viable cells per millilitre, preferably in the range of from $1.0 \times 10^7$ to $1.0 \times 10^9$ viable cells per millilitre.

In certain embodiments, the population of *L. acidophilus*, if included, may be lower than $1.0 \times 10^5$ viable cells per millilitre, preferably in the range of from $1.0 \times 10^2$ to $1.0 \times 10^5$ viable cells per millilitre, optionally $1.0 \times 10^2$ to $1.0 \times 10^4$ viable cells per millilitre.

In an exemplary embodiment the preparation may comprise a combination of *Enterococcus faecium*, *Lactobacillus plantarum*, and *Lactobacillus rhamnosus*, wherein the bacterial count for each of these bacterial strain is in the range of from $1.0 \times 10^5$ to $1.0 \times 10^9$ viable cells per millilitre, more preferably in the range of from $1.0 \times 10^7$ to $1.0 \times 10^9$ viable cells per millilitre. The population of *L. acidophilus*, if included, may be lower than $1.0 \times 10^5$ viable cells per millilitre, preferably in the range of from $1.0 \times 10^2$ to $1.0 \times 10^5$ viable cells per millilitre, optionally $1.0 \times 10^2$ to $1.0 \times 10^4$ viable cells per millilitre.

In certain preferred embodiments, the liquid substrate of the probiotic preparation administered according to the methods of the invention typically contains a mixture of polysaccharides, oligosaccharides, disaccharides and monosaccharides.

In certain embodiments, the probiotic preparation may be characterised by the ratio of total carbohydrate content to reducing sugar content of the preparation, reflecting the complex mix of polysaccharides, oligosaccharides, disaccharides and monosaccharides present. In certain embodiments, the ratio of total carbohydrate content to reducing sugar content of the preparation is in the range of from 8:1 to 2:1, more typically in the range of from 5:1 to 2.5:1, or in the range of from 4:1 to 3:1.

In further exemplary embodiments of the probiotic preparation, the total carbohydrate (polysaccharides, oligosaccharides, disaccharides and monosaccharides) content of the preparation may be in the range of from 20 mg/ml to 40 mg/ml, or in the range of from 20 mg/ml to 30 mg/ml and the total reducing sugar content may be in the range of from 5 mg/ml to 20 mg/ml, or in the range of from 5 mg/mg to 10 mg/ml.

The probiotic preparation preferably also comprises protein and peptide components. Typically the total amount of protein and peptides present in the probiotic preparation is in the range of from 0.01 mg/ml to 2 mg/ml, preferably 0.05 mg/ml to 2 mg/ml. Preferably the total amount of high molecular weight peptides (molecular weight greater than 5000 Daltons) is in the range of from 10 µg/ml to 300 µg/ml, preferably of from 50 µg/ml to 200 µg/ml. In a specific embodiment, the concentration of protein and peptides may be about 1 mg/ml to about 2 mg/ml and the concentration of high molecular weight peptides may be about 250 µg/ml.

Means of measuring the concentrations of these nutritional components are provided in WO 2006/035218, which is incorporated herein by reference.

The probiotic preparation may contain further components such as, for example, cellulose, starch, β-glucans, pentosans, polyphenols, ribonucleic acids, lipids, phosphates, flavenoids, amino acids, vitamins ($B_1$, $B_2$, C and E), silicates and trace elements. The probiotic preparation may comprise an extract of germinated barley containing the desired probiotic bacterial strains.

An exemplary embodiment of the probiotic preparation comprises extract of germinated barley and a combination of *Enterococcus faecium*, *Lactobacillus plantarum*, *Lactobacillus rhamnosus*, wherein the bacterial count for each of these bacterial strain is in the range of from $1.0 \times 10^5$ to $1.0 \times 10^{10}$ viable cells per millilitre, more preferably in the range of from $1.0 \times 10^7$ to $1.0 \times 10^9$ viable cells per millilitre, and further contains *Lactobacillus acidophilus* at a concentration of lower than $1.0 \times 10^5$ viable cells per millilitre, preferably in the range of from $1.0 \times 10^2$ to $1.0 \times 10^5$ viable cells per millilitre, optionally $1.0 \times 10^2$ to $1.0 \times 10^4$ viable cells per millilitre.

Additional components may be added to the probiotic preparation, such as flavourings and/or colourings, to improve palatability.

The pH of the preparation can be conveniently controlled by the addition of a suitable buffer or combination of buffering agents. Preferred buffers include, for example, tri-sodium citrate or phosphate buffers. The pH of the liquid-based preparation described herein is typically maintained in the range of from 3.8 to 4.5, and in particular at about pH 4.0, during long-term storage. The probiotic preparation may be stored at any temperature from 4° C. up to ambient temperature (about 25° C.). The SYMPROVE™ product described herein has been shown to remain stable (in terms of bacterial count) for a period of at least 6 months when stored at about 4° C., and for at least 4 months when stored at 25° C.

The preparation may additionally comprises an anti-fungal agent, such as, for example, sterilised potassium sorbate and/or and anti-oxidant, such as vitamin C.

In a preferred embodiment the growth substrate may contain particulate matter, for example particles not exceeding 1 mm in diameter.

The most preferred embodiment of the probiotic preparation is the product denoted SYMPROVE™, containing viable, metabolically active cells of *Enterococcus faecium*, *Lactobacillus plantarum*, *Lactobacillus rhamnosus* and *Lactobacillus acidophilus*, which may be prepared according to the examples provided herein. The strain of *Lactobacillus rhamnosus* in SYMPROVE™ was originally characterised as *Lactobacillus casei* but has now been re-classified as the closely related *Lactobacillus rhamnosus*.

Administration

In certain preferred embodiments, the preparation is administered orally.

In certain preferred embodiments, the preparation is administered at least once a week. In certain preferred embodiments, the preparation is administered at least once a day, preferably once a day.

In certain preferred embodiments, the preparation is administered at dose in the range of from 0.5 mg/kg of the patient to 5 mg/kg of the patient. In a preferred embodiment, the preparation is administered at a dose of 1 mg/kg of the patient.

In certain preferred embodiments, the preparation is administered for at least 1 week, preferably at least 2 weeks, preferably at least 3 weeks, preferably at least 4 weeks. In certain preferred embodiments, the preparation is administered for at least 1 month. In certain preferred embodiments, the preparation is administered for at least 5, at least 6, at least 7, at least 8, at least 9, at least 10, at least 11 or at least 12 weeks.

In certain preferred embodiments, the preparation is administered at a dose of 1 mg/kg of the patient, at least once a day for at least 3 weeks, preferably at least 1 month.

Manufacture of the Probiotic Preparation

A probiotic preparation for use in in accordance with the methods of the invention may be prepared by growing one or more probiotic bacterial strains in a liquid growth substrate, such as for example an extract of germinated barley.

The growth substrate may be itself prepared starting from seed or malting sample barley using the manufacturing process described in WO 2006/035218, the contents of which are incorporated herein by reference.

An alternative method of producing the probiotic preparation which does not require an active growing step simply involves inoculated the growth substrate (e.g. the extract of germinated barley prepared as described in WO2006/035218) with starter culture(s) of probiotic bacteria. Starter cultures for the method include, for example, freeze-dried bacteria or liquid cultures. The growth substrate may be inoculated with more than one bacterial species. Preferably, the concentration of the viable cells in the starter culture is in excess of $10^6$ viable cells per millilitre. This method is also described in WO2006/035218. A further alternative method of producing the probiotic preparation is to compile a nutrient substrate meeting the nutrient requirements of the probiotic preparation described herein and also in WO2006/035218, and inoculating said substrate with the probiotic bacteria.

The invention will be further understood with reference to the following non-limiting experimental examples:

EXAMPLES

Example 1

The ability of the probiotic bacteria in SYMPROVE™ to influence three healthy human gut microbiotas was using an in-vitro gut model (Simulator of the Human Intestinal Microbial Ecosystem, equipped with mucosal compartments (M-SHIME®)); the effects on bacterial diversity, SCFA production and inflammatory markers, following dosing with SYMPROVE™ over a three-week period, were quantified. The manufacture of SYMPROVE™ and its nutritional composition are further provided in WO 2006/035218, which is incorporated herein by reference.

2. Materials and Methods 2.1. M-SHIME® Testing

SYMPROVE™ was obtained from SYMPROVE Ltd and used as received. Experiments were performed using the M-SHIME® system. Briefly, the system comprised four reactors vessels (V). The first two reactors are of the fill-and-draw principle and simulate the initial stages in food uptake and digestion. Peristaltic pumps add feed (140 mL, 3× per day) and pancreatic/bile juice (60 mL, 3× per day) to the stomach (V1) and small intestine (V2) respectively and empty each reactor after defined time intervals. The remaining 2 reactors simulate the conditions of the proximal (V3) and distal (V4) colon. Colon vessels are constantly stirred, retain a fixed volume (PC=500 mL; DC=800 mL) and their pH is constant (PC=5.6-5.9; DC=6.6-6.9). The retention time of media in each vessel is selected to mimic human in vivo conditions. The colon reactors were inoculated with faecal microbiota from healthy human donors (consuming a Western-style diet) and the microbial community was allowed to stabilise over a 2-week period. The microbiota was then maintained for a further 2-week control period. During this period, the baseline microbial community composition and activity were recorded. Three donors were used in this study to address inter-individual variability. A three-week treatment phase then commenced; SYMPROVE™ was added to V1 and was progressed through V2 prior to being fed to the colonic microbiota. One set of V1-V2 vessels was used to minimise variability of the feed material, meaning the feed arriving in the proximal colon vessels was the same for all donors. Mucin-covered microcosms were added to all colonic vessels, enabling maintenance of not only a luminal microbiota but also a specific mucosal microbiota in the colonic regions.

2.2. Quantification of Viable and Non-Viable Bacteria by Flow Cytometry

Samples were collected from different stages at various time intervals in V1 and V2 to investigate upper gastrointestinal survival of the probiotic species. A ten-fold dilution series was initially prepared in phosphate buffered saline. Assessment of the viable and non-viable populations of the bacteria was done by staining the appropriate dilutions with SYTO 24 and propidium iodide. Samples were analyzed on a BDFacs verse, using a high flow rate. Bacterial cells were separated from medium debris and signal noise by applying a threshold level of 200 on the SYTO channel. Proper parent and daughter gates were set to determine all populations. Results are reported as average log (counts)±sd of the three independent biological replicates.

2.3. Measurement of SCFA/BCFA, Lactate and Ammonium

SCFA levels, including acetate, propionate, butyrate and branched SCFA (isobutyrate, isovalerate and isocaproate) were monitored. Lactate quantification was performed using a commercially available enzymatic assay kit (R-Biopharm, Darmstadt, Germany) according to the manufacturer's instructions. Ammonium analysis was quantified by initially performing a steam distillation. Subsequently, the ammonium in the distillate was determined titrimetrically with HCl.

2.4. Microbial Community Analysis

During the reference and treatment periods, samples for microbial community analysis were collected once per week from each colon vessel. DNA was isolated starting from pelleted cells originating from 1 mL luminal or 0.1 g mucus samples. Numbers of the probiotic species were determined with a qPCR protocol, using species-specific primers and probes. Although the primers are species but not strain specific, the microbiota were established over a 4-week period prior to dosing with SYMPROVE™, so any increase in the numbers of bacterial species during the treatment period is a result of probiotic treatment, meaning strain specific primers were not required. The qPCR was performed on a QuantStudio 5 Real-Time PCR system (Applied Biosystems, Foster City, CA USA). Each sample was analysed in triplicate. Results are reported as average log (copies/mL) for the luminal samples and as average log (copies/g) for the mucosal samples±sd of the three technical replicates.

The microbiota profiling of each colon compartment was established by 16S-targeted sequencing analysis. Quality control PCR was conducted using Taq DNA Polymerase with the Fermentas PCR Kit according to the manufacturers' instructions (Thermo Fisher Scientific, Waltham, MA, USA). The obtained PCR product was run along the DNA extract on a 2% agarose gel for 30 min at 100 V. 10 μl of the original genomic DNA extract was sent out to LGC genomics GmbH (Germany) for library preparation and sequencing on an Illumina Miseq platform with v3 chemistry with the primers mentioned above.

2.5. Caco-2/THP1-Blue™ Co-Culture Model

The co-culture experiment was performed using Caco-2 cells (HTB-37; American Type Culture Collection) seeded in 24-well semi-permeable inserts (0.4 μm pore size) at a density of $1\times10^5$ cells/insert. Caco-2 monolayers were cultured for 14 days, with three changes of medium per week, until a functional monolayer with a transepithelial electrical resistance (TEER) of more than 300 Ωcm² was obtained (measured with a Millicell ERS-2 epithelial volt-ohm meter, Millipore). Cells were maintained in Dulbecco's Modified Eagle Medium (DMEM) containing glucose (25 mM) and glutamine (4 mM), supplemented with HEPES (10 mM) and heat-inactivated fetal bovine serum (HI-FBS, 20% v/v). THP1-Blue™ cells (InvivoGen) were seeded in 24-well plates at a density of $5 \times 10^5$ cells/well and treated with phorbol 12-myristate 13-acetate(PMA) for 48 h and maintained in Roswell Park Memorial Institute (RPMI) 1640 medium containing glucose (11 mM) and glutamine (2 mM), supplemented with HEPES (10 mM), sodium pyruvate (1 mM) and HI-FBS (10% v/v).

Before setting up the co-culture, the TEER of the Caco-2 monolayer was measured (the TEER of an empty insert was subtracted from all readings). Caco-2 bearing inserts were then placed on top of the PMA-differentiated THP1-blue™ cells. The apical compartment (containing Caco-2 cells) was filled with sterile-filtered (0.22 μm) colonic SHIME media (diluted 1:5 v/v in Caco-2 complete medium). Cells were treated apically with sodium butyrate (Sigma-Aldrich) as a positive control. The basolateral compartment (containing THP1-blue™ cells) was filled with Caco-2 complete medium. Cells were treated for 24 h, after which the TEER was measured. The basolateral supernatant was then discarded and cells were stimulated on the basolateral side with Caco-2 complete medium containing ultrapure lipopolysaccharide (LPS, E. coli K12, InvivoGen). Cells were also stimulated at the basolateral side with LPS in combination with hydrocortisone (HC, Sigma-Aldrich) and medium without LPS as controls. After LPS stimulation (6 h) the basolateral supernatants were collected for cytokine measurement (human IL-1β, IL-6, IL-8, IL-10, CXCL10 and MCP-1) by Luminex® multiplex (Affymetrix-eBioscience) and for NF-κB activity. All measurements were performed in triplicate and cells were incubated at 37° C. in a humidified atmosphere of air/C02 (95:5 v/v).

3. Results

Faecal samples were obtained from three healthy adult donors and used to establish three discrete gut models, each with a representative human microbiota. Following a two-week stabilization period and a further two-week control period, during which the donor microbiotas were established and vibrant, SYMPROVE™ was dosed daily over a three-week period into the M-SHIME® gut simulator. This exposed the bacteria to stomach acid conditions for 45 min (in vivo MRI imaging has shown that the half-emptying time for pure water (240 mL) in humans is 13±1 min) after which they transferred to small intestinal fluid for 180 min. The data in FIG. 1 show the total and viable cell counts following exposure to these phases; 99.3% of bacteria remained viable during this challenge. This indicates that the aqueous formulation of SYMPROVE™ protected the bacteria against the low gastric pH and the high concentrations of bile salts present in the small intestine, consistent with the results of earlier in vitro acid-tolerance testing. Following this period of exposure to gastric and small intestinal fluids, bacteria were transferred to the established microbiotas from three healthy adult donors.

FIG. 2 shows how the probiotic species colonised the luminal and mucosal compartments of the proximal and distal colons. L. acidophilus was not detected in the control samples, indicating it is not natively present in the human microbiota, and only appeared at a detectable level in the proximal colon after two weeks. It did not colonise the lumen of the distal colon, or the mucosal compartments of the proximal and distal colons, during the dosing period. This probably reflects the fact that during production of SYMPROVE™, L. acidophilus is added as a facilitator to aid the growth of L. rhamnosus and in the final product it is not present at greater than $10^4$ copies/mL. L. rhamnosus was also not detected in the control samples, but immediately colonised the luminal compartments upon dosing with SYMPROVE™, reaching ca. $10^6$ copies/mL in the proximal colon and ca. $10^7$ copies/mL in the distal colon after 1 week. It remained detectable at these concentrations throughout the rest of the dosing period. It also immediately colonised the mucosal compartment of the proximal colon, reaching $10^4$ copies/g but was never detected in the mucosal compartment of the distal colon. L. plantarum was sporadically detected in the lumen of the proximal colon during the control period but immediately colonised the luminal and mucosal compartments of the proximal ($10^8$ copies/mL luminal and $10^5$ copies/g mucosal) and distal ($10^7$ copies/mL luminal and $10^5$ copies/g mucosal) colons. E. faecium was abundantly present in all compartments during the control period, but its numbers increased upon dosing with SYMPROVE™ reaching approximately $10^8$ copies/mL in the luminal and approximately $10^6$ copies/g in the mucosal compartments.

Figure 3:
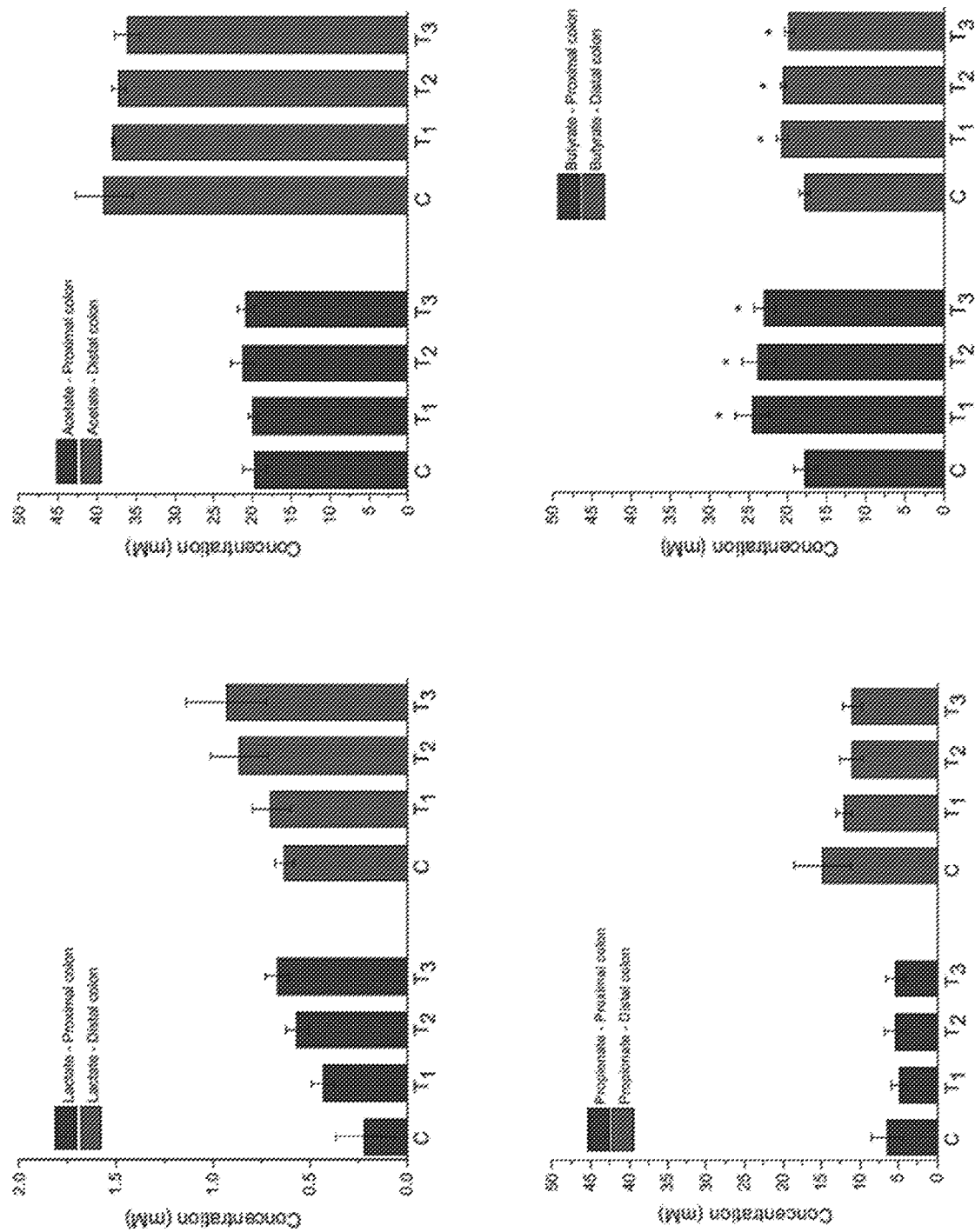
FIG. 3: Average SCFA and lactate concentrations±sd (n=3) in the luminal compartments of the proximal and distal colon of the three donors for the donor control samples (C) and following 1 week (T1), 2 weeks (T2) and 3 weeks (T3) daily dosing with SYMPROVE™. Lactate (top left), acetate (top right), propionate (bottom left) and butyrate (bottom right). Results that are of statistical significance compared with the control are indicated with * ($P<0.05$).

FIG. 3 reports the lactate and SCFA concentrations in the proximal and distal colon before and during dosing with SYMPROVE™. Concentrations of lactate rose after dosing with SYMPROVE™, and increased with continued dosing. Lactate is a major by-product of carbohydrate fermentation by lactobacilli and bifidobacteria but is also consumed by propionate-producing species, such as Veillonella and Megasphaera, and butyrate-producing species, such as A. caccae and E. hallii. Thus, the measured lactate concentrations are the net difference between production and consumption.

The SCFA data show that acetate is the most abundant (50.9% across the proximal and distal colon), followed by butyrate and propionate. This correlates with in-vivo data showing acetate comprises more than half the total SCFA detected in human faeces and arises because numerous bacterial groups, including bacteroidetes and acetogenic bacteria produce it as a by-product of saccharolytic fermentation. Acetate is itself a substrate for many butyrate-producing species, such as Faecalibacterium prausnitzii and Roseburia spp. and is an essential co-substrate that needs to be consumed to complete butyrate synthesis from lactate or carbohydrate. Thus, as in the case of lactate, the concentration of acetate is the net difference between production and consumption. Propionate levels were variable in the donor microbiotas and were not significantly altered during dosing with SYMPROVE™.

Butyrate concentrations were significantly increased, relative to the control, in both the proximal and distal colons. Unlike acetate and lactate, butyrate is the end product of fermentation and so it is not consumed in the in-vitro gut model, but in-vivo butyrate is a major energy source for colonocytes (which utilise up to 90% of butyrate and high butyrate concentrations are generally linked with improved health (Tan et al., 2014, Rios-Covian et al., 2016).

Once carbohydrate is depleted the colonic microbiota will switch from saccharolytic fermentation to proteolytic fermentation of protein, resulting in production of ammonium, branched-chain fatty acids (BCFA, typically isobutyrate, 2-methylbutyrate and isovalerate) and various amines, phenols/indoles and sulphides; these compounds generally impair colon health and so their presence is undesirable.

FIG. 4 shows that dosing with SYMPROVE™ actually reduced both BCFA and ammonium levels compared with the control.

Figure 5:
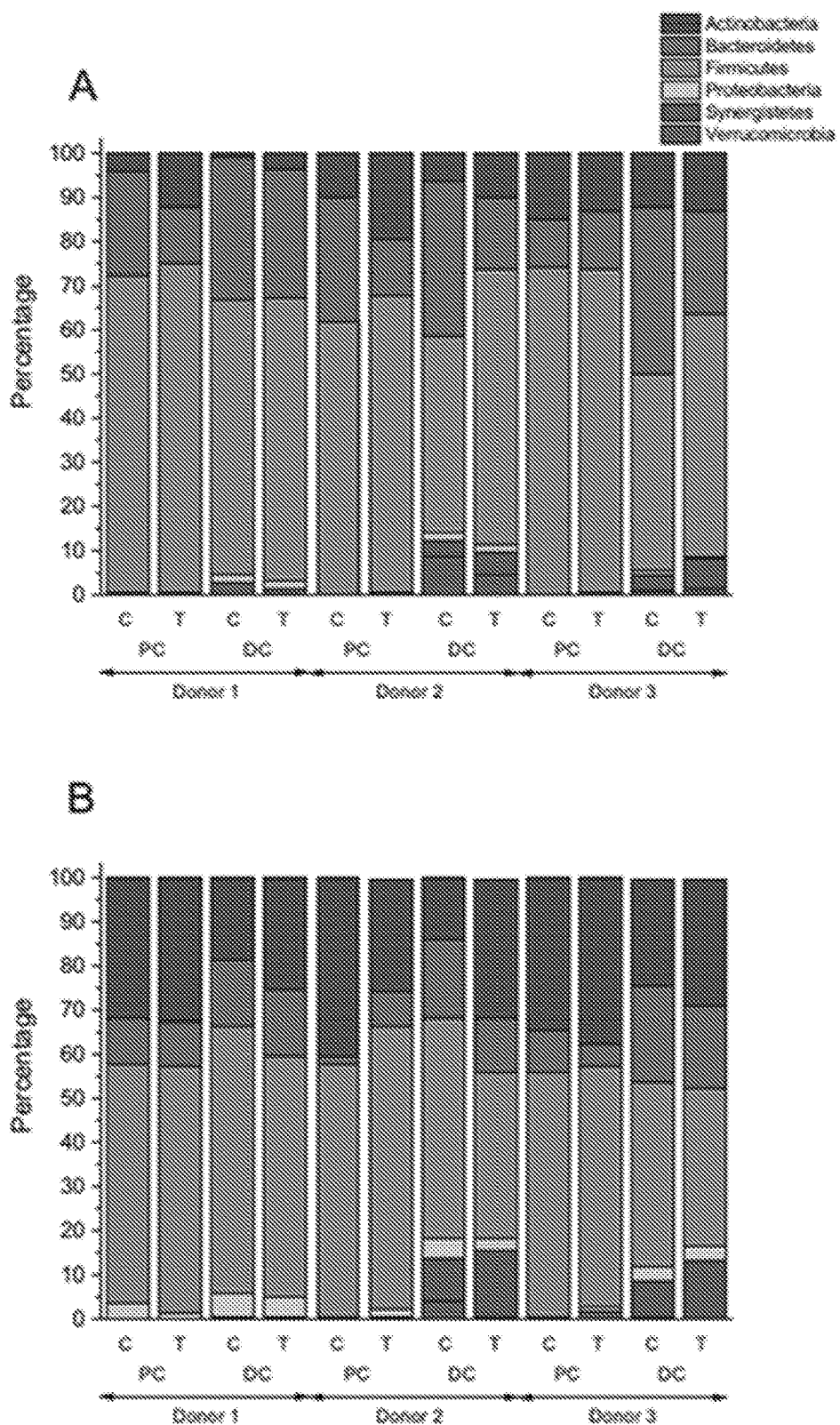
FIG. 5: Abundance (%) of the dominant phyla in the luminal (A) and mucosal (B) compartments of the proximal (PC) and distal (DC) colons at the end of the control (C) and treatment (T) periods for three human donors (n=1).

FIG. 5 shows the diversity of the gut microbiota, in terms of the six major phyla, for the three donors during the control and dosing periods (familial detail of operational taxonomic units (OTU) within phyla are given in FIGS. 6 and 7). In general, dosing with SYMPROVE™ enriched the proximal and distal luminal levels, and the distal mucosal level, of Actinobacteria of donors 1 and 2 at the expense of Bacteroidetes. In particular, *Bifidobacterium pseudocatenulatum* was increased in donors 1 and 2 and *Bifidobacterium adolescentis* was increased in donor 3, mainly at the expense of *Bifidobacterium longum*. For donors 2 and 3 there was also a marked increase in the mucosal numbers of *Bifidobacterium bifidum*. Bifidobacteria belong to the Actinobacteria, so the increase in this phylum could explain the higher acetate concentrations but also the higher butyrate concentrations, mediated to acetate-driven cross-feeding interactions with butyrate-producing bacteria discussed above, while the reduction in Bacteroidaceae could explain the low propionate concentrations. Luminal levels of Firmicutes increased in the proximal colon of donors 1 and 2 and in the distal colon of all three donors. At OTU level, the main changes were attributed to OTU 33 (*L. plantarum*) and OTU 125 (*L. rhamnosus*), reflecting successful colonisation by the probiotic bacteria in SYMPROVE™.

Ruminococcaceae numbers increased in all three donors, with OTU 64 (*F. prausnitzii*) numbers raised in donor 2 (and the mucosal compartments of all donors) and OTU 29 (*Subdoligranulum* spp.) in donors 1 and 3. Interestingly, Lachnospiraceae, a strongly butyrate-producing family, were suppressed in the mucosal compartments of all donors. Veillonellaceae numbers were increased for all donors but particularly for donor 2 (OTU 1, *Megasphaera* spp.). Many butyrate-producing bacteria belong to the Firmicutes, so the increase in proportion of this phylum also correlates with the raised butyrate levels discussed above. Other lactate-producing families that were enriched following dosing with SYMPROVE™ included Enterococcaceae in the luminal and mucosal proximal colon and luminal distal colon of donors 1 and 3, reflective of the wide colonisation by *E. faecium*, and Streptococcaceae in all compartments of all donors; these increases are manifest in the general increase in the Actinobacteria and Firmicutes phyla. Synergistetes colonised the distal colon of donors 2 and 3 and their numbers increased after dosing with SYMPROVE™.

Figure 8:
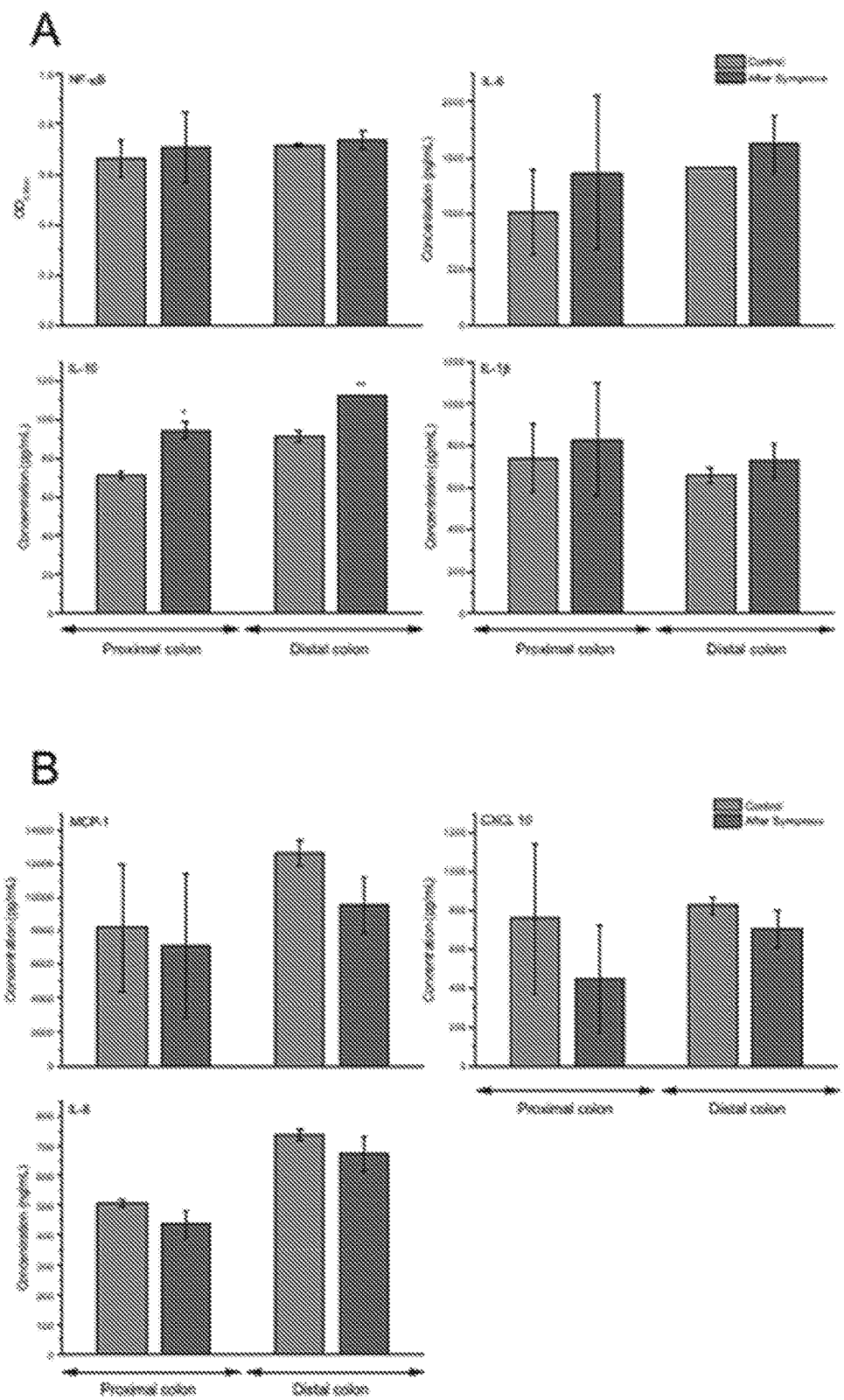
FIG. 8: Effect of SHIME samples (control and after dosing with SYMPROVE™) on the secretion of (A) anti-inflammatory cytokines (NF-κB, IL-6, IL-10 and IL-1β) and (B) inflammatory chemokines (MCP-1, CXCL 10 and IL-8). Results that are of statistical significance compared with the control are indicated with * ($P<0.05$) and ** ($P<0.01$).

A Caco-2-THP1-Blue™ co-culture in-vitro model was used to assess the inflammatory response of SHIME samples (control and after dosing with SYMPROVE™). Following dosing with SYMPROVE™, no reduction in transepithelial electrical resistance (TEER) was seen in the cell culture model, indicating integrity of the epithelium was maintained during experimentation. FIG. 8 shows the levels of the anti-inflammatory cytokines (NK-κB, IL-6, IL-10 and IL-1β) and inflammatory chemokines (MCP-1, CXCL 10 and IL-8). Dosing with SYMPROVE™ did not alter the levels of NF-κB or IL-1β, but increased the levels of IL-6 and IL-10 and decreased the levels of MCP-1, CXCL 10 and IL-8.

4. Discussion

The data reported here show that the probiotic species in SYMPROVE™ are capable of surviving the challenges of oral delivery under simulated human conditions. Exposure to stomach acid for 45 min and small-intestinal juice for 3 h did not significantly reduce viable bacterial numbers (99.3% viability). The primary factor in this stability is probably the fact that the bacteria are suspended in an aqueous wort, rather than in a freeze-dried compact/sachet or an oil-in-water emulsion (such as a yoghurt); in-vivo, consumption of water does not trigger production of stomach acid (which is primarily secreted to facilitate digestion of proteins by denaturing them and activating pepsinogen by converting it to pepsin). Indeed, ingestion of appreciable volumes of water will dilute gastric juice, raising local pH. Without fat, the stomach will empty water into the small intestine rapidly (the half-emptying time in humans is 13±1 min), where local pH rises again (the small intestine pH gradually increases along its length from ca. 5.6 to 7.4. Lactobacilli have been shown to have appreciable acid-tolerance; for instance, *L. acidophilus* strains remain viable at pH 3.5 while *L. rhamnosus* strains can remain viable for several hours at pH 3. When fat is a component of the ingested foodstuff, water empties at the same rate but the fat is retained for a longer period. When glucose is present above 6% w/v, gastric emptying is further delayed.

Following transit through the upper GIT, three of the probiotic bacteria (*L. plantarum, L. rhamnosus* and *E. faecium*) were able to establish, colonise and proliferate in the luminal and mucosal compartments of the proximal and distal colon while *L. acidophilus* was able to proliferate in the proximal lumen. Importantly, the data show that three of the probiotic species were able to colonise the mucosal layer. This suggests that in vivo consumption of SYMPROVE™ would lead to colonisation of the gut by the probiotic species, rather than the luminal numbers rising transiently, which helps to explain the positive, long-term effects seen during clinical studies. Proliferation occurred despite the existence of an established, and vibrant, microbiota, suggesting that the probiotic species were not out-competed by the commensal bacteria for nutrients.

Once established, the probiotics had a positive influence; the principal effect was caused through an increase in lactate concentration. Cross-feeding interactions from this substrate encouraged growth of commensal gut bacteria, particularly those of the Firmicutes phyla, leading to increased SCFA levels, especially butyrate.

Changes in composition of the microbiota was seen for all donors, although the specific changes varied, reflecting both the complexity and diversity of human gut flora. Broad changes in the gut microbiota have been linked with gut disease; for instance, reduced levels of Firmicutes and Actinobacteria are typically seen in IBS while reduced levels of Firmicutes and increased levels of Proteobacteria are typically seen in IBD.

As well as being produced by the *Lactobacillus* spp. in SYMPROVE™, numbers of bifidobacteria were also seen to increase and these are known to be lactate-producing. One possibility is that the wort used to produce and suspend the probiotic bacteria in SYMPROVE™ is itself a nutrient source for bifidobacteria, since it contains germinated barley extracts. Untreated barley has been shown to increase *Bifidobacterium* spp. and *Lactobacillus* spp., as well as increase butyrate concentrations, in growing pigs and in rats fed low-fat diets, while xylooligosaccharides from barley have been shown to increase *Lactobacillus* spp. in simulated GIT conditions. The increase in bifidobacteria numbers would in itself have a beneficial impact on general health; for instance, consumption of *B. bifidum* for 4 weeks modulated the microbiota in healthy adults, reducing the numbers of Prevotellaceae and *Prevotella*, increasing the numbers of Ruminococcaceae and Rikenellaceae and raising butyrate concentrations.

While acetate levels remained relatively constant throughout the control and dosing periods, raised concentrations of acetate were suggested by the increased proportion of acetate-producing bacteria (bifidobacteria, bacteroidetes and acetogenic bacteria), but since measured acetate concentrations always reflect the net difference between production and consumption, overall levels were not significantly increased.

Conversely, concentrations of butyrate were significantly higher, because this is the end-point of fermentation; in vivo, the majority of butyrate is utilized by but since these are not present in the in vitro gut model, butyrate accumulates in the luminal medium.

Since dysbiosis has been linked to a reduction in butyrate-producing species, the increase in butyrate seen here is expected to confer a positive clinical effect. Given the numerous positive effects of butyrate on human health, many attempts have been made to formulate butyrate supplements; unfortunately, butyrate has a strongly unpleasant odour, is largely absorbed in the upper GIT, and formulation of sodium butyrate in coated pellets proved unsuccessful in modulating gut function in rats. The data presented here suggest that a properly formulated probiotic supplement may be a better approach, stimulating the existing microbiota to produce butyrate rather than supplying it as a dietary supplement.

The effect of probiotics on modulating inflammatory responses may also contribute to their clinical effectiveness. Here, the in-vitro cell culture model showed no degradation in the integrity of the epithelial barrier, as well as reduced markers of inflammation, when exposed to SHIME media following dosing with SYMPROVE™. Levels of the anti-inflammatory cytokines NK-κB and IL-1β were unchanged, while IL-6 was increased and IL-10 was significantly increased. Concomitantly, levels of the inflammatory chemokines MCP-1, CXCL 10 and IL-8 were reduced.

5. Summary

The data show that when a probiotic suspension is formulated in such a way as to address the challenges of oral delivery in humans, then viable probiotic species can be delivered to the gut. Once there, the bacteria can infiltrate, colonise and proliferate in the luminal and mucosal compartments. It is important to remember that the cell culture model described herein means it is the change in the microbiota as a whole that is modulating the immune response. This is a critical distinction; the World Health Organisation definition, which requires probiotics to "confer a health benefit on the host", is often incorrectly interpreted as meaning it must be demonstrated that the probiotic species itself must by some metabolic mechanism cause a positive effect in-vivo. The data presented here clearly suggest that in fact integration and colonisation of the probiotic species within the existing microbiota, and the generation of a utilizable nutrient (lactate), stimulates growth of the largely beneficial phyla meaning that it is the rebalancing of bacterial families that confers health benefits to the host. This rebalancing effect is seen here even though the microbiota were obtained from three healthy donors; since many gut diseases, as noted above, are linked to dysbiosis it seems likely that the mechanism of rebalancing is the major cause of improvement in clinical symptoms, rather than any effect from an individual probiotic species.

It is notable also the data show no negative influences on gut health. Previous work has shown that *Lactobacillus* spp. and *Bifidobacterium* spp. can exert anti-pathogenic action against *Clostridium difficile*. Thus, delivery of these probiotic species may offer an alternative treatment option for patients with recurrent gut infections, before more radical measures such as faecal microbiota transplant.

Example 2

Further experiments were performed to investigate the effects of SYMPROVE™ on gut microbiota from patients suffering from severe liver cirrhosis or from early onset Parkinson's Disease (PD). Experiments were also performed on gut microbiota from patients having inflammatory bowel disease (IBD), which is known to be treated by SYMPROVE™.

The pathology of liver cirrhosis and PD is not typically associated with the gut bacterial populations of the patients. Nevertheless, as shown in the data below, both PD and cirrhosis patients exhibit gut dysbiosis. Additionally, different dysbiotic changes are observed between the two conditions. Accordingly, the data presented demonstrates the ability of SYMPROVE™ to promote rebalancing of a dysbiotic gut microbiota to a more healthy state across a variety of dysbiotic states and disease conditions.

2. Materials and Methods

A short-term assay using the M-SHIME® system described in Example 1 was performed using a bacterial inoculum obtained faecal samples from patients having PD, liver cirrhosis, or IBD (3 donors per disease, run in parallel). This involves fermentation of faecal samples in single vessels in the presence or absence of the probiotic bacteria in SYMPROVE™ Briefly, a sugar-depleted nutritional medium (56 mL) buffered at pH 6.5, containing the basal nutrients present in the colon (5.9 g/L $K_2HPO_4$, 18.3 g/L $KH_2PO_4$, 2.3 g/L $NaHCO_3$, 2.3 g/L yeast extract, 2.3 g/L peptone, 0.6 g/L cysteine and 2.3 ml/L Tween80) was co-administered with 7 ml SYMPROVE™ at the start of fermentation. A corresponding series of blank experiments were conducted by adding the basal nutritional medium to distilled water (7 mL, instead of SYMPROVE™). Comparison of the blank data with the SYMPROVE™ data allowed the effects of the probiotic formulation to be determined. A 7.5% (w/v) faecal suspension was prepared from each donor in anaerobic phosphate buffer ($K_2HPO_4$ 8.8 g/L; $KH_2PO_4$ 6.8 g/L; sodium thioglycolate 0.1 g/L; sodium dithionite 0.015 g/L) and was inoculated (7 mL) into the reactors, bringing the total volume to 70 mL. Finally, five mucin-covered microcosms were added to all colonic vessels, enabling maintenance of not only a luminal microbiota but also a specific mucosal microbiota in the colonic regions. Each incubation was performed in triplicate, resulting in 18 independent incubations. Incubations were performed for 48 h at 37° C., under shaking (90 rpm) and anaerobic conditions. The incubations were performed in fully independent closed reactors with sufficiently high volume (70 mL) in order to not only allow for a robust microbial fermentation, but also to allow the collection of multiple samples over time. Each incubation was performed in triplicate to account for biological variation, resulting in 54 independent incubations (9 donors, blank and treatment per donor, triplicate).

At the start of the short-term colonic incubation, the test ingredient was added to sugar depleted nutritional medium containing basal nutrients present in the colon (e.g. hostderived glycans such as mucin) in a concentration corresponding with a double dose of the product. A blank, containing only the sugar-depleted nutritional medium (without fibers), was also included for each donor, thus allowing assessment of the background activity of the bacterial community.

As well as measuring SCFA, BCFA and ammonium production, changes in microbiota composition were also assessed by 16S rRNA analysis. An Illumina PCR-based sequencing method was used, where microbial sequences are amplified until a saturation level is reached. Therefore, the results are expressed at different phylogenetic levels (microbial phylum, family, genus and OTU level) and presented as proportional values versus the total amount of sequences within each sample, thus providing semi-quantitative results. The methodology applied involves primers that span 2 hypervariable regions (V3-V4) of the 16S rDNA, using a pair-end sequencing approach, whereby sequencing of 2×250 bp results in 424 bp amplicons.

Additionally, a Caco-2/THP1 co-culture assay was performed as described above. Briefly, Caco-2 cells (HTB-37; American Type Culture Collection) were seeded in 24-well semi-permeable inserts. Caco-2 monolayers were cultured for 14 days, with three medium changes a week, until a functional cell monolayer with a transepithelial electrical resistance (TEER) was obtained. Cells were maintained in Dulbecco's Modified Eagle Medium (DMEM) containing glucose and L-glutamine and supplemented with HEPES and 20% (v/v) heat-inactivated (HI) fetal bovine serum (FBS). Cells were incubated at 37° C. in a humidified atmosphere of air/C02 (95:5, v/v).

THP1-Blue™ (InvivoGen) cells were maintained in Roswell Park Memorial Institute (RPMI) 1640 medium containing glucose and glutamine, supplemented with HEPES, sodium pyruvate and 10% (v/v) HI-FBS. THP1-Blue™ are THP1 human monocytes stably transfected with a reporter construct expressing a secreted alkaline phosphatase (SEAP) gene under the control of a promoter inducible by the transcription factor nuclear factor kappa B (NF-κB). Upon TLR activation (e.g. by lipopolysaccharide (LPS); isolated from Gram-negative bacteria), NF-κB becomes activated and induces the expression and secretion of SEAP. SEAP activity can then be measured in the supernatants by using the QUANTI-Blue reagent (InvivoGen). THP1-Blue™ cells were seeded in 24-well plates and treated with PMA that induces the differentiation of the cells into macrophage-like cells, which are able to adhere and are primed for TLR signaling. Cells were incubated at 37° C. in a humidified atmosphere of air/C02 (95:5, v/v).

For the co-culture, the TEER of the Caco-2 monolayers was measured (=0 h time point). The TEER of an empty insert was subtracted from all readings to account for the residual electrical resistance of an insert. Then, the Caco-2-bearing inserts were placed on top of the PMA-differentiated THP1-Blue™ cells for further experiments, as previously described 4, 11. Briefly, the apical compartment (containing the Caco-2 cells) was filled with sterile-filtered (0.22 μm) colonic SHIME suspensions. Cells were also treated apically with Sodium butyrate (NaB) (Sigma-Aldrich) as positive control. The basolateral compartment (containing the THP1-Blue™ cells) was filled with Caco-2 complete medium.

Cells were also exposed to Caco-2 complete medium in both chambers as control. Cells were treated for 24 h, after which the TEER was measured (=24 h time point). After subtracting the TEER of the empty insert, all 24 h values were normalized to its own 0 h value (to account for the differences in initial TEER of the different inserts) and are presented as percentage of initial value. Then, the basolateral supernatant was discarded and cells were stimulated at the basolateral side with Caco-2 complete medium containing ultrapure LPS (*Escherichia coli* K12, InvivoGen). Cells were also stimulated at the basolateral side with LPS in combination with hydrocortisone (HC) (Sigma-Aldrich) and medium without LPS (LPS−) as controls. After LPS stimulation, the basolateral supernatants were collected for cytokine measurement (IL-6, IL-8, IL-10, TNF-α, CXCL10 and MCP-1 by Luminex® multiplex (Affymetrix-eBioscience)) and for NF-κB activity, according to the manufacturers' instructions. All treatments were done in biological triplicate. Cells were incubated at 37° C. in a humidified atmosphere of air/C02 (95:5, v/v).

Additionally, a scratch assay was performed to assess the ability of SYMPROVE™ to promote intestinal epithelial barrier repair. The in vitro scratch wound healing assay was performed using T84 cells (Sigma-Aldrich) that were seeded in 24-well plates and cultured for 7 days, with three medium changes a week, until a complete confluent cell monolayer was formed. Cells were maintained in Dulbecco's Modified Eagle's Medium/Nutrient Mixture F-12 Ham containing L-glutamine and HEPES and supplemented with Antibiotic-Antimycotic and 5% HI-FBS. Cells were incubated at 37° C. in a humidified atmosphere of air/C02 (95:5, v/v).

After 7 days of culture, a scratch was created in a T84 cell monolayer, followed by treatment with ⅒ diluted colonic batch suspensions in serum-free T84 culture medium. Images were captured using the Cytation 5 Cell Imaging Multi-Mode Reader at the initial timepoint (0 h) and after 24 h incubation.

Images were compared to quantify the migration rate of the cells, and the wound area was measured using ImageJ®. Serum-free culture medium and 5 mM NaB (Sigma-Aldrich) were used as negative and positive control respectively. All treatments were done in biological triplicate. Cells were incubated at 37° C. in a humidified atmosphere of air/C02 (95:5, v/v).

3. Results 3.1 SCFA Production
Liver Cirrhosis

Figure 9A:
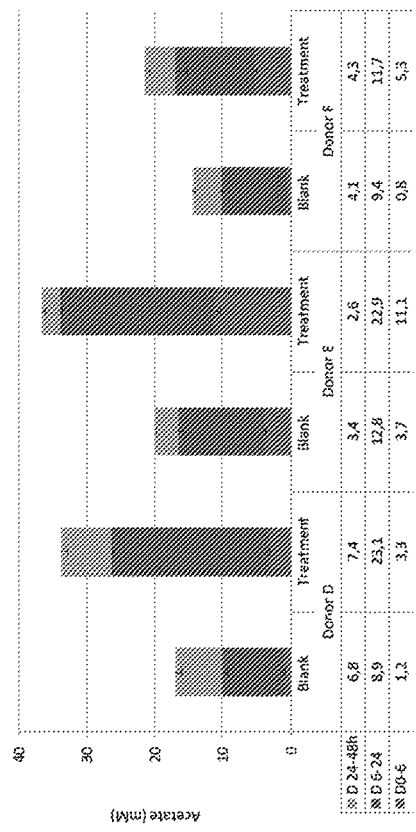
FIG. 9: (A) Total SCFA production (±STDEV) during different time-intervals (0-6 h, 6-24 h and 24-48 h) of the 48 h incubation with SYMPROVE™, using gut microbiota from three liver cirrhosis patients. For each donor a negative control (blank) (n=3) was included. (B) Acetate production (±STDEV) during different time-intervals (0-6 h, 6-24 h and 24-48 h) of the 48 h incubation with SYMPROVE™, using gut microbiota from three liver cirrhosis patients. For each donor a negative control (blank) (n=3) was included. (C) Propionate production (±STDEV) during different time-intervals (0-6 h, 6-24 h and 24-48 h) of the 48 h incubation with SYMPROVE™, using gut microbiota from three liver cirrhosis patients. For each donor a negative control (blank) (n=3) was included. (D) Butyrate production (±STDEV) during different time-intervals (0-6 h, 6-24 h and 24-48 h) of the 48 h incubation with SYMPROVE™, using gut microbiota from three liver cirrhosis patients. For each donor a negative control (blank) (n=3) was included.

Addition of SYMPROVE™ had a stimulatory effect on the gut microbiota of the three liver cirrhosis donors in terms of SCFA production (FIG. 9A). SCFA production mainly took place during the 6-48 h timeframe. Overall, the strongest stimulatory effect of SYMPROVE™ was observed for donors E and D, yielding a 28.0 mM and 26.9 mM higher SCFA concentration than the corresponding blanks respectively.

Figure 9B:
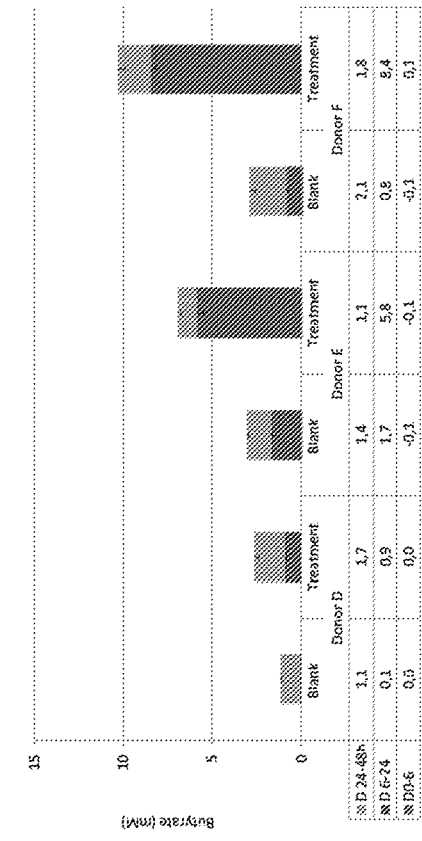

Addition of SYMPROVE™ had a stimulatory effect on acetate production in the three liver cirrhosis donors (FIG. 9B). Donor E was characterized by a strong production of acetate already during the first 6 h, clearly stimulated by SYMPROVE™. Overall, production of acetate mainly took place during the 6-24 h timeframe. Treatment with SYMPROVE™ was associated with increased acetate concentrations most apparent in donors D (16.9 mM higher concentration in treatment versus blank) and E (16.7 mM higher concentration).

Figure 9C:
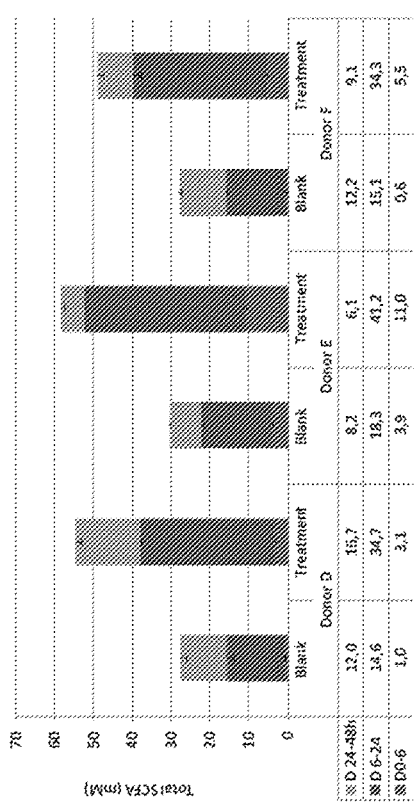

Addition of SYMPROVE™ had a stimulatory effect on propionate production in the incubations with the three liver cirrhosis donors (FIG. 9C). Propionate production took place during the 6-48 h timeframe, yielding the highest concentrations after 48 h for donor D. The strongest stimulatory effect of SYMPROVE™ was also observed for donor D, yielding an 8.8 mM higher propionate concentration than the corresponding blank.

Figure 9D:
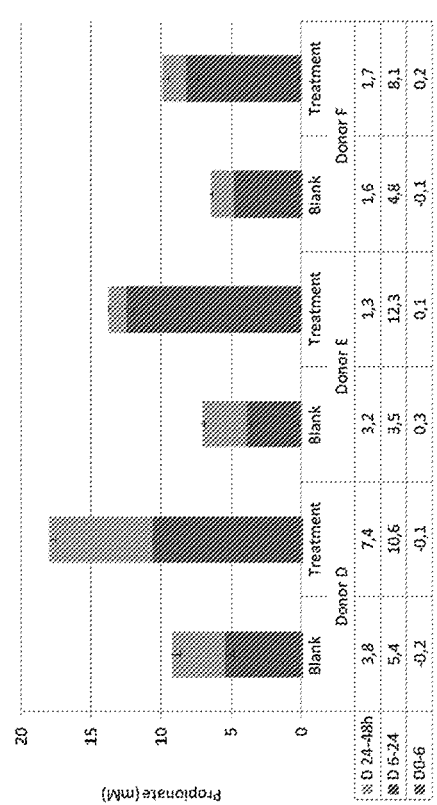

Production of butyrate was stimulated by the addition of SYMPROVE™ in all donors, especially in donors E and F (FIG. 9D). The highest butyrate concentration after 48 h was obtained for donor F, possibly due to conversion of acetate, thus explaining the lower acetate concentrations (FIG. 9B). Addition of SYMPROVE™ increased the production of butyrate with 7.5 mM for donor F and with 3.9 mM for donor E.

Parkinson's Disease

Figure 10A:
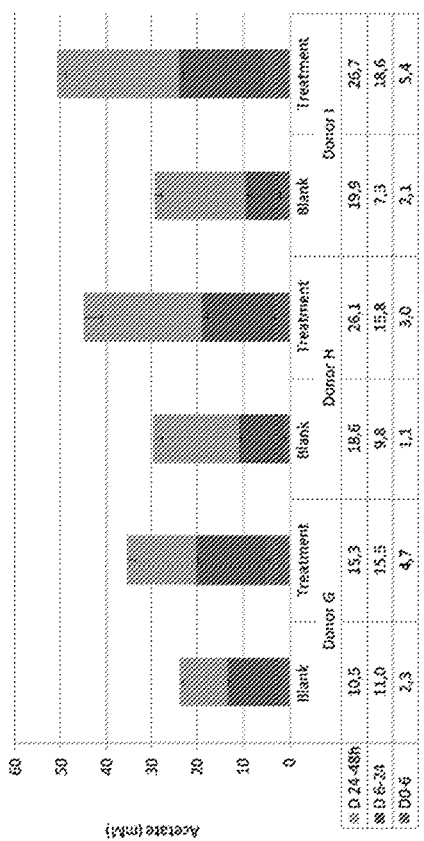
FIG. 10: (A) Total SCFA production (±STDEV) during different time-intervals (0-6 h, 6-24 h and 24-48 h) of the 48 h incubation with SYMPROVE™, using gut microbiota from three Parkinson's patients. For each donor a negative control (blank) (n=3) was included. (B) Acetate production (±STDEV) during different time-intervals (0-6 h, 6-24 h and 24-48 h) of the 48 h incubation with SYMPROVE™, using gut microbiota from three Parkinson's patients. For each donor a negative control (blank) (n=3) was included. (C) Propionate production (±STDEV) during different time-intervals (0-6 h, 6-24 h and 24-48 h) of the 48 h incubation with SYMPROVE™, using gut microbiota from three Parkinson patients. For each donor a negative control (blank) (n=3) was included. (D) Butyrate production (±STDEV) during different time-intervals (0-6 h, 6-24 h and 24-48 h) of the 48 h incubation with SYMPROVE™, using gut microbiota from three Parkinson's patients. For each donor a negative control (blank) (n=3) was included.

Addition of SYMPROVE™ had a stimulatory effect on the gut microbiota of the three Parkinson's donors in terms of SCFA production (FIG. 10A). SCFA production mainly took place during the 6-48 h timeframe. Overall, the strongest stimulatory effect of SYMPROVE™ was observed for donors H and I, yielding a 27.8 mM and 28 mM higher SCFA concentration than the corresponding blanks respectively.

Figure 10B:
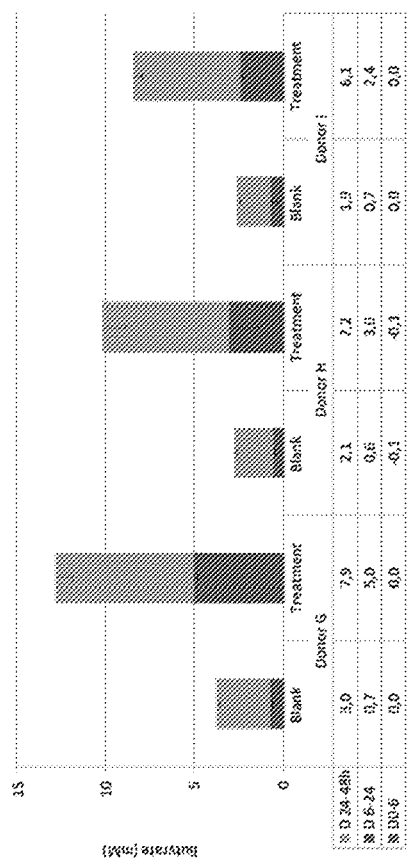

Addition of SYMPROVE™ had a stimulatory effect on acetate production in the three Parkinson's donors (FIG. 10B), mainly during the 6-48 h timeframe. This stimulation resulted in significantly higher acetate concentrations in the treatments than the blanks. The strongest stimulation was observed in donor I (yielding a 21.4 mM higher acetate concentration in the treatment). In all three donors, a significant amount of acetate was produced during the 24-48 h timeframe, illustrating that substrates had not been depleted after 24 h.

Figure 10C:
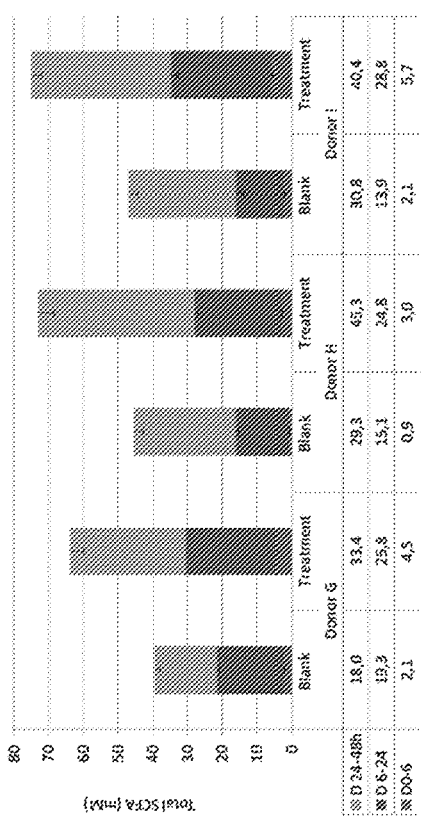

Addition of SYMPROVE™ had a stimulatory effect on propionate production in the incubations with two of the three Parkinson's donors (G and H) (FIG. 10C). Propionate production took place during the 6-48 h timeframe, but the stimulatory effect was exerted during the 24-48 h timeframe. The highest propionate concentration after 48 h and the strongest stimulatory effect of SYMPROVE™ was obtained for donor H, yielding 5.9 mM more propionate than the corresponding blank.

Figure 10D:
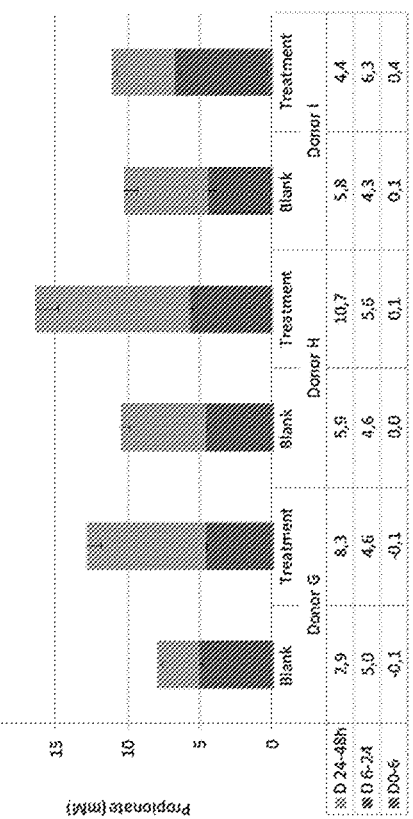

SYMPROVE™ stimulated butyrate production in the three donors (FIG. 10D). The stimulatory effect was clear already after 24 h and continued during the 24-48 h timeframe. The highest butyrate concentration after 48 h was obtained in the treatment incubation with donor G, increasing butyrate levels with 9.1 mM compared to the blank. Addition of SYMPROVE™ increased the production of butyrate with 7.5 mM for donor H and with 5.9 mM for donor I.

Lactate concentrations rose substantially after 6 h and then fell during the rest of the test. Lactate is the first compound to increase in concentration because of carbohydrate fermentation by the lactic-acid bacteria in SYMPROVE™; however, lactate does not actually accumulate in the system because it is consumed by propionate-producing species, such as *Veillonella* and *Megasphaera*, and butyrate-producing species, such as *Anaerostipes caccae* and *E. hallii*.

In addition, SYMPROVE™ decreased branched CFA concentrations (isobutyrate, isovalerate and 2-methylbutyrate) compared to the control incubations in the three tested PD donors. With respect to ammonium production, it was found that SYMPROVE™ lowered ammonium concentrations compared to the control incubations for the three donors.

it is a general characteristic of the microbiota of patients with PD that short-chain fatty acid (SCFA) producing bacteria are reduced in number so the raised SCFA levels seen here following dosing with probiotic bacteria is an encouraging sign from the perspective of treating patients with PD.

IBD

Figure 11A:
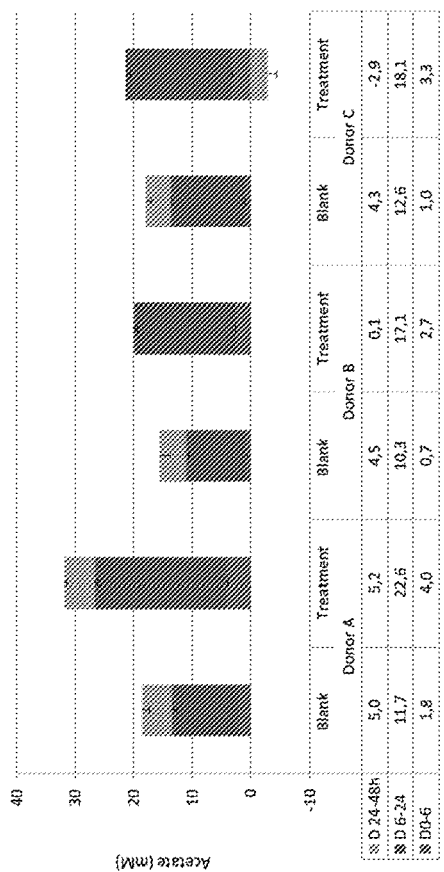
FIG. 11: (A) Total SCFA production (±STDEV) during different time-intervals (0-6 h, 6-24 h and 24-48 h) of the 48 h incubation with SYMPROVE™, using gut microbiota from three IBD patients. For each donor a negative control (blank) (n=3) was included. (B) Acetate production (±STDEV) during different time-intervals (0-6 h, 6-24 h and 24-48 h) of the 48 h incubation with SYMPROVE™, using gut microbiota from three IBD patients. For each donor a negative control (blank) (n=3) was included. (C) Propionate production (±STDEV) during different time-intervals (0-6 h, 6-24 h and 24-48 h) of the 48 h incubation with SYMPROVE™, using gut microbiota from three IBD patients. For each donor a negative control (blank) (n=3) was included.

Addition of SYMPROVE™ had a stimulatory effect on production of SCFA (FIG. 11A). SCFA production is reflective of the overall fermentation of test ingredients. Production of SCFA started during the 6-24 h timeframe, yielding the highest concentrations after 24 h for donor A, and continued during the 24-48 h timeframe. At the end of the incubation, the highest SCFA concentrations were obtained for the treatment of donor A. The strongest stimulatory effect of SYMPROVE™ was also observed for donor A, yielding a 25.3 mM higher SCFA concentration than the corresponding blank.

Figure 11B:
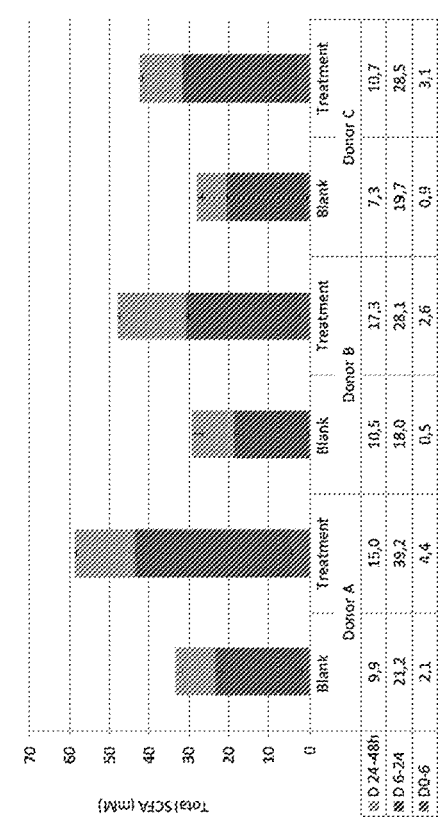

Addition of SYMPROVE™ had a stimulatory effect on acetate production in the incubations with the three IBD donors (FIG. 11B). Production during the first 6 h of incubation was rather low; it mainly took place during the 6-24 h timeframe. The highest concentrations after 24 h were obtained for donor A. Acetate production for this donor further continued during the 24-48 h timeframe, yielding the highest acetate concentrations amongst the three donors at the end of the incubation. The strongest stimulatory effect of SYMPROVE™ was also observed for donor A, yielding a 13.3 mM higher acetate concentration than the corresponding blank.

In the treatment incubation with donor C, acetate was consumed during the 24-48 h timeframe. Consumption of acetate is indicative of cross-feeding between members of the community.

Figure 11C:
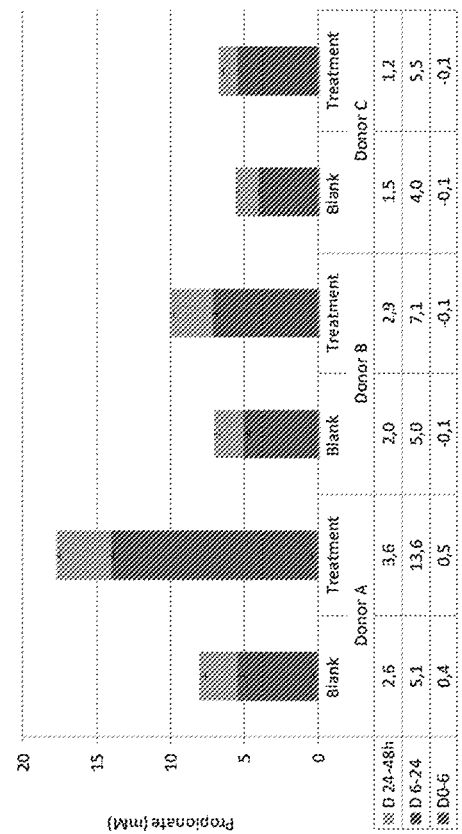

Addition of SYMPROVE™ had a stimulatory effect on propionate production in the incubations with the three IBD donors (FIG. 11C). Production did not occur during the first 6 h of incubation, but took place during the 6-48 h timeframe. The highest concentrations after 48 h were obtained for donor A. The strongest stimulatory effect of SYMPROVE™ was also observed for donor A, yielding a 9.7 mM higher propionate concentration than the corresponding blank.

Butyrate was not produced during the first 6 h of incubation. Considering that butyrate production depends on the primary production of acetate and/or lactate, it is typically produced at a later stage of the incubation. Production of butyrate started during the 6-24 h timeframe, yielding higher concentrations in the treatments than in the blank after 48 h and thus indicating the stimulatory effect of SYMPROVE™ on butyrate production. The highest butyrate concentrations were obtained for donors B and C, yielding 10.9 mM and 12.6 mM more butyrate than their corresponding blanks respectively.

For all 3 disease conditions, a strong increase in lactate production was observed in the first 6 hours of incubation, followed by a decrease in lactate concentration from hours 6 to 48. This is indicative of cross-feeding interactions characterised by conversion of the lactate to butyrate and/or propionate, borne out by the observed increases in these SCFAs.

3.2 Changes in Microbiota Composition

The microbiota from the 3 different groups was compared prior to any treatment. The 16S-data showed:

Relative abundance of Actinobacteria was significantly higher in patients with liver cirrhosis (average 35.0%) compared to patients with Parkinson disease (average 7.7%). This was mainly attributed to the strong representation of Bifidobacteriaceae (average 27.4% versus 2.5% for PD).

Relative abundance of Bacteroidetes was significantly higher in patients with PD (average 19.0%) compared to patients with IBD (average 13.0%). At family level this was mainly attributed to Muribaculaceae, which were only represented in the gut microbiota of PD patients.

Relative abundance of Firmicutes was significantly lower in liver cirrhosis patients (42.5%) compared to the other two diseases (69.0% in IBD and 70.3% in PD). At family level this was mainly attributed to Ruminococcaceae (average 9.5% abundance in liver cirrhosis patients versus 15.6% in IBD and 24.2% in Parkinson), and Lachnospiraceae (average 19.0% in liver cirrhosis patients versus 40.3% in IBD and 32.8% in PD).

Relative abundance of Verrucomicrobia was significantly higher in patients with PD (0.4%), compared to patients with liver cirrhosis (0.1%). At family level, these differences were attributed to Akkermansiaceae and Puniceicoccaceae.

Liver Cirrhosis

OTU20 (*Lactobacillus plantarum*) and OTU21 (*Lactobacillus rhamnosus*), both probiotic species contained in the SYMPROVE™ product, were significantly enriched in the juminal and mucosal environments of donors D and E (FIG. 12), suggesting that these probiotic strains were able to proliferate well in presence of the gut microbiota of liver cirrhosis patients.

Treatment with SYMPROVE™ consistently resulted in an enrichment of Actinobacteria in both the lumen and the mucus environments of the three tested donors. While the enrichment was mainly due to stimulation of Bifidobacteriaceae (FIG. 13), the responsible OTUs differed between the donors (Table 8). OTU5 (*Bifidobacterium longum*) and OTU30 (*Bifidobacterium adolescentis*) were found to be significantly stimulated by SYMPROVE™ in all three donors (FIG. 12).

The treatment also strongly enriched the Firmicutes population in the lumen of the three donors. This stimulatory effect was statistically significant in all donors and was mainly dedicated to Lactobacillaceae and Veillonellaceae (FIG. 13). In the mucus environment, Lachnospiraceae and Lactobacillaceae were consistently stimulated by the treatment. OTU28 (*Veillonella* sp.) was consistently enriched in the lumen of the three donors; OTU11 and OTU12 (both *Clostridium* XIVa sp.) were consistently enriched in the mucus environment of the three donors (FIG. 12). SYMPROVE™ tended to have a stimulatory effect on Proteobacteria in the mucus environment, while it lowered their relative abundance in the luminal environment.

Finally, the relative abundance of Bacteroidetes decreased in lumen and mucus upon treatment with SYMPROVE™, regardless of the donor.

Parkinson's Disease

OTU20 (*Lactobacillus plantarum*) and OTU21 (*Lactobacillus rhamnosus*), both probiotic species of the SYMPROVE™ product, were significantly enriched in the luminal and mucosal environments of the three donors (FIG. 14). Besides these, OTU22 (*Enterococcus faecium*), also a probiotic species of SYMPROVE™, was significantly enriched in the luminal and mucosal environments of donor I (FIG. 14), suggesting that aforementioned probiotic strains were able to proliferate well in presence of the gut microbiota of PD patients.

Treatment with SYMPROVE™ consistently resulted in an enrichment of Actinobacteria in both the lumen and the mucus environments of the three tested donors. In all cases, the effect was statistically significant. The enrichment was due to a stimulation of Bifidobacteriaceae (FIG. 15), more specifically of OTU5, identified as closely related to *Bifidobacterium longum* (FIG. 14).

The treatment strongly enriched the Firmicutes population in the lumen of the three donors and in the mucus environment of donors G and H. In the lumen, the stimulatory effect was dedicated to Eubacteriaceae, Lachnospiraceae, Lactobacillaceae, Streptococcaceae and Veillonellaceae in the three donors (FIG. 15). The strongest enrichments in the mucus environment were observed for Erysipelotrichaceae, Lachnospiraceae and Veillonellaceae, but inter-individual differences were observed (FIG. 15). OTU11, OTU12 (both *Clostridium* XIVa sp.), OTU7 (*Veillonella parvula/dispar*) were significantly enriched in the luminal and mucosal environments of the three donors (FIG. 14).

As mentioned above, the decrease in relative abundance of a bacterial population may have been due to outgrowth of another bacterial population; in this particular case, for instance, Firmicutes, Actinobacteria and Proteobacteria.

IBD

OTU20 (*Lactobacillus plantarum*) and OTU21 (*Lactobacillus rhamnosus*), both probiotic species contained in the SYMPROVE™ product, were significantly enriched in the lumen and mucus environments of the three donors (FIG. 16), suggesting that these probiotic strains were able to proliferate well in presence of the gut microbiota of IBD patients.

Treatment with SYMPROVE™ consistently increased Actinobacteria levels in the lumen of the three tested donors. At family level, enrichment was mainly due to Bifidobacteriaceae (FIG. 17). No OTUs of this bacterial family were significantly enriched in all three donors (FIG. 16), illustrating that the response to the treatment in terms of stimulation of specific bacterial groups was donor dependent. For instance, OTU5 (*B. longum*) was significantly enriched in donor C, while in donor B OTU56 (*B. pseudolongum*) was responsible for the observed stimulation.

Further, SYMPROVE™ treatment consistently stimulated the Firmicutes population in the mucus of the three donors. Enrichment was dedicated to Lachnospiraceae, and to a lesser extent to Lactobacillaceae, Streptococcaceae and Veillonellaceae (FIG. 17). In the lumen, only Lactobacillaceae were significantly enriched in the three donors. *Roseburia* species (OTU13 for donors A/B and OUT 44 for donor C) were significantly enriched in the mucus layer of the three donors (FIG. 16).

SYMPROVE™ tended to have a mild stimulatory effect on Proteobacteria in the mucus environment of the three donors, while it lowered their relative abundance in the luminal environment. The stimulatory effect was mostly due to Enterobacteriaceae in donors A and B and due to Burkholderiaceae in donors B and C (FIG. 17). The lowering effect in the luminal environment was mainly dedicated to Burkholderiaceae in donor C (OTU52, Parasutterella excrementihominis) and to Enterobacteriaceae (OTU1, *Escherichia coli*) in donors A and B (FIG. 17).

3.3 Caco-2/TH P1-Blue™ Co-Culture

Liver Cirrhosis

Figure 18:
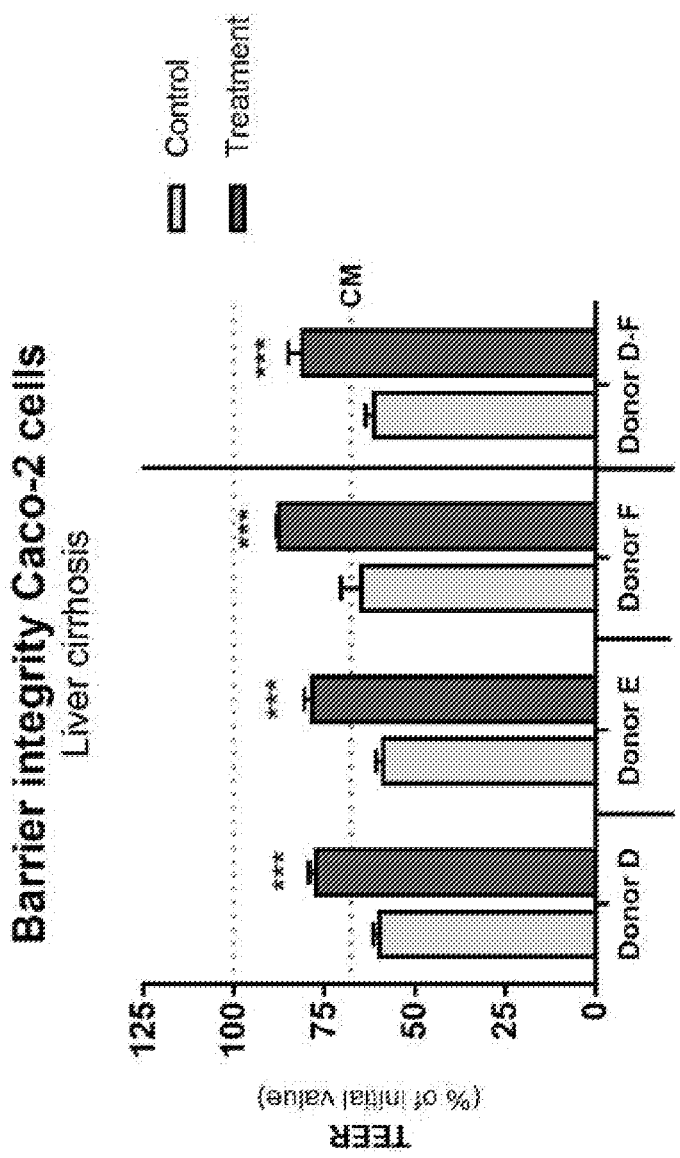
FIG. 18: Effect of colonic batch samples on transepithelial electrical resistance (TEER) of the Caco-2/THP1-Blue™ cocultures. TEER was measured 24 h after treatment of the co-cultures and each 24 h value was normalized to its corresponding 0 h value and is shown as percentage of initial value. The grey dotted line represents 100% (initial value). The red dotted line corresponds to the experimental control CM (complete medium). Data are plotted as mean±SEM. (*) represents statistically significant differences between the treatment and control samples. (***)=p<0.001. Data are represented for each donor separately and as the mean of all donors (Donor D-F).

Colonic samples of all liver cirrhosis donors following SYMPROVE™ treatment increased the TEER of the co-culture significantly compared to their control, while the TEER of the control samples even decreased slightly compared to the experimental control CM (FIG. 18). It can therefore by concluded that SYMPROVE™ colonic batch treatment samples of liver cirrhosis patients had a significant positive effect on the intestinal epithelial barrier function and integrity.

When assessing the inflammatory response following LPS stimulation, liver cirrhosis colonic samples following SYMPROVE™ treatment promoted a more anti-inflammatory/tolerigenic response compared to controls.

Figure 19:
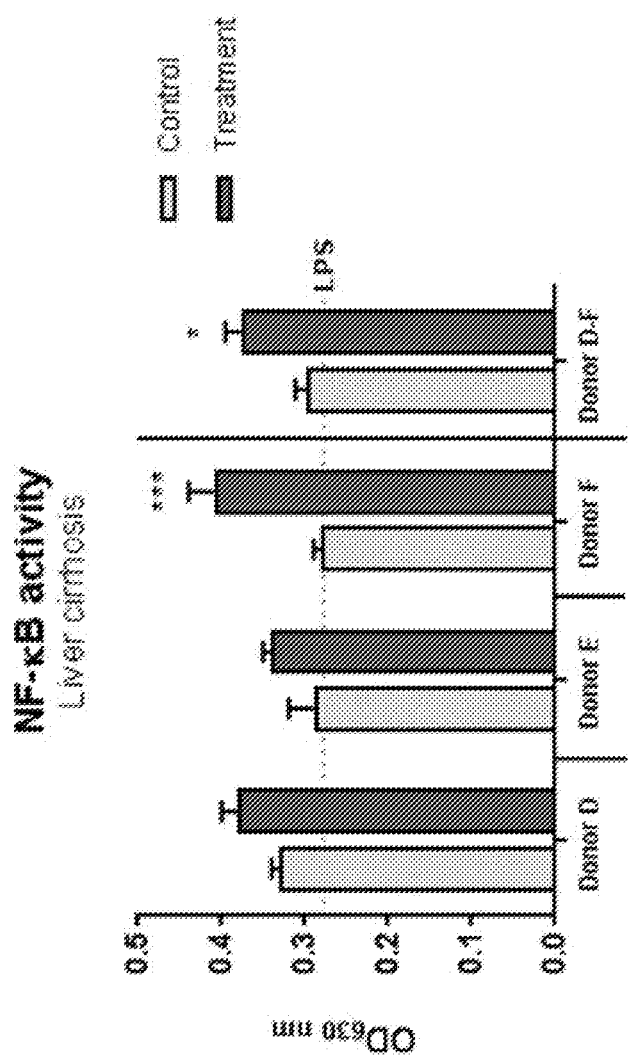
FIG. 19: Effect of colonic batch samples on NF-kB activity of THP-1-Blue™ cells. NF-kB activity levels were measured 6 h after LPS treatment on the basolateral side of the Caco-2/THP-1-Blue™ co-cultures after pre-treatment of the apical side for 24 h with the colonic batch samples. The dotted line corresponds to the experimental control LPS+. Data are plotted as mean±SEM. (*) represents statistically significant differences between the treatment and control samples. (*)=p<0.05; (***)=p<0.001. Data are represented for each donor separately and as the mean of all donors (Donor D-F).
Figure 20:
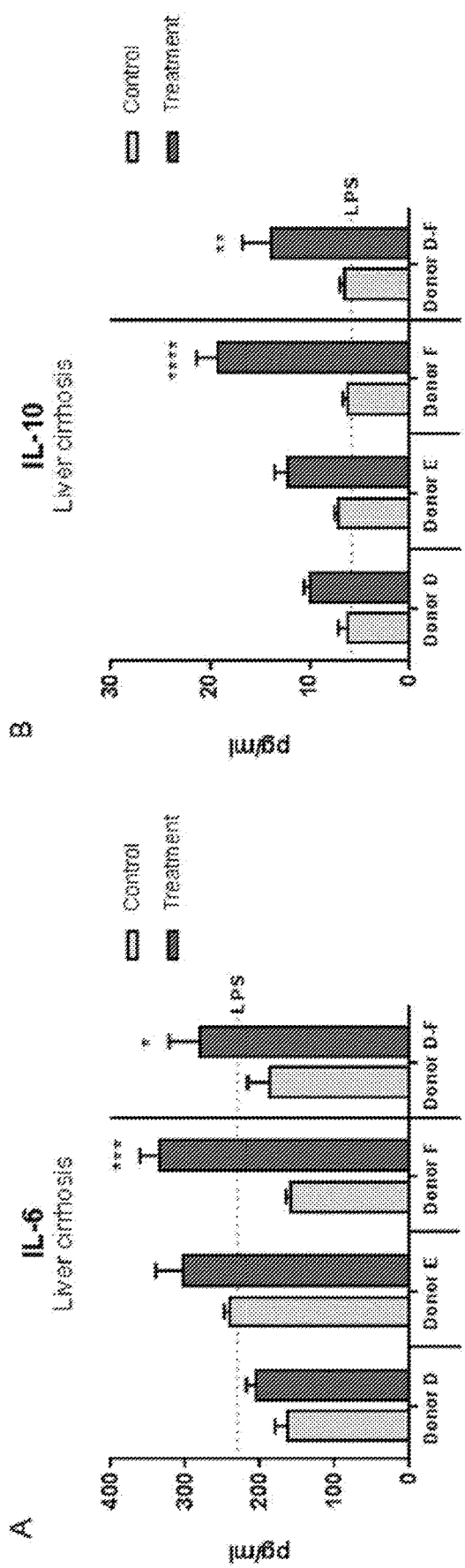
FIG. 20: Effect of colonic batch samples on secretion of IL-6 (A) and IL-10 (B). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. (*)=p<0.05; ()=p<0.01; (*)=p<0.001, (****)=p<0.0001. Data are represented for each donor separately and as the mean of all donors (Donor D-F).

Treatment colonic liver cirrhosis batch samples increased the NF-kB activity compared to the LPS+ control and compared to their own control (FIG. 19). These differences were found to be significant when taking the mean of all donors.

With respect to the secretion of the anti-inflammatory cytokines IL-6 and IL-10, SYMPROVE™ treatment samples from all donors increased IL-6 and IL-10 levels compared to their control (Figure (20).

To conclude, treatment with SYMPROVE™ resulted in colonic samples from liver cirrhosis donors increased NF-kB activity and concomitant secretion of the anti-inflammatory cytokines IL-6 and IL-10, indicative of an anti-inflammatory/tolerogenic gut phenotype following SYMPROVE™ treatment.

The mean TNFa and CXCL10 response was elevated in the SYMPROVE™ treatment samples compared to controls, though this was not statistically significant.

Figure 21:
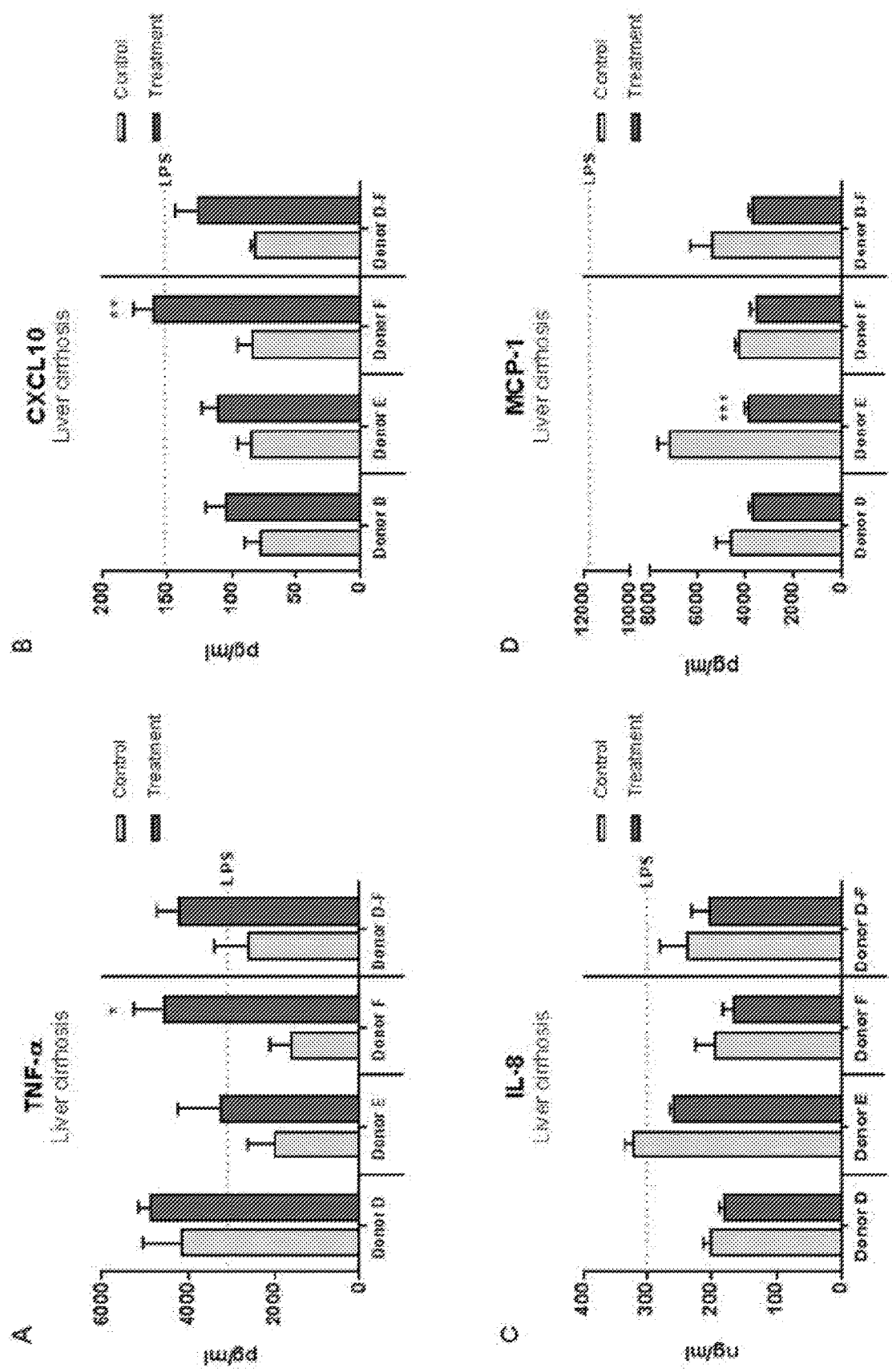
FIG. 21: Effect of colonic batch samples on secretion of TNF-α (A), CXCL10 (B), IL-8 (C) and MCP-1 (D). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. (*)=p<0.05; ()=p<0.01; (*)=p<0.001. Data are represented for each donor separately and as the mean of all donors (Donor D-F).

With respect to the secretion of IL-8 and MCP-1, all but one liver cirrhosis batch samples decreased their secretion compared to the LPS+ control and all SYMPROVE™ treatment samples decreased the secretion of IL-8 and MCP-1 compared to their respective controls (FIG. 21).

To conclude, treatment with SYMPROVE™ resulted in colonic samples from liver cirrhosis donors decreased the secretion of IL-8 and MCP-1 indicative of an anti-inflammatory/tolerogenic gut phenotype following SYMPROVE treatment.

Parkinson's Disease

Figure 22:
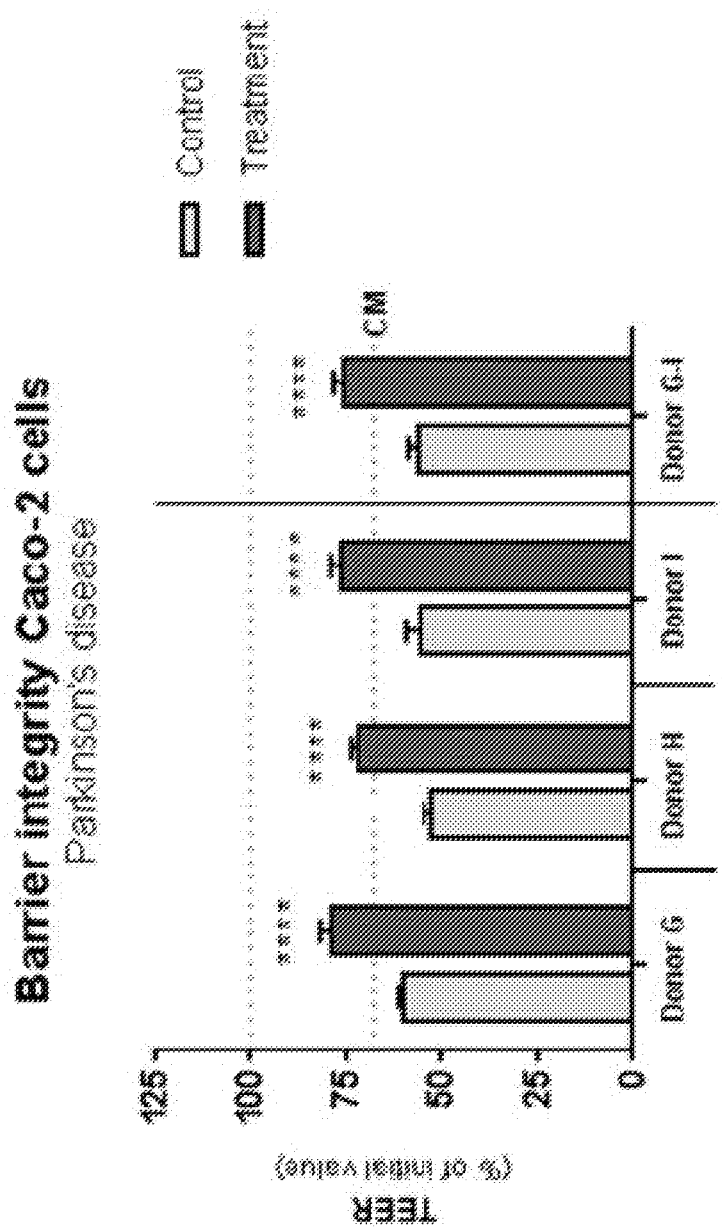
FIG. 22: Effect of colonic batch samples on transepithelial electrical resistance (TEER) of the Caco-2/THP1-Blue™ cocultures. TEER was measured 24 h after treatment of the co-cultures and each 24 h value was normalized to its corresponding 0 h value and is shown as percentage of initial value. The upper dotted line represents 100% (initial value). The lower dotted line corresponds to the experimental control CM (complete medium). Data are plotted as mean±SEM. (*) represents statistically significant differences between the treatment and control samples. (****)=p<0.0001. Data are represented for each donor separately and as the mean of all donors (Donor G-I).

The TEER of the control batch samples from Parkinson's patients decreased compared the experimental control CM, while after treatment with SYMPROVE™, the TEER increased significantly compared to their control in all the three donors tested (FIG. 22). This indicates that SYMPROVE™ had a significant protective effect on inflammation-induced intestinal epithelial barrier permeability in colonic batch samples of Parkinson's disease donors.

Figure 23:
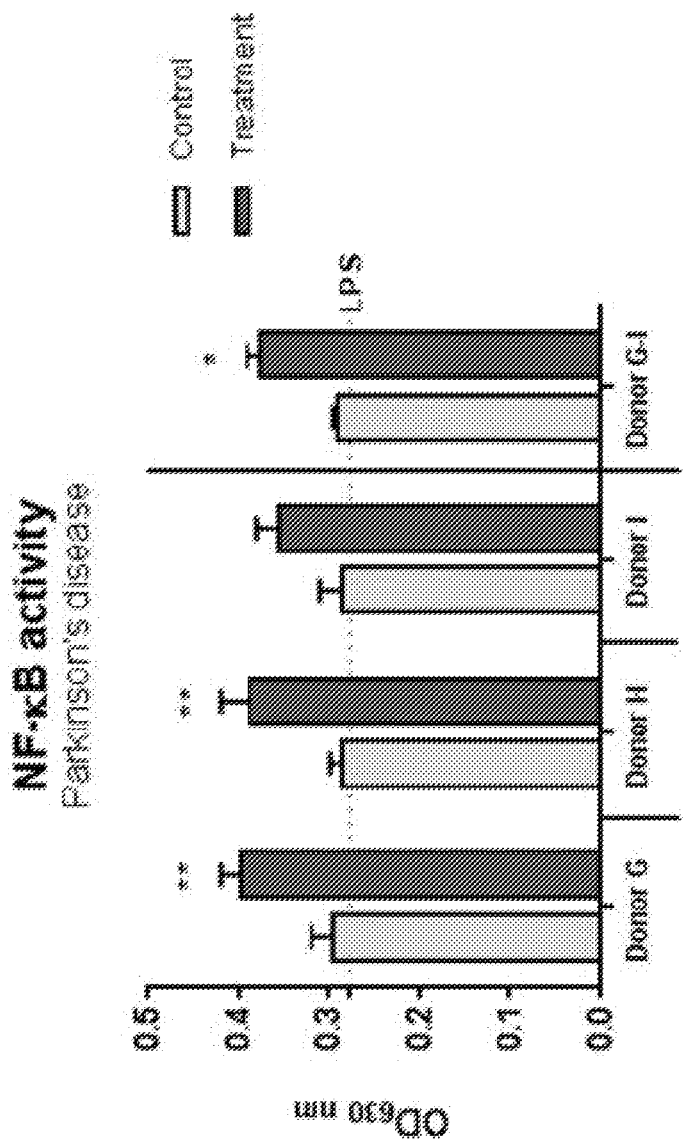
FIG. 23: Effect of colonic batch samples on NF-kB activity of THP-1-Blue™ cells. NF-kB activity levels were measured 6 h after LPS treatment on the basolateral side of the Caco-2/THP-1-Blue™ co-cultures after pre-treatment of the apical side for 24 h with the colonic batch samples. The dotted line corresponds to the experimental control LPS+. Data are plotted as mean±SEM. (*) represents statistically significant differences between the treatment and control samples. (*)=p<0.05; (**)=p<0.01. Data are represented for each donor separately and as the mean of all donors (Donor G-I).

SYMPROVE™ treatment samples of all Parkinson's' disease donors increased the NF-kB activity compared to both the LPS+ and batch control samples, while the control samples kept the NF-kB activity at the level of the LPS+ control (FIG. 23). The mean increased NF-kB activity compared to the batch controls was statistically significant.

Figure 24:
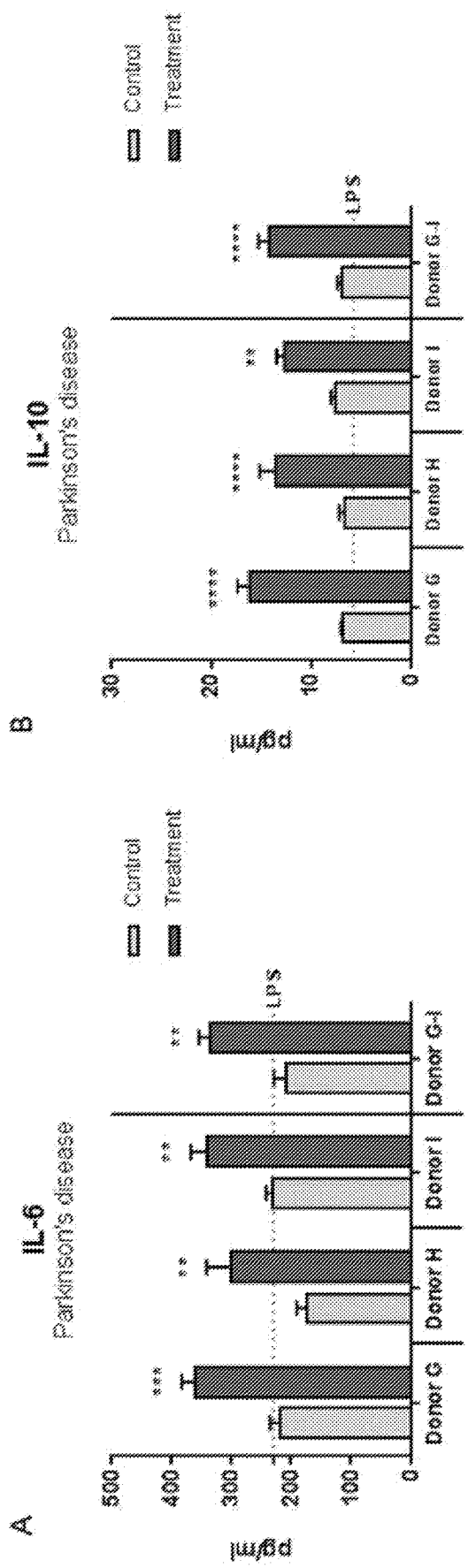
FIG. 24: Effect of colonic batch samples on secretion of IL-6 (A) and IL-10 (B). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. ()=p<0.01; (*)=p<0.001, (****)=p<0.0001. Data are represented for each donor separately and as the mean of all donors (Donor G-I).

All SYMPROVE™ treatment batch samples increased the secretion of the anti-inflammatory cytokines IL-6 and IL-10, compared to the LPS+ control (FIG. 24). In addition, for all donors, the increased secretion of IL-6 and IL-10 was found to be significantly different compared to their control.

Thus, for all Parkinson's disease donors, SYMPROVE™ treated colonic batch samples increased NF-kB activity and concomitant secretion of the anti-inflammatory cytokines IL-6 and IL-10 compared to their untreated controls, indicative of an anti-inflammatory/tolerigenic gut phenotype in these treated samples.

The TNFa response was variable across donors and no significant mean response was observed. For all donors, treatment with SYMPROVE™ significantly increased CXCL10 levels compared to their controls and thereby reached the same levels as the LPS+ control (FIG. 25).

Compared to the LPS+ control, all SYMPROVE™ treatment Parkinson's disease batch samples reduced the IL-8 levels (FIG. 25). For all donors, IL-8 levels tended to decrease after treatment with SYMPROVE™ compared to their respective controls.

Finally, all Parkinsons's Disease batch samples reduced MCP-1 levels compared to the LPS+ control (FIG. 25). In addition, treatment samples reduced MCP-1 levels compared to their control. This effect was found to be significantly different from the response in control samples.

Thus, for all Parkinson's disease donors, SYMPROVE™ treated colonic batch samples decreased the secretion of the chemokines IL-8 and MCP-1 and CXCL10 secretion increased.

IBD

Figure 26:
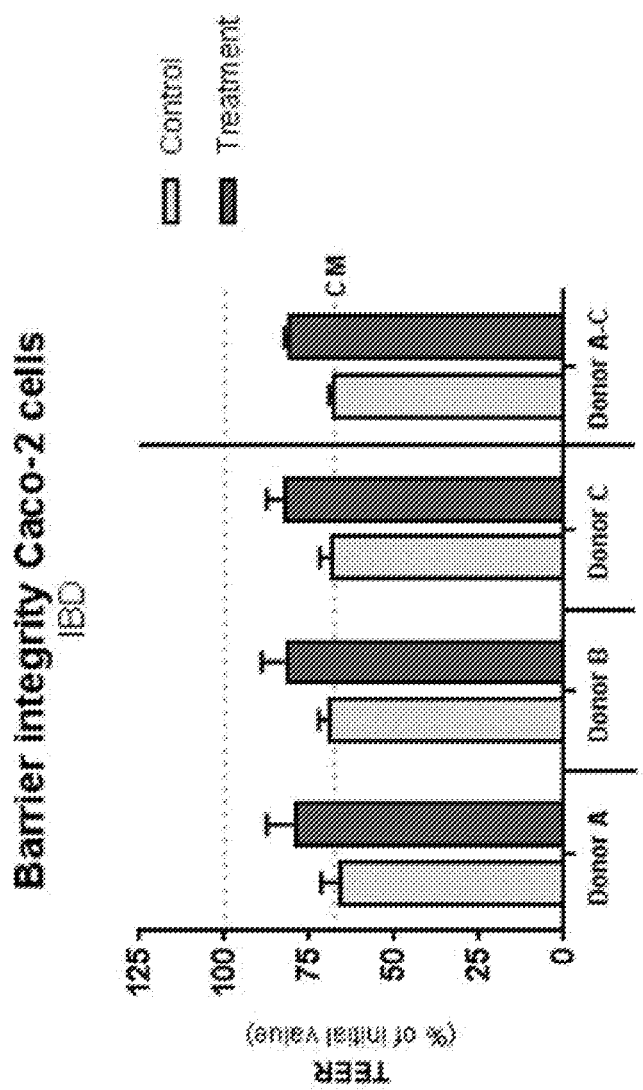
FIG. 26: Effect of colonic batch samples on transepithelial electrical resistance (TEER) of the Caco-2/THP1-Blue™ cocultures. TEER was measured 24 h after treatment of the co-cultures and each 24 h value was normalized to its corresponding 0 h value and is shown as percentage of initial value. The upper dotted line represents 100% (initial value). The lower dotted line corresponds to the experimental control CM (complete medium). Data are plotted as mean±SEM. No significant differences were found between the treatment and control samples. Data are represented for each donor separately and as the mean of all donors (Donor A-C).

Addition of control colonic batch samples to the cells did not affect the TEER compared to the experimental control CM (FIG. 26). In contrast, samples treated with SYMPROVE™ increased the TEER in all three IBD donors compared to their control. Thus, for all IBD donors, SYMPROVE™ treated colonic batch samples had a mild protective effect on inflammation-induced intestinal epithelial barrier permeability.

Figure 27:
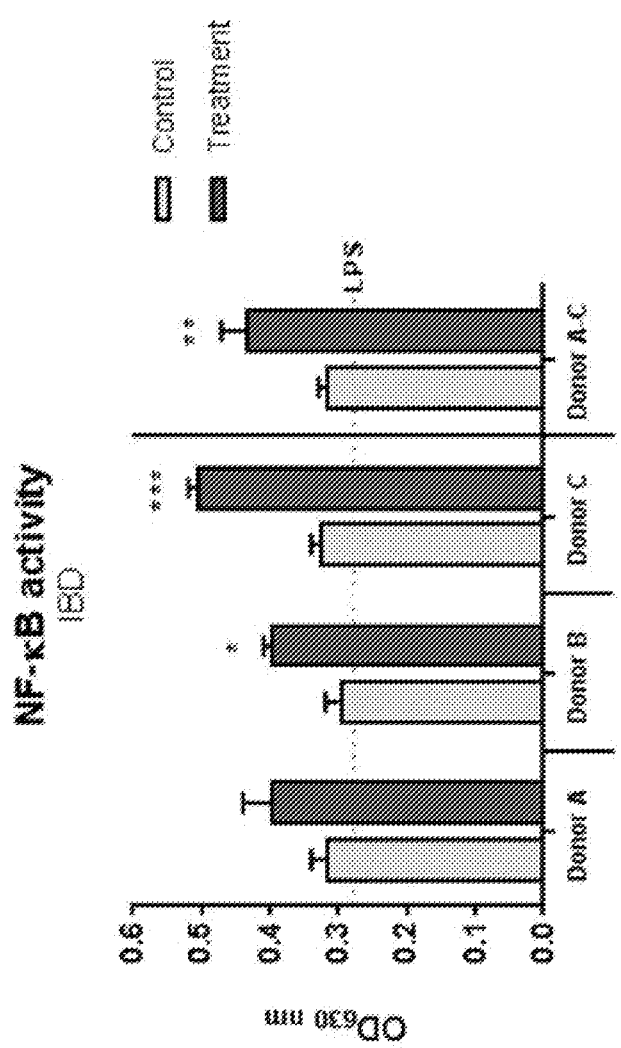
FIG. 27: Effect of colonic batch samples on NF-kB activity of THP-1-Blue™ cells. NF-kB activity levels were measured 6 h after LPS treatment on the basolateral side of the Caco-2/THP-1-Blue™ co-cultures after pre-treatment of the apical side for 24 h with the colonic batch samples. The dotted line corresponds to the experimental control LPS+. Data are plotted as mean±SEM. (*) represents statistically significant differences between the treatment and control samples. (*)=p<0.05; ()=p<0.01; (*)=p<0.001. Data are represented for each donor separately and as the mean of all donors (Donor A-C).

All colonic batch treatment samples increased the NF-kB activity compared to the LPS+ control whereas the control samples did not affect the LPS-induced NF-kB activity. (FIG. 27). Moreover, treatment with SYMPROVE™ increased the NF-kB activity in all donors, compared to their respective controls.

Figure 28:
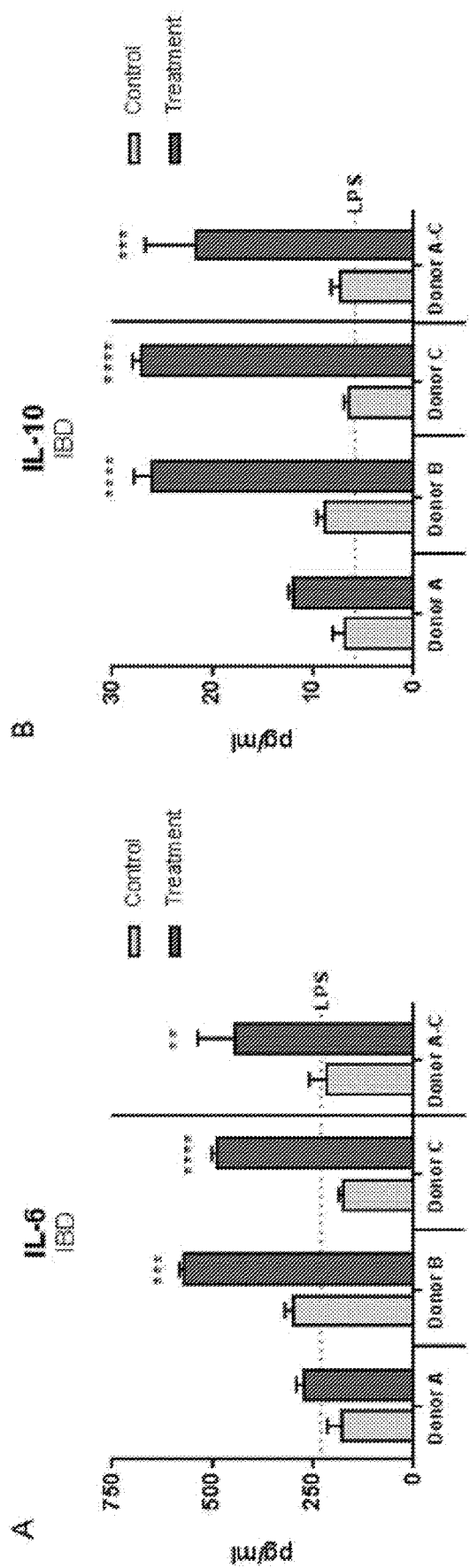
FIG. 28: Effect of colonic batch samples on secretion of IL-6 (A) and IL-10 (B). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. ()=p<0.01; (*)=p<0.001, (****)=p<0.0001. Data are represented for each donor separately and as the mean of all donors (Donor A-C).

With respect to the secretion of the anti-inflammatory cytokines IL-6 and IL-10, all treatment samples increased the secretion of IL-6 and IL-10, compared to the LPS+ control, while the control samples did not (FIG. 28). In addition, for all donors, an increase in IL-6 and IL-10 levels was observed upon treatment with SYMPROVE™ compared to their control.

To conclude, treatment with SYMPROVE™ increased NF-kB activity and concomitant secretion of the anti-inflammatory cytokines IL-6 and IL-10 in all three IBD donors.

Figure 29:
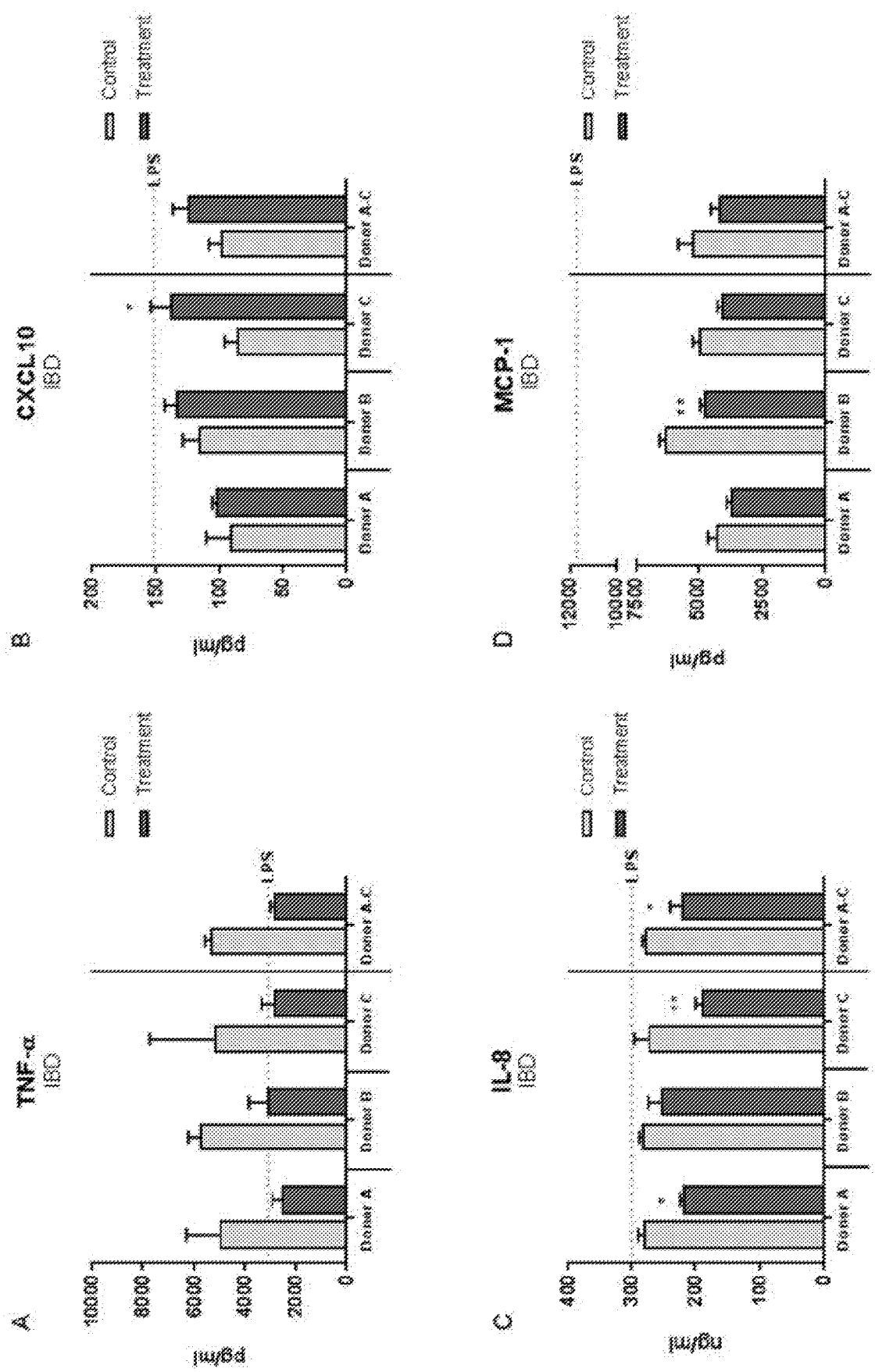
FIG. 29: Effect of colonic batch samples on secretion of TNF-α (A), CXCL10 (B), IL-8 (C) and MCP-1 (D). Cytokine levels were measured 6 h after LPS treatment on the basolateral side of the Caco-2/THP-1-Blue™ co-cultures after pre-treatment of the apical side for 24 h with colonic batch samples. The dotted line corresponds to the experimental control LPS+. Data are plotted as mean±SEM. (*) represents statistically significant differences between the treatment and control samples. (*)=p<0.05; (**)=p<0.01. Data are represented for each donor separately and as the mean of all donors (Donor A-C).

All control IBD batch samples increased the LPS-induced secretion of the pro-inflammatory cytokine TNF-α compared to the LPS+ control, whereas all treatment samples decreased TNF-α levels compared to their respective control samples and/or to the LPS+ control (FIG. 29).

With respect to the secretion of the chemokines CXCL10, IL-8 and MCP-1, a decrease in LPS-induced CXCL10 levels was observed after treatment with all IBD batch samples compared to the LPS+ control (FIG. 29). However, when looking at the mean of all IBD donors, no significant differences were observed between control and treatment on CXCL10 secretion.

Compared to both the LPS+ and batch sample controls, all SYMPROVE™ treatment samples were able to reduce IL-8 levels (FIG. 29). Moreover, following SYMPROVE™ treatment, the decrease of IL-8 secretion was significantly different between control and treatment IBD batch samples. Finally, all IBD batch samples reduced MCP-1 levels compared to the LPS+ control (FIG. 29).

To conclude, treatment with SYMPROVE™ decreased the secretion of the pro-inflammatory cytokine TNF-α and of the chemokines IL-8 and MCP-1, compared to their control IBD batch samples.

3.4 Wound Healing Assay

Liver Cirrhosis

Figure 30:
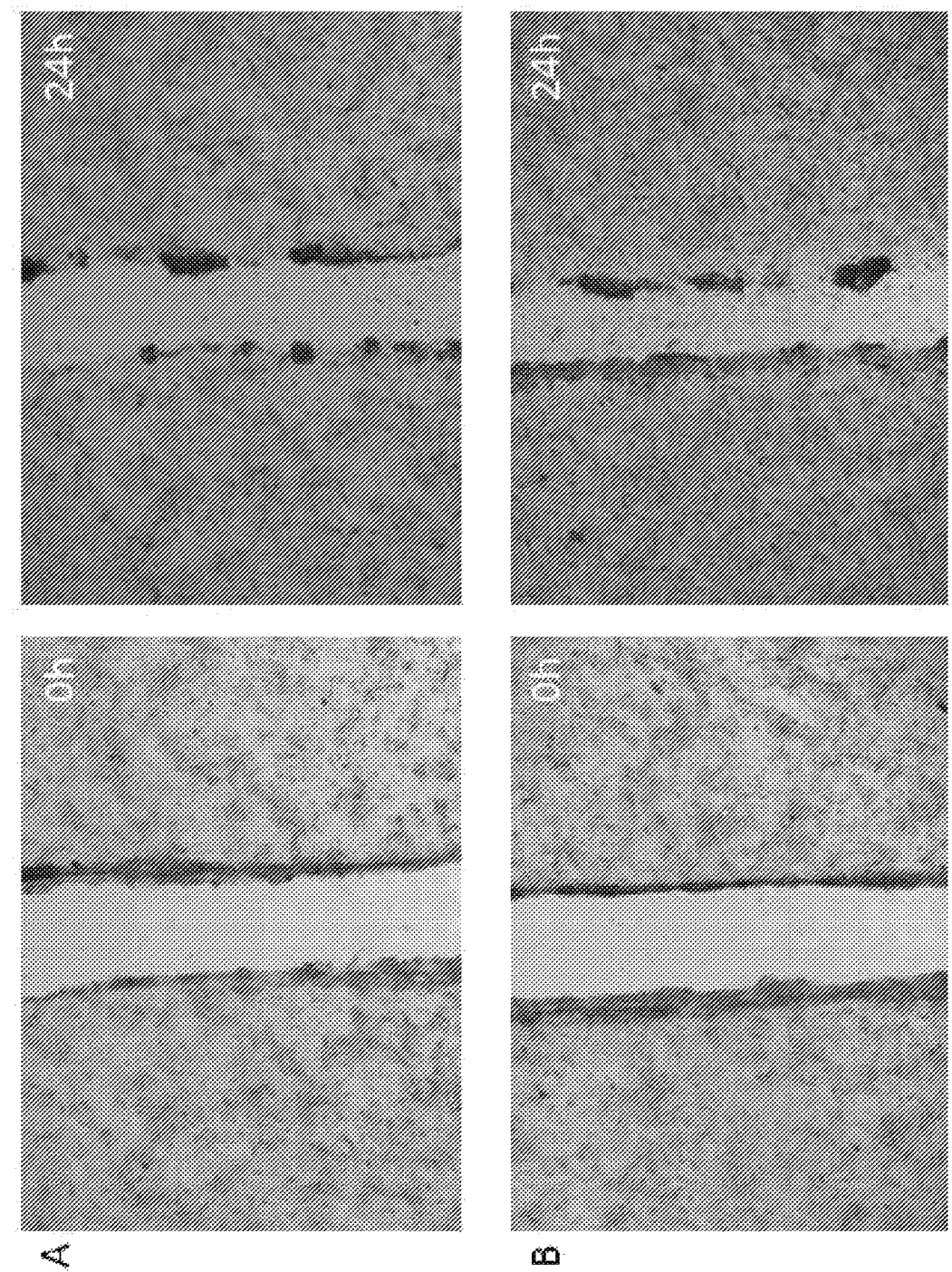
FIG. 30: Images of the wound area of T84 cells treated with control (A) and SYMPROVE™ treatment samples (B) of donor D at the start of the treatment (0 h) and after 24 h incubation (24 h).
Figure 31:
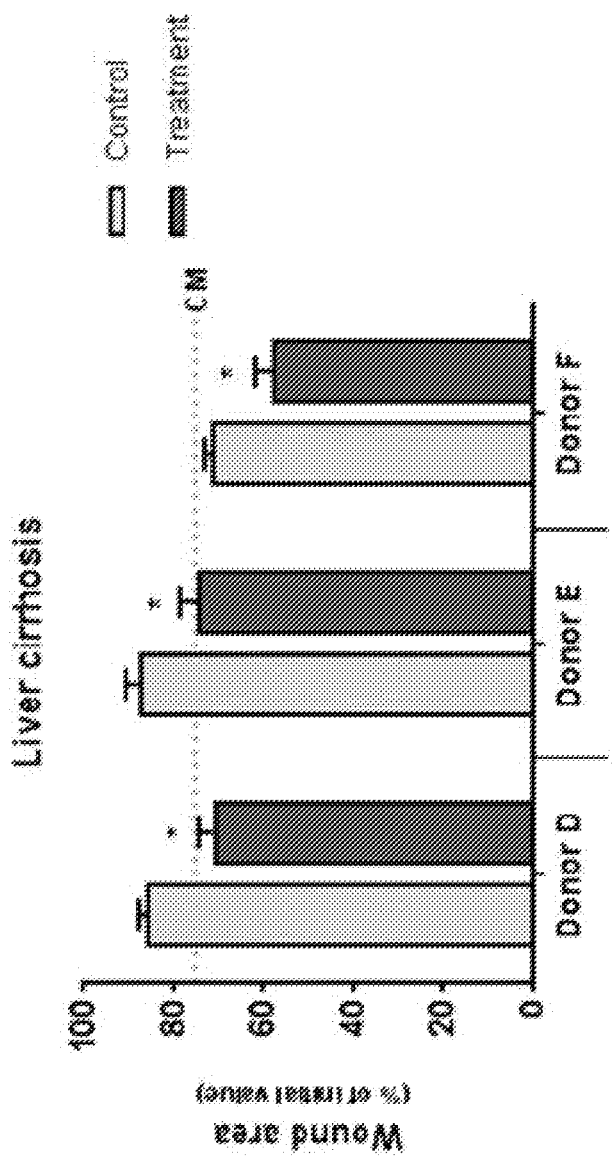
FIG. 31: Wound area after 24 h treatment with colonic liver cirrhosis batch samples. The wound area was measured 24 h after treatment of T84 cells and each 24 h value was normalized to its corresponding 0 h value and is shown as percentage of initial value. The dotted line corresponds to the experimental control CM. Data are plotted as mean±SEM. (*) represents statistically significant differences between the treatment and control samples. (*)=p<0.05.

After 24 h treatment with control liver cirrhosis samples, the wound area of donor D and E was bigger than the CM control, while Donor F behaved similar as the CM (FIG. 30 and FIG. 31). After stimulation with SYMPROVE™ treatment samples, for all donors, the wound area decreased significantly compared to their control.

Parkinson's Disease

Figure 32:
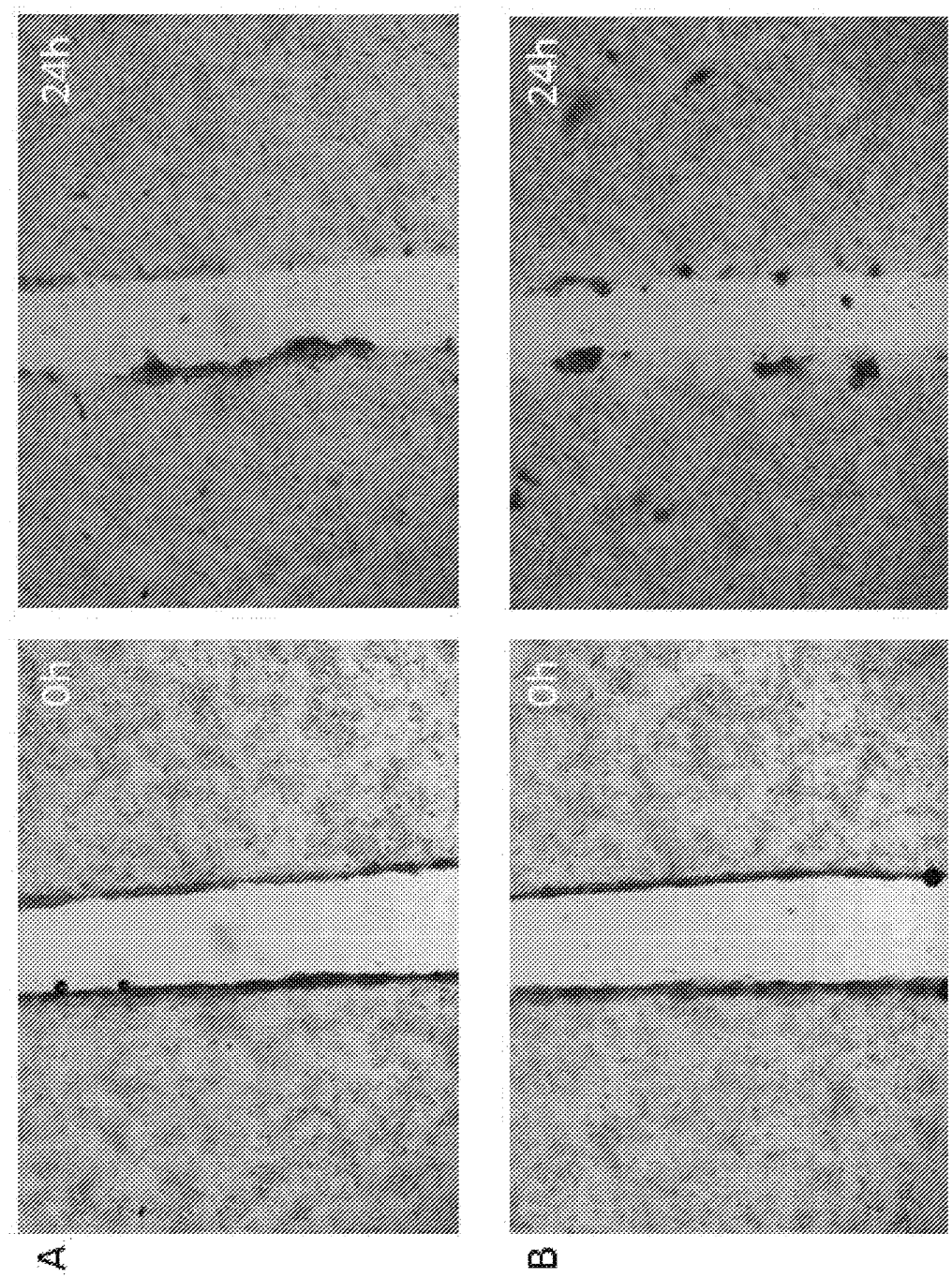
FIG. 32: Images of the wound area of T84 cells treated with control (A) and SYMPROVE™ treatment samples (B) of donor G at the start of the treatment (0 h) and after 24 h incubation (24 h).
Figure 33:
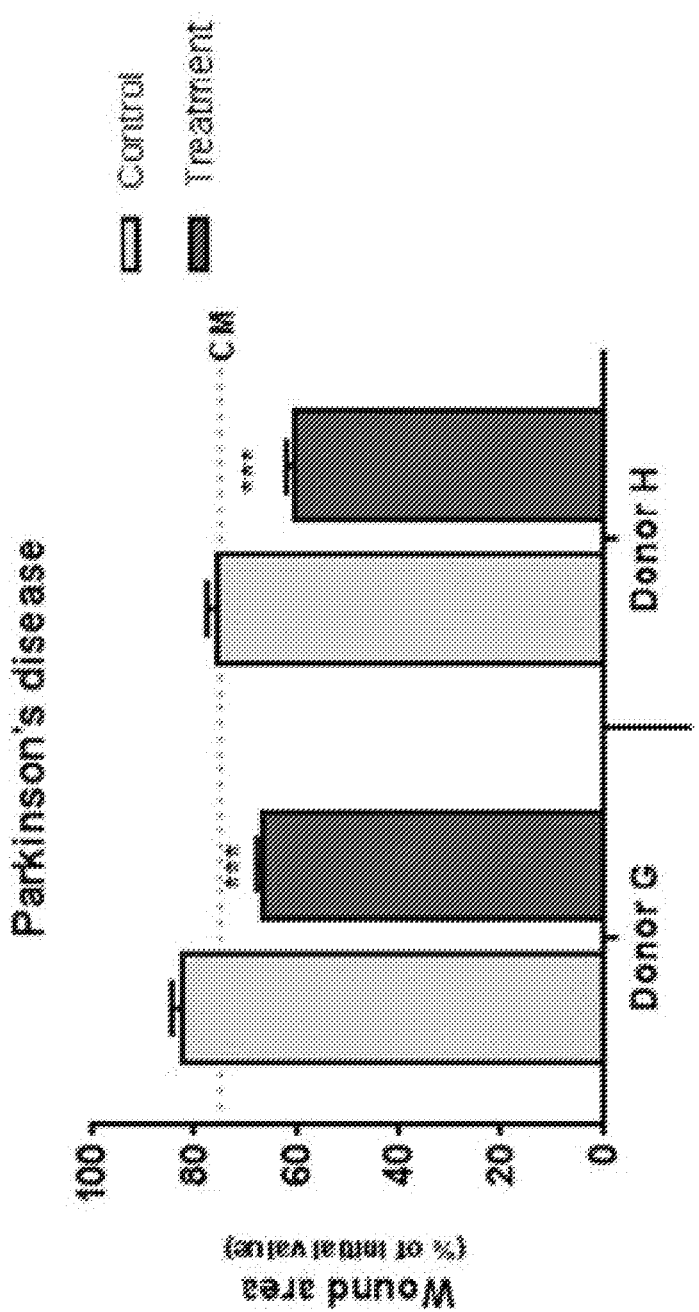
FIG. 33: Wound area after 24 h treatment with colonic Parkinson's disease batch samples. The wound area was measured 24 h after treatment of T84 cells and each 24 h value was normalized to its corresponding 0 h value and is shown as percentage of initial value. The dotted line corresponds to the experimental control CM. Data are plotted as mean±SEM. (*) represents statistically significant differences between the treatment and control samples. (***)=p<0.001.

SYMPROVE™ treatment samples of both Parkinson's disease donors tested decreased the wound area compared to both the CM control and their respective batch control samples, while the wound area of the control samples were similar to the CM control (FIG. 32 and FIG. 33).

IBD

After 24 h of incubation, the wound area of the colonic batch control samples was comparable with the negative CM control. In contrast, stimulation with the colonic IBD batch SYMPROVE™_treated samples of all donors decreased the wound area significantly compared to their control, with the biggest effect seen for donor C.

Thus, for all disease conditions, treatment with SYMPROVE™ promoted wound repair in a model of intestinal epithelial barrier damage.

4. Conclusions

These data demonstrate that, notwithstanding the different states of dysbiosis of the microbiota representing the different diseases, SYMPROVE™ resulted in consistent treatment effects between the different patient groups.

Administration of SYMPROVE™ resulted in increased production of acetate, increased production of propionate, and increased production of butyrate. This shift to SCFA production indicative of a healthier gut appears not to be driven by the transient passage of probiotic bacteria present in SYMPROVE™. Instead, the probiotic bacteria become integrated into both the luminal and mucosal compartments of the gut, and the consequential rebalancing of the microbiota population addresses the dysbiosis present before treatment and promotes production of SCFAs, indicative of a healthier gut.

In the Caco-2/THP1-blue™ co-culture model of the gut epithelia, it was shown that administration of SYMPROVE™ was also able to alter the immuno-reactivity status of the gut immune cells. In particular, cells treated with extracts treated with SYMPROVE™ exhibited a more tolerogenic or anti-inflammatory phenotype. Cells exhibiting this phenotype responded to LPS stimulation by producing more anti-inflammatory cytokines such as IL-6 and IL-10, and lower levels of pro-inflammatory cytokines such as IL-8 and chemokines such as MCP-1. This tolerogenic or anti-inflammatory phenotype induced by SYMPROVE™ was evident in samples from healthy donors, as well as from donors suffering from liver cirrhosis, Parkinson's Disease or IBD.

In IBD patients, it was also demonstrated that SYMPROVE™ reduced TNFa production, when colonic samples from control patients had a marked pro-inflammatory effect. This further demonstrates the anti-inflammatory effect of SYMPROVE™, as it evidently counter-acts the general pro-inflammatory environment present in the gut of untreated IBD sufferers. No significant effect on TNFa levels was observed for the liver cirrhosis samples, possibly because the control samples from these patients did not have the same general pro-inflammatory effect sufficient to induce high levels of TNFa production.

Example 3

Example 2 demonstrates that Parkinson's disease patients exhibit gastrointestinal dysbiosis, as their gut microbiota differs from that of healthy donors. It is hypothesised that gastrointestinal dysbiosis could contribute to the pathology of Parkinson's disease. Specifically, the disrupted microbiota may lead and/or be caused by inflammation, which itself leads to an increase in gut permeability ('leaky gut'). The increase in gut permeability may lead to increased expression and aggregation of misfolded alpha-synuclein, the protein aggregate characteristic of Parkinson's disease. The alpha-synuclein can then be transmitted to the brain via the vagus nerve, which is the conduit of the gut-brain axis. Additionally, chronic intestinal inflammation secondary to alterations of gut microbiota may also lead to systemic inflammation and altered blood brain barrier leading to inflammation in the brain, which is a known pathophysiological event of Parkinson's disease.

Example 2 demonstrates that administration of SYMPROVE™ is able to modulate the growth of gut bacterial phyla, and also to promote SCFA production in the gut of Parkinson's disease patients. Furthermore, following treatment with SYMPROVE™, the gastrointestinal environment of Parkinson's disease patients exhibits improved SCFA production, improved gut integrity and a reduced inflammatory environment.

Thus, without wishing to be bound by theory, it is hypothesised that SYMPROVE™ can treat Parkinson's disease, for example by one or more, or all of: promoting intestinal health, stimulating gut SCFA production, treating intestinal dysbiosis, promoting intestinal barrier integrity and/or promoting a tolerogenic gut phenotype. Doing so is expected to limit the formation of aggregated misfolded alpha-synuclein, as well as limiting the transport of any such aggregates to the brain.

SYMPROVE™ therefore offers a treatment for Parkinson's disease that could slow development of the neurological or motor symptoms. In addition, Parkinson's patients are known to suffer from disrupted bowel activity such as constipation. The beneficial effects of SYMPROVE™ on gut health demonstrated herein will also therefore be able to relieve these non-motor symptoms of Parkinson's disease.

Reports from individual case studies suggest an improvement in motor and non-motor aspects of Parkinson's after intake of SYMPROVE™ for a variable period.

The following phase I clinical trial further demonstrates the treatment of Parkinson's disease with SYMPROVE™:

Main Hypotheses

The study will test the following hypotheses in persons with Parkinson's (PwP) with constipation.

Oral SYMPROVE™ intake in PwP as opposed to placebo intake will lead to:
1. improvement of motor and non-motor state with a specific focus on gastrointestinal symptoms;
2. improvement of overall burden of non-motor symptoms (NMS);
3. a systemic anti-inflammatory beneficial effect on a range of systemic inflammation markers;
4. improvement of quality of life.

Plan of Investigation

Study Design

The study is a double blind, placebo-controlled study. Participants will be randomly allocated at entry to one of two treatments arms:
a) 'Usual treatment (UT)+Placebo' or
b) 'UT+SYMPROVE™'

UT will consist of medication with dosage stable for the duration of the study (3 months). Furthermore, participant will maintain diet and physical activity stable.

Study Participants

N=60 patients with Parkinson's will be recruited into the study, with n=30 allocated to each treatment arm.

Eligibility Criteria
a) Inclusion:
   Age of 18 and upwards
   diagnosis of Parkinson's disease (PD) according to Movement Disorder Society clinical criteria and UK PD Brain Bank criteria for PD
   Hoehn Yarhr stage32≥2 and ≤4
   diagnosis of functional constipation according to the Rome IV criteria and less than 3 bowel movements per week.
b) Exclusion:
   diagnosis or suspicion of other causes for parkinsonism
   advanced-stage therapies (deep brain stimulation, continuous levodopa duodenal infusion, and apomorphine subcutaneous infusion)
   any inflammatory bowel disease (Crohn's disease and Ulcerative colitis) or diseases of the colon
   previous surgery on the gastrointestinal tract
   history of laxative abuse
   ongoing artificial nutrition (either enteral or parenteral)
   regular use of probiotics (excluding regular yogurt consumption)
   previous intolerance and/or adverse reactions to probiotics
   previous use of SYMPROVE™
   recent or current use of any antibiotics (within 4 weeks before the start of the study)
   swallowing issues interfering with the safety intake of liquid
   pregnancy or lactation
   major systemic disease (e.g. heart failure, renal failure, liver cirrhosis, cancer, etc.)
   any condition interfering with the ability to give the informed consent
   enrolment in another simultaneous investigational trial Blinding Randomisation will be double-blind, and 1:1 (computer-generated block randomisation will be performed by staff not directly involved in the study).

Dose

A daily dose of SYMPROVE™ oral solution (70 mls) will be administered for the active treatment condition and matched placebo for three months. The latter is a similar liquid in appearance and taste and will be supplied by the probiotic manufacturer. This dose of SYMPROVE™ has been found to be safe and well-tolerated in previous studies Assessments Assessments will include:
1. Demographic and Clinical Characteristics Demographic information and clinical characteristics will include date of birth, gender, age at assessment, age at PD onset, diseased duration, Hoehn and Yahr staging (PD motor staging), medication regime (including laxatives), time to 'ON' status (time required for an adequate control of PD symptoms after PD medication intake), socio-demographic data and bowel habits.

2. Daily Stool Diary

Eligible patients will be asked to complete a 2-week stool diary at baseline over the last 2 weeks of treatment.

The daily stool diary will include recording frequency of bowel movements and describing consistency of stool using the Bristol stool scale and other related symptoms.

3. Nutrition and Physical Activity Assessment

A nutrition and physical activity proforma will be completed at baseline and post-treatment assessment.

4. Validated Questionnaires and Scales
   a) Movement Disorder Society Unified Parkinson's Disease Rating Scale (MDS-UPDRS) part Ill and IV (ON)

The MDS-UPDRS has four parts: part I (Non-motor Experiences of Daily Living) with six rater-based items and seven for self-assessment; part II (Motor Experiences of Daily Living) with 13 patient-based items; part Ill (Motor Examination) with 33 scores based on 18 items, due to left, right and other body distributions; part IV (Motor Complications) with six items. Each question is anchored with five responses that are linked to commonly accepted clinical terms: 0=normal; 1=slight, 2=mild, 3=moderate, and 4=severe. The total score for each part is obtained from the sum of the corresponding item scores b) Non-motor symptoms scale (NMSS)

The NMSS is composed of 30 items grouped in nine domains: cardiovascular (2 items), sleep/fatigue (4 items), mood/cognition (6 items), perceptual problems/hallucinations (3 items), sexual function (2 items), and miscellaneous (4 items). Each item scores on a multiple of severity (from 0 to 3) and frequency scores (from 1 to 4). The total score runs from 0 to 360.

c) Montreal Cognitive Assessment (MoCA)

The MoCA is a widely used screening assessment for detecting cognitive impairment. It is composed by 12 items and the maximum score is 30 points, with higher scores indicating better performance.

d) Clinical Impression of Severity Index for Parkinson's disease (CISI-PD)

The CISI-PD is a severity index formed by four items (motor signs, disability, motor complication and cognitive status) rated 0 (not at all) to six (very severe or severely disabled). A total score is calculated by summing the item scores.

e) King's Parkinson's Disease pain scale (KPPS)

The KPPS is the first and only scale which identify and grade the different types of pain in PD: musculoskeletal, chronic, fluctuation-related, nocturnal, oro-facial, oedema-related and radicular pain.

f) Irritable bowel syndrome Severity Score (IBSSS)

IBSSS is a scoring system for irritable bowel syndrome incorporating pain, distension, bowel dysfunction and quality of life/global well-being. The maximum achievable score is 500 (the sum of each item score).

g) Parkinson's Disease Sleep Scale 2 (PDSS 2)

The PDSS 2 is the most recent validated and updated version of the original 15 item PDSS. It is a self-rating questionnaire composed by 15 items about various sleep and nocturnal disturbances which are to be rated by the patients using one of five categories, from 0 (never) to 4 (very frequent). PDSS-2 total score ranges from 0 (no disturbance) to 60 (maximum nocturnal disturbance).

h) Parkinson's Disease Questionnaire-8 (PDQ-8)

The PDQ-8 is a specific instrument for assessment of health-related quality of life of PD patients. It includes 8 items, each one scoring from 0 to 4. The PDQ-8 Summary Index is expressed as a percentage of the sum of each item score on the maximum possible scale score.

i) Hospital Anxiety and Depression Scale (HADS)

The HADS is a self-assessment scale for detecting states of depression and anxiety. It is formed by two subscales: anxiety and depression, each with seven items scored from 0 (least severe) to 3 (more severe). A subscore is calculated for each subscale resulting from the sum of each item score.

j) Parkinson Fatigue Scale-16 (PFS-16)

The PFS is a 16-item patient-rated scale assessing physical aspect of fatigue and its impact on daily function in PD patients. The item response option range from one ('strongly disagree') to five ('strongly agree'). The total score is based on the sum of each items scores.

k) Patient Global Impression of Change (PGIC)

PGIC is s a self-rated, 7-point, evaluative instrument for assessment of overall treatment experience.

5. Parkinson's KinetiGraph (PKG) Objective Recording

Objective recordings will be performed using a 7-day Parkinson's KinetiGraph (PKG) monitoring. The PKG is a wearable device worn on the wrist of the most affected side of the patient. PKG reports include several scores and measures as shown below:

| Scores | Graphs an summary tables |
|---|---|
| Bradykinesia score (BKS) | Bradykinesia and dyskinesia daily an summary plots and severity percentage summary |
| Dyskinesia score (DKS) | Off wrist summary |
| Fluctuation score (FDS) | Immobility summary |
| Percent time immobile (PTI) | Tremor summary |
| Percent time tremor (PTT) | Button pressing |

6. Smart Belt Objective Recording

The smart belt is a wearable sensor aimed to record the bowel movements during digestion. The system will be placed around the participant's abdomen in an easy and comfortable way during a meal.

7. Laboratory Tests for Peripheral Inflammatory Markers

Blood samples will be collected at baseline and post-treatment assessment in order to assess peripheral inflammatory markers 8. Gut Microbiome Analysis Participants will collect a stool sample at home and send it for analysis both at baseline and post-treatment.

Assessments will be performed at baseline and at the end of the treatment (3 month+/−1 week)

Outcome Measures

All outcomes will be measured as change from the baseline to end of 3-month treatment (SYMPROVE™/placebo).

Primary Outcomes
  Change in:
  number of bowel movements (BMs) per week
  NMSS total score.

Secondary Outcomes
  Change in:
  Number of laxatives per week
  IBSSS
  MDS-UPDRS part III and IV (ON)
  Time to 'on' state
  CISIPD
  PGIC
  PDQ-8
  PDSS 2
  PFS-16
  HADS
  MoCA
  KPPS
  peripheral inflammatory markers levels
  wearable sensor recorded scores (PKG, Smart Belt scores)
  changes in gut microbiome Patients receiving SYMPROVE™ will exhibit improvement in one or more of the primary and/or secondary outcomes compared to before treatment.

The invention claimed is:

1. A method of treating Parkinson's Disease in a subject, the method comprising administering to the subject a liquid, non-dairy probiotic preparation comprising a population of lactic acid bacteria, wherein the population of lactic acid bacteria comprises one or more of *Lactobacillus rhamnosus*, *Lactobacillus plantarum* and *Enterococcus faecium* bacteria, wherein administration of the probiotic preparation improves motor symptoms in the subject.

2. The method according to claim 1, wherein administration of the probiotic preparation further improves non-motor symptoms and/or systemic inflammatory markers in the subject.

3. The method according to claim 1, wherein administration of the probiotic preparation further improves non-motor symptoms in the subject, optionally improves gastrointestinal non-motor symptoms in the subject.

4. The method according to claim 1, wherein administration of the probiotic preparation further improves intestinal barrier integrity.

5. The method according to claim 1, wherein administration of the probiotic preparation further improves intestinal barrier repair.

6. The method according to claim 1, wherein administration of the probiotic preparation promotes a tolerogenic gut phenotype in the subject.

7. The method according to claim 1, wherein administration of the probiotic preparation treats Parkinson's Disease in the subject by reducing the severity or slowing the progression of motor symptoms or by slowing the onset of motor symptoms.

8. The method according to claim 1, wherein the subject is in a state of gastrointestinal dysbiosis, optionally wherein the subject is exhibiting an elevated level of Firmicutes and/or a reduced level of Bacteroidetes in their gut microbiota compared to healthy controls.

9. The method according to claim 1, wherein the method promotes production of one or more anti-inflammatory molecules by intestinal epithelial cells, optionally wherein the one or more anti-inflammatory molecules are selected from IL-6 and IL-10.

10. The method according to claim 1, wherein the method reduces production of one or more pro-inflammatory molecules by intestinal epithelial cells, optionally wherein the one or more pro-inflammatory molecules are selected from CXCL-10, TNFα, IL-8 and MCP-1.

11. The method according to claim 1, wherein the method promotes production of one or more SCFAs.

12. The method according to claim 1, wherein the method reduces production of one or more branched chain fatty acids (BCFA) and/or ammonium by the subject's gut microbiota.

13. The method according to claim 12 wherein the one or more BCFAs is selected from isobutyrate, isovalerate and 2-methylbutyrate.

14. The method according to claim 1, wherein the probiotic composition is administered to the subject at least once a week.

15. The method according to claim 1, wherein the probiotic composition is administered to the subject for a period of at least 1 month, at least 2 months or at least 3 months.

16. The method according to claim 1, wherein the population of lactic acid bacteria comprises *Lactobacillus plantarum* bacteria.

17. The method according to claim 1, wherein the population of lactic acid bacteria further comprises *Lactobacillus acidophilus* bacteria.

18. The method according to claim 1, wherein the population of lactic acid bacteria comprises *Lactobacillus rhamnosus, Lactobacillus acidophilus, Lactobacillus plantarum* and *Enterococcus faecium* bacteria.

19. The method according to claim 1, wherein the method promotes production of one or more of acetate, propionate or butyrate.

20. The method according to claim 1, wherein the probiotic composition is administered to the subject once a day.

* * * * *